(12) United States Patent
Xu et al.

(10) Patent No.: US 6,657,056 B2
(45) Date of Patent: *Dec. 2, 2003

(54) COMPOUNDS FOR IMMUNOTHERAPY OF PROSTATE CANCER AND METHODS FOR THEIR USE

(75) Inventors: Jiangchun Xu, Bellevue, WA (US); Davin C. Dillon, Redmond, WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 183 days.

(21) Appl. No.: 09/115,453

(22) Filed: Jul. 14, 1998

(65) Prior Publication Data

US 2002/0090372 A1 Jul. 11, 2002

Related U.S. Application Data

(63) Continuation-in-part of application No. 09/030,607, filed on Feb. 25, 1998, now Pat. No. 6,262,245, which is a continuation-in-part of application No. 09/020,956, filed on Feb. 9, 1998, now Pat. No. 6,261,562, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.[7] .............................................. C07H 21/04

(52) U.S. Cl. .................. 536/24.1; 536/23.1; 536/23.4; 435/6; 435/69.1; 435/320.1

(58) Field of Search ......................... 424/140; 536/23.1, 536/23.5, 241, 23.4; 514/44, 2; 435/455, 6, 69.1, 320.1

(56) References Cited

U.S. PATENT DOCUMENTS

| | | | |
|---|---|---|---|
| 5,786,148 A | 7/1998 | Bandman et al. | 435/6 |
| 6,130,043 A | 10/2000 | Billing-Medel et al. | 435/6 |
| 6,252,047 B1 | 6/2001 | Billing-Medel et al. | 530/350 |
| 6,261,562 B1 * | 7/2001 | Xu et al. | 424/185.1 |
| 6,262,245 B1 * | 7/2001 | Xu et al. | 536/23.5 |
| 2002/0086301 A1 | 7/2002 | Billing-Medel et al. | 435/6 |

FOREIGN PATENT DOCUMENTS

| | | |
|---|---|---|
| EP | 652 014 A1 | 5/1995 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/30758 | 11/1995 |
| WO | WO 96/21671 | 7/1996 |
| WO | WO 00/04149 | 1/2000 |
| WO | WO 01/25272 | 4/2001 |
| WO | WO 01/34802 | 5/2001 |

OTHER PUBLICATIONS

Gao et.al.; Blinded Evaluation of Reverse Transcriptase–Polymerase Chain Reaction Prostate–Specific Antigen Peripheral Blood Assay For . . . Cancer, 1999, Urology 53: 714–721.*
Anderson, W.F. Nature 392:25–30, Apr. 1998.*
Verma et al. Nature 389:239–242, Sep. 1997.*
Stedman's Medical Dictionary—definition of vaccine, four pages, 1995.*
Bowie et al. Science 257:1306–10, Mar. 1990.*
El–Shirbiny, Prostatic Specific Antigen, *Advances In Clinical Chemistry 31*: 99–133, 1994.
Robson et al., "Identification of prostatic androgen regulated genes using the differential display technique," *Proceedings Of The American Association For Cancer Research Meeting 86, 36*: p. 266, Abstract No. 1589, 1995.
Short et al., "λ ZAP: a bacteriophage λ expression vector with in vivo excision properties," *Nucleic Acids Research 16*(15): 7583–7600, 1988.
Alexeyev et al., "Improved antibiotic–resistance gene cassettes and omega elements for *Escherichia coli* vector construction and in vitro deletion/insertion mutagenesis," *Gene 160*: 63–67, 1995.
Blok et al., "Isolation of cDNAs That Are Differentially Expressed Between Androgen–Dependent and Androgen–Independent Prostate Carcinoma Cells Using Differential Display PCR," *The Prostate 26*: 213–224, 1995.
Database EMBL Accession No. AA453562, Jun. 11, 1997, Hillier et al., "Homo Sapiens cDNA Clone 788180."
Hara et al., "Characterization of cell phenotype by a novel cDNA library subtraction system: expression of CD8α in a mast cell–derived interleukin–4–dependent cell line," *Blood 84*(1):189–199, Jul. 1, 1994.
Nelson et al., Genbank Accession No. NP_004908, March 18, 2000.
Sherman et al., "Selecting T cell receptors with high affinity for self–MHC by decreasing the contribution of CD8," *Science 258*(5083):815–818, Oct. 30, 1992.
Theobald, et al., "Targeting p53 as a general tumor antigen," *Proc. Natl. Sci. USA 92*(25):11993–11997, Dec. 5, 1995.
Vasmatzis et al., "Discovery of three genes specifically expressed in human prostate by expressed sequence tag database analysis," *Proc. Natl. Acad. Sci. USA 95*(1):300–304, Jan. 6, 1998.

(List continued on next page.)

*Primary Examiner*—Deborah Crouch
*Assistant Examiner*—Joseph Woitach
(74) *Attorney, Agent, or Firm*—Seed IP Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

10 Claims, No Drawings

OTHER PUBLICATIONS

NCBI Blast Search. SEQ ID NO:10 agaist GenBank+EMBL+DDBJ+PDB sequences, but no EST, STS, GSS, or phase 0,1 or 2 HTGS sequences. Apr. 7, 2003.

NCBI Blast Search. SEQ ID NO:10 agaist GenBank+EMBL+DDBJ+PDB sequences from EST Divisions. Feb. 19, 2003.

NCBI Blast Search. SEQ ID NO:11 agaist GenBank+EMBL+DDBJ+PDB sequences, but no EST, STS, GSS, or phase 0,1 or 2 HTGS sequences. Apr. 7, 2003.

NCBI Blast Search. SEQ ID NO:11 agaist GenBank+EMBL+DDBJ+PDB sequences from EST Divisions. Apr. 7, 2003.

GenBank Accession No. AF047020, Feb. 1, 1999.

Schmidt–Wolf et al., "Activated T cells and cytokine–induced CD3+ CD3$^+$ CD56$^+$ killer cells," *Annals of Hematology* 74:51–56, 1997.

* cited by examiner-

COMPOUNDS FOR IMMUNOTHERAPY OF PROSTATE CANCER AND METHODS FOR THEIR USE

REFERENCE TO RELATED APPLICATIONS

This application is a continuation-in-part of U.S. patent application Ser. No. 09/030,607, filed Feb. 25, 1998, U.S. Pat. No. 6,262,245 which is a continuation-in-part of U.S. patent application Ser. No. 09/020,956, filed Feb. 9, 1998, U.S. Pat. No. 6,261,562 which is a continuation-in-part of U.S. patent application Ser. No. 08/904,804, filed Aug. 1, 1997, now abandoned, which is a continuation-in-part of U.S. patent application Ser. No. 08/806,099, filed Feb. 25, 1997, now abandoned.

TECHNICAL FIELD

The present invention relates generally to compositions and methods for the treatment of prostate cancer. The invention is more particularly related to polypeptides comprising at least a portion of a prostate protein and to DNA molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for prostate cancer.

SUMMARY OF THE INVENTION

The present invention provides compounds and methods for immunotherapy of prostate cancer. In one aspect, isolated polypeptides are provided comprising at least an immunogenic portion of a prostate tumor protein or a variant of said protein that differs only in conservative substitutions and/or modifications, wherein the prostate tumor protein comprises an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227 and 228, the complements of said nucleotide sequences and sequences that hybridize to a sequence of SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227 and 228 under moderately stringent conditions In related aspects, isolated DNA molecules encoding the above polypeptides are provided. In specific embodiments, such DNA molecules include sequences provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227 and 228. The present invention further provides expression vectors comprising the above DNA molecules and host cells transformed or transfected with such expression vectors. In preferred embodiments, the host cells are selected from the group consisting of *E. Coli*, yeast and mammalian cells.

In another aspect, the present invention provides fusion proteins comprising a first and a second inventive polypeptide or, alternatively, an inventive polypeptide and a known prostate antigen.

The present invention also provides pharmaceutical compositions comprising one or more of the above polypeptides, or a DNA molecule encoding such polypeptides, and a physiologically acceptable carrier, together with vaccines comprising one or more of such polypeptide or DNA molecules in combination with a non-specific immune response enhancer.

In related aspects, pharmaceutical compositions for the treatment of prostate cancer comprising one or more polypeptides and a physiologically acceptable carrier are provided, wherein the polypeptide comprises an immunogenic portion of a prostate tumor protein or of a variant of said protein that differs only in conservative substitutions and/or modifications, the prostate tumor protein being encoded by a DNA molecule having a sequence selected from the group consisting of nucleotide sequences recited in SEQ ID NO: 5–7, 30–40, 46, 53, 66–69, 71, 72, 75–78, 80, 82–86, 88, 89, 91, 94–96, 98–102, 105, 106, 161–170, 179, 180, 182–187, 189, 190, 192, 195–197, 199–202, 205, 206, 208, 212–219, 221 and 226, the complements of said nucleotide sequences and sequences that hybridize to a sequence of SEQ ID NO: 5–7, 30–40, 46, 53, 66–69, 71, 72, 75–78, 80, 82–86, 88, 89, 91, 94–96, 98–102, 105, 106, 161–170, 179, 180, 182–187, 189, 190, 192, 195–197, 199–202, 205, 206, 208, 212–219, 221 or 226 under moderately stringent conditions. The invention also provides vaccines for the treatment of prostate cancer comprising such polypeptides in combination with a non-specific immune response enhancer, together with pharmaceutical compositions and vaccines comprising one or more DNA molecules having a sequence provided in SEQ ID NO: 5–7, 30–40, 46, 53, 66–69, 71, 72, 75–78, 80, 82–86, 88, 89, 91, 94–96, 98–102, 105, 106, 161–170, 179, 180, 182–187, 189, 190, 192, 195–197, 199–202, 205, 206, 208, 212–219, 221 and 226. Pharmaceutical compositions and vaccines comprising one or more of the above fusion proteins are also provided.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to compositions and methods for the immunotherapy of prostate cancer. The inventive compositions are generally polypeptides that comprise at least a portion of a prostate tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate tumor protein, or a variant of such a protein that differs only in conservative substitutions and/or modifications, wherein the prostate tumor protein includes an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111, 115–160, 181, 188, 191, 193, 194, 198, 203, 204, and 207–228, the complements of said nucleotide sequences and variants thereof. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate tumor protein is a portion that is capable of eliciting an immune response in a patient inflicted with prostate cancer and as such binds to antibodies present within sera from a prostate cancer patient. Such immunogenic portions generally comprise at least about 5 amino acid residues, more preferably at least about 10, and most preferably at least about 20 amino acid residues. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of prostate cancer patients. Methods for preparing and identifying immunogenic portions of antigens of known sequence are well known in the art and include those summarized in Paul, *Fundamental Immunology*, 3$^{rd}$ ed., Raven Press, 1993, pp. 243–247.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined by comparing sequences using computer algorithms well known to those of skill in the art, such as Megalign, using default parameters.

For prostate tumor polypeptides with immunoreactive properties, variants may, alternatively, be identified by modifying the amino acid sequence of one of the above polypeptides, and evaluating the immunoreactivity of the modified polypeptide. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (DNA, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign, using default parameters.

Such variant nucleotide sequences will generally hybridize to the recited nucleotide sequence under moderately stringent conditions. As used herein, "moderately stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

"Polypeptides" as used herein also include combination, or fusion, polypeptides. A "combination polypeptide" is a polypeptide comprising at least one of the above immunogenic portions and one or more additional immunogenic prostate tumor-specific sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

The prostate tumor proteins of the present invention, and DNA molecules encoding such proteins, may be isolated from prostate tumor tissue using any of a variety of methods well known in the art. DNA sequences corresponding to a gene (of a portion thereof) encoding one of the inventive prostate tumor proteins may be isolated from a prostate tumor cDNA library using a subtraction technique as described in detail below. Examples of such DNA sequences are provided in SEQ ID NOS: 1–107, 109–111, 115–171, 173–175, 177 and 179–228. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.,* 51:263, 1987; Erlich ed., PCR *Technology*, Stockton Press, NY, 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (DNA, 2:183, 1983).

The prostate tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. Coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known prostate antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene 40:39–46, 1985;* Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91 (1997)).

Polypeptides of the present invention that comprise an immunogenic portion of a prostate tumor protein may generally be used for immunotherapy of prostate cancer, wherein the polypeptide stimulates the patient's own immune response to prostate tumor cells. In further aspects, the present invention provides methods for using one or more of the immunoreactive polypeptides of the present invention (or fusion proteins comprising one or more such polypeptides and/or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or DNA molecules encoding such polypeptides) may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (e g., polylactic galactide) or a liposome (into which the polypeptide is incorporated). Pharmaceutical compositions and vaccines may also contain other epitopes of prostate tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS 86:317–321, 1989;* Flexner et al., *Ann. N.Y. Acad. Sci. 569:86–103, 1989;* Flexner et al., *Vaccine 8:17–21, 1990;* U.S. Pat. Nos. 4,603, 112, 4,769,330, and 5,017,487; W 89/01973; U.S. Pat. No. 4,777,127; GB 2,200,651; EP 0,345,242; WO 91/02805; Berkner, *Biotechniques 6:616–627, 1988;* Rosenfeld et al., *Science 252:431–434, 1991;* Kolls et al., *PNAS 91:215–219, 1994;* Kass-Eisler et al., *PNAS 90:11498–11502, 1993;* Guzman et al., *Circulation 88:2838–2848, 1993;* and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science 259:1691–1692, 1993.* The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention, such non-specific immune response enhancers being capable of eliciting or enhancing an immune response to an exogenous antigen. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis.* Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human prostate tumors. Binding agents of the present invention may generally be prepared using methods known to those of ordinary skill in the art, including the representative procedures described herein. Binding agents are capable of differentiating between patients with and without prostate cancer, using the representative assays described herein. In other words. antibodies or other binding agents raised against a prostate tumor protein, or a suitable portion thereof, will generate a signal indicating the presence of primary or metastatic prostate cancer in at least about 20% of patients afflicted with the disease, and will generate a negative signal indicating the absence of the disease in at least about 90% of individuals without primary or metastatic prostate cancer. Suitable portions of such prostate tumor proteins are portions that are able to generate a binding agent that indicates the presence of primary or metastatic prostate cancer in substantially all (i.e., at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be useful in assays for detecting primary or metastatic human prostate tumors. Polypeptide specific antibodies may be used alone or in combination to improve sensitivity.

Polypeptides capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies. A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptides complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al. *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast. prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A*

*Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Inmunol. 6:511–519, 1976*, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a prostate tumor protein of the present invention. The presence of the amplified cDNA is then detected using techniques well known in the art, such as gel electrophoresis. Similarly, oligonucleotide probes specific for a DNA molecule encoding a prostate tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 60%, preferably at least about 75% and more preferably at least about 90%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a sequence selected from SEQ ID NOS: 1–107, 109–111, 115–171, 173–175, 177 and 179–228. Preferably, oligonucleotide probes for use in the inventive diagnostic methods comprise at least about 15 contiguous oligonucleotides of a DNA molecule having a sequence provided in SEQ ID NOS: 1–107, 109–111, 115–171, 173–175, 177 and 179–228. Techniques for both PCR based assays and hybridization assays are well known in the art (see, for example, Mullis et al. Ibid; Ehrlich, Ibid). Primers or probes may thus be used to detect prostate tumor-specific sequences in biological samples, including blood, semen, prostate tissue and/or prostate tumor tissue.

The following Examples are offered by way of illustration and not by way of limitation.

EXAMPLES

Example 1

Isolation and Characterization of Prostate Tumor Polypeptides

This Example describes the isolation of prostate tumor polypeptides from a prostate tumor cDNA library.

A human prostate tumor cDNA expression library was constructed from prostate tumor poly A$^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly A$^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained 1.64×10$^7$ independent colonies, with 70% of clones having an insert and the average insert size being 1745 base pairs. The normal pancreas cDNA library contained 3.3×10$^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood, 84:189–199, 1994*) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of H$_2$O, heat-denatured and mixed with 100 μl (100 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl H$_2$O to form the driver DNA.

To form the tracer DNA, 10 μg prostate tumor cDNA library was digested with BamHI and XhoI, phenol chloroform extracted and passed through Chroma spin-400 columns (Clontech). Following ethanol precipitation, the tracer DNA was dissolved in 5 μl H$_2$O. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl H$^2$O, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pcCNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1–2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of poly A+ RNA from three prostate cancer patients, with a normal pancreas cDNA library (prostate subtraction 4) led to the identification of eight clones, referred to as 1D-4297, 1D-4309, 1D.1–4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1–4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined EDNA sequences for P509S and P510S are provided in SEQ ID NO: 223 and 224, respectively. Comparison of these sequences with those in the gene bank as described above, revealed some homology to previously identified ESTs.

Example 2

Determination of Tissue Specificity of Prostate Tumor Polypeptides

Using gene specific primers, mRNA expression levels for the representative prostate tumor polypeptides F1-16, H1-1, J1-17, L1-12, F1-12 and N1-1862 were examined in a variety of normal and tumor tissues using RT-PCR.

Briefly, total RNA was extracted from a variety of normal and tumor tissues using Trizol reagent as described above. First strand synthesis was carried out using 1–2 $\mu$g of total RNA with SuperScript II reverse transcriptase (BRL Life Technologies) at 42° C. for one hour. The cDNA was then amplified by PCR with gene-specific primers. To ensure the semi-quantitative nature of the RT-PCR, $\beta$-actin was used as an internal control for each of the tissues examined. First, serial dilutions of the first strand cDNAs were prepared and RT-PCR assays were performed using $\beta$-actin specific primers. A dilution was then chosen that enabled the linear range amplification of the $\beta$-actin template and which was sensitive enough to reflect the differences in the initial copy numbers. Using these conditions, the $\beta$-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 is over-expressed in prostate tumors and normal prostate, while being undetectable in other normal tissues tested. J1-17 was detected in two prostate tumors and not in the other tissues tested. N1-1862 was found to be over-expressed in three prostate tumors and to be expressed in normal prostate, colon and kidney, but not in other tissues tested. F1-12 was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 was found to be over-expressed in normal prostate and prostate tumor, with some expression being detected in normal skeletal muscle. Both J1-12 and F1-12 were found to be over-expressed in prostate tumor, with expression being lower or undetectable in all other tissues tested. N1-1862 was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-I Blue MRF' E. coli (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA Expression levels for these clones were determined using the micro-array technology described above. The clones 7-G6, 8-G3, 8-B5, 8-B6, 8-D4, 8-D9, 9-F3, 9-f12, 9-H3, 10-A2, 10-A4, 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB 13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

Example 4

Synthesis of Polypeptides

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated DNA molecule comprising SEQ ID NO:225.
2. An expression vector comprising the DNA molecule of claim 1.
3. An isolated DNA molecule consisting of SEQ ID NO:10.
4. An isolated DNA molecule consisting of at least 15 contiguous residues of SEQ ID NO:10.
5. An expression vector comprising the DNA molecule of any one of claims 3 or 4.
6. An isolated DNA molecule consisting of SEQ ID NO:11.
7. An isolated DNA molecule consisting of at least 40 contiguous residues of SEQ ID NO:11.
8. An expression vector comprising the DNA molecule of any one of claims 6 or 7.
9. A host cell transformed with an expression vector according to any one of claim 2, 5 and 8.
10. The host cell of claim 9 wherein the host cell is selected from the group consisting of E. coli, yeast, and mammalian cells.

* * * * *

SEQUENCE LISTING

<160> NUMBER OF SEQ ID NOS: 228

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
tttttttttt tttttcacag tataacagct ctttatttct gtgagttcta ctaggaaatc      60
atcaaatctg agggttgtct ggaggacttc aatacacctc ccccatagt gaatcagctt      120 ccaggggtc cagtccctct ccttacttca tccccatccc atgccaaagg aagaccctcc      180
ctccttggct cacagccttc tctaggcttc ccagtgcctc caggacagag tgggttatgt      240
tttcagctcc atccttgctg tgagtgtctg gtgcgttgtg cctccagctt ctgctcagtg      300
cttcatggac agtgtccagc acatgtcact ctccactctc tcagtgtgga tccactagtt      360
ctagagcggc cgccaccgcg gtggagctcc agcttttgtt cctttagtg agggttaatt     420 gcgcgcttgg cgtaatcatg gtcataactg tttcctgtgt gaaattgtta tccgctcaca      480
attccacaca acatacgagc cggaagcata agtgtaaag cctggggtgc ctaatgagtg      540
anctaactca cattaattgc gttgcgctca ctgnccgctt tccagtcngg aaaactgtcg      600
tgccagctgc attaatgaat cggccaacgc ncggggaaaa gcggtttgcg ttttgggggc      660
tcttccgctt ctcgctcact nantcctgcg ctcggtcntt cggctgcggg gaacggtatc      720
actcctcaaa ggnggtatta cggttatccn naaatcnggg gatacccngg aaaaaantt     780 aacaaaaggg cancaaaggg cngaaacgta aaaa                                 814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

```
acagaaatgt tggatggtgg agcacctttc tatacgactt acaggacagc agatggggaa      60
ttcatggctg ttggagcaat agaacccag ttctacgagc tgctgatcaa aggacttgga      120
ctaaagtctg atgaacttcc caatcagatg agcatggatg attggccaga aatgaagaag      180
aagtttgcag atgtatttgc aaagaagacg aaggcagagt ggtgtcaaat ctttgacggc      240
```

```
acagatgcct gtgtgactcc ggttctgact tttgaggagg ttgttcatca tgatcacaac      300
aaggaacggg gctcgtttat caccagtgag gagcaggacg tgagccccg ccctgcacct       360 ctgctgttaa acaccccagc catcccttct ttcaaaaggg atccactagt tctagaagcg      420
gccgccaccg cggtggagct ccagcttttg ttccctttag tgagggttaa ttgcgcgctt      480
ggcgtaatca tggtcatagc tgtttcctgt gtgaaattgt tatccgctca caattccccc      540
aacatacgag ccggaacata aagtgttaag cctggggtgc ctaatgantg agctaactcn      600
cattaattgc gttgcgctca ctgcccgctt ccagtcggg aaaactgtcg tgccactgcn       660
ttantgaatc ngccaccccc cgggaaaagg cggttgcntt tgggcctct ccgctttcc        720 tcgctcattg atcctngcnc ccggtcttcg gctgcggnga acggttcact cctcaaaggc      780
ggtntnccgg ttatccccaa acnggggata cccnga                                816

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3
cttttgaaag aagggatggc tggggtgttt aacagcagag gtgcagggcg ggggctcacg      60
tcctgctcct cactggtgat aaacgagccc cgttccttgt tgtgatcatg atgaacaacc     120
tcctcaaaag tcagaaccgg agtcacacag gcatctgtgc cgtcaaagat ttgacaccac     180
tctgccttcg tcttctttgc aaatacatct gcaaacttct tcttcatttc tggccaatca    240
tccatgctca tctgattggg aagttcatca gactttagtc canntccttt gatcagcagc    300
tcgtagaact ggggttctat tgctccaaca gccatgaatt ccccatctgc tgtcctgtaa    360
gtcgtataga aaggtgctcc accatccaac atgttctgtc ctcgaggggg ggcccggtac    420
ccaattcgcc ctatantgag tcgtattacg cgcgctcact ggccgtcgtt ttacaacgtc    480
gtgactggga aaccctggg cgttaccaac ttaatcgcct tgcagcacat ccccctttcg    540
ccagctgggt gtaatancga aaaggcccgc accgatcgcc cttccaacag ttgcgcacct    600
gaatgggnaa atgggacccc cctgttaccg cgcattnaac ccccgcnggg tttngttgtt    660 accccacnt nnaccgctta cactttgcca gcgccttanc gcccgctccc tttcnccttt    720
cttcccttcc tttcncnccn ctttccccg gggtttcccc cntcaaaccc cna             773

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4
cctcctgagt cctactgacc tgtgctttct ggtgtggagt ccagggctgc taggaaaagg      60
aatgggcaga cacaggtgta tgccaatgtt tctgaaatgg gtataatttc gtcctctcct    120
tcggaacact ggctgtctct gaagacttct cgctcagttt cagtgaggac acacacaaag    180
acgtgggtga ccatgttgtt tgtggggtgc agagatggga gggtggggc ccaccctgga    240 agagtggaca gtgacacaag gtggacactc tctacagatc actgaggata agctggagcc    300
```

-continued

```
acaatgcatg aggcacacac acagcaagga tgacnctgta aacatagccc acgctgtcct      360
gngggcactg ggaagcctan atnaggccgt gagcanaaag aaggggagga tccactagtt      420
ctanagcggc cgccaccgcg gtgganctcc anctttttgtt cccttttagtg agggttaatt    480 gcgcgcttgg cntaatcatg gtcatanctn tttcctgtgt gaaattgtta tccgctcaca      540
attccacaca acatacganc cggaaacata aantgtaaac ctgggggtgcc taatgantga     600 ctaactcaca ttaattgcgt tgcgctcact gcccgctttc caatcnggaa acctgtcttg     660
ccncttgcat tnatgaatcn gccaaccccc ggggaaaagc gtttgcgttt tgggcgctct      720
tccgcttcct cnctcantta ntccctncnc tcggtcattc cggctgcngc aaaccggttc      780
accncctcca aaggggggtat tccggttttcc ccnaatccgg gganancc                 828
```

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

```
tttttttttt ttttactga tagatggaat ttattaagct tttcacatgt gatagcacat       60
agttttaatt gcatccaaag tactaacaaa aactctagca atcaagaatg cagcatgtt      120 attttataac aatcaacacc tgtggctttt aaaatttggt tttcataaga taatttatac    180
tgaagtaaat ctagccatgc ttttaaaaaa tgctttaggt cactccaagc ttggcagtta    240
acatttggca taaacaataa taaaacaatc acaatttaat aaataacaaa tacaacattg    300
taggccataa tcatatacag tataaggaaa aggtggtagt gttgagtaag cagttattag    360
aatagaatac cttggcctct atgcaaatat gtctagacac tttgattcac tcagccctga    420
cattcagttt tcaaagtagg agacaggttc tacagtatca ttttacagtt tccaacacat    480
tgaaaacaag tagaaaatga tgagttgatt tttattaatg cattacatcc tcaagagtta    540
tcaccaaccc ctcagttata aaaaattttc aagttatatt agtcatataa cttggtgtgc    600 ttatttttaaa ttagtgctaa atggattaag tgaagacaac aatggtcccc taatgtgatt    660
gatattggtc attttttacca gcttctaaat ctnaactttc aggcttttga actggaacat    720
tgnatnacag tgttccanag ttncaaccta ctggaacatt acagtgtgct tgattcaaaa    780
tgttattttg ttaaaaatta aattttaacc tggtggaaaa ataatttgaa atna         834
```

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

```
tttttttttt tttttttttt aagaccctca tcaatagatg gagacataca gaaatagtca       60
aaccacatct acaaaatgcc agtatcaggc ggcggcttcg aagccaaagt gatgtttgga     120
tgtaaagtga aatattagtt ggcggatgaa gcagatagtg aggaaagttg agccaataat    180
gacgtgaagt ccgtggaagc ctgtggctac aaaaaatgtt gagccgtaga tgccgtcgga    240
aatggtgaag ggagactcga agtactctga ggcttgtagg agggtaaaat agagacccag    300
```

| | |
|---|---|
| taaaattgta ataagcagtg cttgaattat ttggtttcgg ttgttttcta ttagactatg | 360 |
| gtgagctcag gtgattgata ctcctgatgc gagtaatacg gatgtgttta ggagtgggac | 420 |
| ttctagggga tttagcgggg tgatgcctgt tgggggccag tgccctccta gttgggggt | 480 |
| aggggctagg ctggagtggt aaaaggctca gaaaaatcct gcgaagaaaa aaacttctga | 540 |
| ggtaataaat aggattatcc cgtatcgaag gccttttgg acaggtggtg tgtggtggcc | 600 |
| ttggtatgtg ctttctcgtg ttacatcgcg ccatcattgg tatatggtta gtgtgttggg | 660 |
| ttantanggc ctantatgaa gaactttggg antggaatta aatcaatngc ttggccggaa | 720 |
| gtcattanga nggctnaaaa ggccctgtta ngggtctggg ctnggtttta cccnacccat | 780 |
| ggaatncncc ccccggacna ntgnatccct attcttaa | 818 |

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7

| | |
|---|---|
| ttttttttt ttttttttt tggctctaga gggggtagag ggggtgctat agggtaaata | 60 |
| cgggccctat ttcaaagatt tttaggggaa ttaattctag gacgatgggt atgaaactgt | 120 |
| ggtttgctcc acagatttca gagcattgac cgtagtatac ccccggtcgt gtagcggtga | 180 |
| aagtggtttg gtttagacgt ccgggaattg catctgtttt taagcctaat gtggggacag | 240 |
| ctcatgagtg caagacgtct tgtgatgtaa ttattatacn aatgggggct tcaatcggga | 300 |
| gtactactcg attgtcaacg tcaaggagtc gcaggtcgcc tggttctagg aataatgggg | 360 |
| gaagtatgta ggaattgaag attaatccgc cgtagtcggt gttctcctag gttcaatacc | 420 |
| attggtggcc aattgatttg atggtaaggg gagggatcgt tgaactcgtc tgttatgtaa | 480 |
| aggatnccctt ngggatggga aggcnataa ggactangga tnaatggcgg gcangatatt | 540 |
| tcaaacngtc tctanttcct gaaacgtctg aaatgttaat aanaattaan tttngttatt | 600 |
| gaatnttnng gaaagggct tacaggacta gaaaccaaat angaaaanta atnntaangg | 660 |
| cnttatcntn aaaggtnata accnctccta tnatcccacc caatngnatt ccccacncnn | 720 |
| acnattggat ncccanttc canaaanggc cnccccccgg tgnanncnc cttttgttcc | 780 |
| cttnantgan ggttattcnc ccctngcntt atcancc | 817 |

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8

| | |
|---|---|
| catttccggg tttactttct aaggaaagcc gagcggaagc tgctaacgtg ggaatcggtg | 60 |
| cataaggaga actttctgct ggcacgcgct agggacaag gggagagcga ctccgagcgt | 120 |
| ctgaagcgca cgtcccagaa ggtggacttg gcactgaaac agctgggaca catccgcgag | 180 |
| tacgaacagc gcctgaaagt gctggagcgg gaggtccagc agtgtagccg cgtcctgggg | 240 |
| tgggtggccg angcctganc cgctctgcct tgctgccccc angtgggccg ccaccccctg | 300 |

-continued

```
acctgcctgg gtccaaacac tgagccctgc tggcggactt caagganaac ccccacangg      360
ggattttgct cctanantaa ggctcatctg ggcctcggcc ccccacctg gttggccttg       420 tctttgangt gagccccatg tccatctggg ccactgtcng gaccacctt ngggagtgtt       480 ctccttacaa ccacannatg cccggctcct cccggaaacc antcccancc tgngaaggat     540
caagncctgn atccactnnt nctanaaccg gccnccncg cngtggaacc cnccttntgt      600
tccttttcnt tnagggttaa tnncgccttg gccttnccan ngtcctncnc nttttccnnt    660
gttnaaattg ttangcnccc nccnntcccn cnncnnncnan cccgacccnn annttnnann   720
ncctgggggt nccnncngat tgacccnncc nccctntant tgcnttnggg nncnntgccc    780
ctttccctct ngggannCg                                                   799
```

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

```
acgccttgat cctcccaggc tgggactggt tctgggagga gccgggcatg ctgtggtttg      60
taangatgac actcccaaag gtggtcctga cagtggccca gatggacatg gggctcacct     120
caaggacaag gccaccaggt gcgggggccg aagcccacat gatccttact ctatgagcaa     180
aatcccctgt gggggcttct ccttgaagtc cgccancagg gctcagtctt tggacccang     240
caggtcatgg ggttgtngnc caactgggg ccncaacgca aaanggcnca gggcctcngn      300
cacccatccc angacgcggc tacactnctg gacctcccnc tccaccactt tcatgcgctg    360
ttcntacccg cgnatntgtc ccanctgttt cngtgccnac tccancttct nggacgtgcg    420
ctacatacgc ccggantcnc nctcccgctt tgtccctatc cacgtnccan caacaaattt    480
cnccntantg caccnattcc cacntttnnc agntttccnc nncgngcttc ctttaaaag     540 ggttganccc cggaaaatnc cccaaggggg gggggccngg tacccaactn ccccctnata    600
gctgaantcc ccatnaccnn gnctcnatgg ancntccnt tttaannacn ttctnaactt     660
gggaananCC ctcgncCntn ccCCCnttaa tccCnccttg cnangnncnt CCCCCnntcC    720
ncccnnntng gcntntnann cnaaaaaggc ccnnnancaa tctcctnncn cctcanttcg    780
ccanccctcg aaatcggccn c                                                801
```

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

```
cagtctatnt ggccagtgtg cagctttcc ctgtggctgc cggtgccaca tgcctgtccc       60
acagtgtggc cgtggtgaca gcttcagccg ccctcaccgg gttcaccttc tcagccctgc    120
agatcctgcc ctacacactg gcctccctct accaccggga gaagcaggtg ttcctgccca    180
aataccgagg ggacactgga ggtgctagca gtgaggacag cctgatgacc agcttcctgc    240
caggccctaa gcctggagct cccttcccta atggacacgt gggtgctgga ggcagtggcc    300
tgctcccacc tccacccgcg ctctgcgggg cctctgcctg tgatgtctcc gtacgtgtgg   360
```

```
tggtgggtga gcccaccgan gccagggtgg ttccggccg ggcatctgc ctggacctcg      420 ccatcctgga tagtgcttcc tgctgtccca ngtggcccca tccctgttta tgggctccat      480
tgtccagctc agccagtctg tcactgccta tatggtgtct gccgcaggcc tgggtctggt      540
cccatttact ttgctacaca ggtantattt gacaagaacg anttggccaa atactcagcg      600
ttaaaaaatt ccagcaacat tggggtgga aggcctgcct cactgggtcc aactccccgc      660
tcctgttaac cccatggggc tgccggcttg ccgccaatt tctgttgctg ccaaantnat      720
gtggctctct gctgccacct gttgctggct aagtgcnta cngcncanct nggggggtng      780 ggngttccc                                                             789
```

```
<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11
cccaccctac ccaaatatta gacaccaaca cagaaaagct agcaatggat tcccttctac       60
tttgttaaat aaataagtta aatatttaaa tgcctgtgtc tctgtgatgg caacagaagg      120
accaacaggc cacatcctga taaaggtaa gaggggggtg gatcagcaaa agacagtgc       180 tgtgggctga ggggacctgg ttcttgtgtg ttgcccctca ggactcttcc cctacaaata      240
actttcatat gttcaaatcc catggaggag tgtttcatcc tagaaactcc catgcaagag      300
ctacattaaa cgaagctgca ggttaagggg cttanagatg ggaaaccagg tgactgagtt      360
tattcagctc ccaaaaaccc ttctctaggt gtgtctcaac taggaggcta gctgttaacc      420
ctgagcctgg gtaatccacc tgcagagtcc ccgcattcca gtgcatggaa cccttctggc      480
ctccctgtat aagtccagac tgaaaccccc ttggaaggnc tccagtcagg cagccctana      540
aactggggaa aaagaaaag gacgccccan cccccagctg tgcanctacg cacctcaaca      600
gcacagggtg gcagcaaaaa aaccacttta ctttggcaca aacaaaaact ngggggggca      660
accccggcac cccnangggg gttaacagga ancngggnaa cntggaaccc aattnaggca      720
ggcccnccac cccnaatntt gctgggaaat ttttcctccc ctaaattntt tc             772
```

```
<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12
gccccaattc cagctgccac accacccacg gtgactgcat tagttcggat gtcatacaaa       60
agctgattga agcaaccctc tacttttttgg tcgtgagcct tttgcttggt gcaggtttca     120
ttggctgtgt tggtgacgtt gtcattgcaa cagaatgggg gaaaggcact gttctctttg     180
aagtanggtg agtcctcaaa atccgtatag ttggtgaagc cacagcactt gagcccttc      240 atggtggtgt tccacacttg agtgaagtct tcctgggaac cataatcttt cttgatggca     300
ggcactacca gcaacgtcag ggaagtgctc agccattgtg gtgtacacca aggcgaccac     360
agcagctgcn acctcagcaa tgaagatgan gaggangatg aagaagaacg tcncgagggc     420
```

```
acacttgctc tcagtcttan caccatanca gcccntgaaa accaananca aagaccacna      480
cnccggctgc gatgaagaaa tnaccccncg ttgacaaact tgcatggcac tgggancccac     540 agtggcccna aaaatcttca aaaggatgc cccatcnatt gacccccaa atgcccactg        600 ccaacagggg ctgccccacn cncnnaacga tganccnatt gnacaagatc tncntggtct     660
tnatnaacnt gaaccctgcn tngtggctcc tgttcaggnc cnnggcctga cttctnaann    720
aangaactcn gaagncccca cnggananc g                                      751
```

<210> SEQ ID NO 13
<211> LENGTH: 29
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13

```
gagccaggcg tccctctgcc tgccactca gtggcaacac ccgggagctg ttttgtcctt       60
tgtggancct cagcagtncc ctctttcaga actcantgcc aagancctg aacaggagcc      120 accatgcagt gcttcagctt cattaagacc atgatgatcc tcttcaattt gctcatcttt     180
ctgtgtggtg cagccctgtt ggcagtgggc atctgggtgt caatcgatgg ggcatccttt    240
ctgaagatct tcgggccact gtcgtccagt gccatgcagt ttgtcaacgt gggctacttc    300
ctcatcgcag ccggcgttgt ggtcttagct ctaggtttcc tgggctgcta tggtgctaag    360
actgagagca agtgtgccct cgtgacgttc ttcttcatcc tcctcctcat cttcattgct     420
gaggttgcaa tgctgtggtc gccttggtgt acaccacaat ggctgagcac ttcctgacgt    480
tgctggtaat gcctgccatc aanaaaagat tatgggttcc caggaanact tcactcaagt     540
gttggaacac caccatgaaa gggctcaagt gctgtggctt cnnccaacta tacggatttt    600
gaagantcac ctacttcaaa gaaaanagtg cctttccccc atttctgttg caattgacaa    660
acgtccccaa cacagccaat tgaaaacctg cacccaaccc aaangggtcc ccaaccanaa    720 attnaaggg                                                             729
```

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14

```
tgctcttcct caaagttgtt cttgttgcca taacaaccac cataggtaaa gcgggcgcag      60
tgttcgctga aggggttgta gtaccagcgc gggatgctct ccttgcagag tcctgtgtct    120
ggcaggtcca cgcagtgccc tttgtcactg gggaaatgga tgcgctggag ctcgtcaaag    180
ccactcgtgt atttttcaca ggcagcctcg tccgacgcgt cggggcagtt gggggtgtct    240
tcacactcca ggaaactgtc natgcagcag ccattgctgc agcggaactg ggtgggctga    300
cangtgccag agcacactgg atggcgcctt tccatgnnan gggccctgng ggaaagtccc   360
tganccccan anctgcctct caaangcccc accttgcaca cccgacagg ctagaatgga    420 atcttcttcc cgaaaggtag ttnttcttgt tgcccaancc ancccntaa acaaactctt    480
```

```
gcanatctgc tccgnggggg tcntantacc ancgtgggaa agaacccca ggcngcgaac    540 caancttgtt tggatncgaa gcnataatct nctnttctgc ttggtggaca gcaccantna   600
ctgtnnanct ttagnccntg gtcctcntgg gttgnncttg aacctaatcn ccnntcaact   660
gggacaaggt aantngcent cctttnaatt cccnancntn cccctggtt tggggttttn    720 cncnctccta cccagaaan nccgtgttcc cccccaacta ggggccnaaa ccnttnttc     780 cacaaccctn ccccacccac gggttcngnt ggttng                             816

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15
ccaaggcctg ggcaggcata nacttgaagg tacaaccca ggaacccctg gtgctgaagg     60
atgtggaaaa cacagattgg cgcctactgc ggggtgacac ggatgtcagg gtagagagga   120
aagacccaaa ccaggtggaa ctgtggggac tcaaggaang cacctacctg ttccagctga   180
cagtgactag ctcagaccac ccagaggaca cggccaacgt cacagtcact gtgctgtcca   240
ccaagcagac agaagactac tgcctcgcat ccaacaangt gggtcgctgc cggggctctt   300
tcccacgctg gtactatgac cccacggagc agatctgcaa gagtttcgtt tatggaggct   360
gcttgggcaa caagaacaac taccttcggg aagaagagtg cattctancc tgtcngggtg   420
tgcaaggtgg gcctttgana ngcanctctg ggctcangc gactttcccc cagggcccct    480
ccatggaaag gcgccatcca ntgttctctg gcacctgtca gcccacccag ttccgctgca   540
ncaatggctg ctgcatcnac antttcctng aattgtgaca acaccccca ntgccccaa     600 ccctcccaac aaagcttccc tgttnaaaaa tacnccantt ggcttttnac aaacnccgg    660 cnccctccntt ttccccnntn aacaaagggc nctngcnttt gaactgcccn aacccngaa   720 tctnccnngg aaaaantncc cccctggtt cctnnaancc cctccncnaa anctncccc    780 ccc                                                                783

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16
gccccaattc cagctgccac accacccacg gtgactgcat tagttcggat gtcatacaaa    60
agctgattga agcaaccctc tactttttgg tcgtgagcct tttgcttggt gcaggtttca   120
ttggctgtgt tggtgacgtt gtcattgcaa cagaatgggg gaaaggcact gttctctttg   180
aagtagggtg agtcctcaaa atccgtatag ttggtgaagc cacagcactt gagcccttc    240 atggtggtgt tccacacttg agtgaagtct tcctgggaac cataatcttt cttgatggca   300
ggcactacca gcaacgtcag gaagtgctca gccattgtgg tgtacaccaa ggcgaccaca   360
gcagctgcaa cctcagcaat gaagatgagg aggaggatga agaagaacgt cncgagggca   420
cacttgctct ccgtcttagc accatagcag cccangaaac caagagcaaa gaccacaacg   480
```
ccngctgcga atgaaagaaa ntacccacgt tgacaaactg catggccact ggacgacagt      540
tggcccgaan atcttcagaa aagggatgcc ccatcgattg aacacccana tgcccactgc      600
cnacagggct gcnccncncn gaaagaatga gccattgaag aaggatcntc ntggtcttaa      660
tgaactgaaa ccntgcatgg tggcccctgt tcagggctct tggcagtgaa ttctganaaa      720
aaggaacngc ntnagccccc ccaaangana aaacaccccc gggtgttgcc ctgaattggc      780
ggccaaggan ccctgccccn g                                                801

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17
gtgagagcca ggcgtccctc tgcctgccca ctcagtggca acacccggga gctgttttgt       60
cctttgtgga gcctcagcag ttccctcttt cagaactcac tgccaagagc cctgaacagg      120
agccaccatg cagtgcttca gcttcattaa gaccatgatg atcctcttca atttgctcat      180 cttttctgtgt ggtgcagccc tgttggcagt gggcatctgg gtgtcaatcg atgggcatc      240 ctttctgaag atcttcgggc cactgtcgtc cagtgccatg cagtttgtca cgtgggcta      300 cttcctcatc gcagccggcg ttgtggtctt tgctcttggt ttcctgggct gctatggtgc      360
taagacggag agcaagtgtg ccctcgtgac gttcttcttc atcctcctcc tcatcttcat      420
tgctgaagtt gcagctgctg tggtcgcctt ggtgtacacc acaatggctg aaccattcct      480
gacgttgctg gtantgcctg ccatcaanaa agattatggg ttcccaggaa aaattcactc      540
aantntggaa caccnccatg aaaagggctc caatttctgn tggcttcccc aactataccg      600
gaattttgaa agantcnccc tacttccaaa aaaaaanant tgcctttncc cccnttctgt      660
tgcaatgaaa acntcccaan acngccaatn aaaacctgcc cnnncaaaaa ggntcncaaa      720
caaaaaaant nnaagggttn                                                  740

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18
ccgctggttg cgctggtcca gngnagccac gaagcacgtc agcatacaca gcctcaatca       60
caaggtcttc cagctgccgc acattacgca gggcaagagc ctccagcaac actgcatatg      120
ggatacactt tactttagca gccagggtga caactgagag gtgtcgaagc ttattcttct      180
gagcctctgt tagtggagga agattccggg cttcagctaa gtagtcagcg tatgtcccat      240
aagcaaacac tgtgagcagc cggaaggtag aggcaaagtc actctcagcc agctctctaa      300
cattgggcat gtccagcagt tctccaaaca cgtagacacc agnggcctcc agcacctgat      360
ggatgagtgt ggccagcgct gccccttgg ccgacttggc taggagcaga aattgctcct      420
ggttctgccc tgtcaccttc acttccgcac tcatcactgc actgagtgtg ggggacttgg      480

```
gctcaggatg tccagagacg tggttccgcc ccctcnctta atgacaccgn ccanncaacc    540
gtcggctccc gccgantgng ttcgtcgtnc ctgggtcagg gtctgctggc cnctacttgc    600
aancttcgtc nggcccatgg aattcaccnc accggaactn gtangatcca ctnnttctat    660
aaccggncgc caccgcnnnt ggaactccac tcttnttncc tttacttgag ggttaaggtc    720
acccttnncg ttaccttggt ccaaaccntn ccntgtgtcg anatngtnaa tcnggnccna    780
tnccanccnc atangaagcc ng                                            802

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19
cnaagcttcc aggtnacggg ccgcnaancc tgacccnagg tancanaang cagncgcgg     60 gagcccaccg tcacgnggng gngtctttat nggagggggc ggagccacat cnctggacnt   120
cntgacccca actcccncc ncncantgca gtgatgagtg cagaactgaa ggtnacgtgg    180
caggaaccaa gancaaannc tgctccnntc caagtcggcn naggggcgg ggctggccac    240 gcncatccnt cnagtgctgn aaagccccnn cctgtctact tgtttggaga acngcnnnga  300
catgcccagn gttanataac nggcngagag tnantttgcc tctcccttcc ggctgcgcan   360
cgngtntgct tagnggacat aacctgacta cttaactgaa cccnngaatc tnccncccct   420
ccactaagct cagaacaaaa aacttcgaca ccactcantt gtcacctgnc tgctcaagta   480
aagtgtaccc catncccaat gtntgctnga ngctctgncc tgcnttangt tcggtcctgg   540
gaagacctat caattnaagc tatgtttctg actgcctctt gctccctgna acaancnacc   600
cnncnntcca aggggggnc ggccccaat cccccaacc ntnaattnan tttancccn      660 cccccnggcc cggcctttta cnancntcnn nnacngggna aaaccnnngc tttncccaac   720
nnaatccncc t                                                       731

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20
tttttttttt tttttttttt taaaaacccc ctccattnaa tgnaaacttc cgaaattgtc    60 caacccctc ntccaaatnn ccntttccgg gnggggttc caaacccaan ttanntttgg    120
annttaaatt aaatnttnnt tggnggnnna anccnaatgt nangaaagtt naacccanta   180
tnancttnaa tncctggaaa ccngtngntt ccaaaaatnt ttaaccctta antccctccg   240
aaatngttna nggaaaaccc aanttctcnt aaggttgttt gaaggntnaa tnaaaancccc  300 nnccaattgt ttttngccac gcctgaatta attggnttcc gntgttttcc nttaaaanaa   360 ggnnanccccc ggttantnaa tccccccnnc cccaattata ccganttttt ttngaattgg   420 ganccncgg gaattaacgg ggnnnntccc tnttggggg cngnnccccc cccntcgggg    480
ggttngggnc aggncnnaat tgtttaaggg tccgaaaaat ccctccnaga aaaaaanctc    540
```

| | | |
|---|---|---|
| ccaggntgag nntngggttt ncccccccc canggcccct ctcgnanagt tgggttttgg | 600 |
| ggggcctggg attttntttc ccctnttncc tcccccccc ccngggananag aggttngngt | 660 |
| tttgntcnnc ggcccncan aaganctttn ccganttnan ttaaatccnt gcctnggcga | 720 |
| agtccnttgn agggntaaan ggccccctnn cggg | 754 |

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

| | | |
|---|---|---|
| atcancccat gacccnaac nngggaccnc tcanccggnc nnncnaccnc cggccnatca | 60 |
| nngtnagnnc actncnnttn natcacnccc cnccnactac gcccncnanc cnacgcncta | 120 |
| nncanatncc actganngcg cgangtngan ngagaaanct nataccanag ncaccanacn | 180 |
| ccagctgtcc nanaangcct nnnatacngg nnnatccaat ntgnaccctc cnaagtattn | 240 |
| nncnncanat gattttcctn anccgattac ccntnccccc tanccctcc ccccaacna | 300 |
| cgaaggcnct ggnccaagg nngcgncncc ccgctagntc cccnncaagt cncncncta | 360 |
| aactcanccn nattacncgc ttcntgagta tcactccccg aatctcaccc tactcaactc | 420 |
| aaaaanatcn gatacaaaat aatncaagcc tgnttatnac actntgactg ggtctctatt | 480 |
| ttagnggtcc ntnaancntc ctaatacttc cagtctncct tcnccaattt ccnaanggct | 540 |
| ctttcngaca gcatnttttg gttcccnntt gggttcttan ngaattgccc ttcntngaac | 600 |
| gggctcntct tttccttcgg ttanccctggn ttcnnccggc cagttattat ttcccntttt | 660 |
| aaattcntnc cntttantt tggcnttcna accccccggc cttgaaaacg gccccctggt | 720 |
| aaaaggttgt tttganaaaa tttttgtttt gttcc | 755 |

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

| | | |
|---|---|---|
| tttttttttt tttttangtg tngtcgtgca ggtagaggct tactacaant gtgaanacgt | 60 |
| acgctnggan taangcgacc cganttctag gannncccct aaaatcanac tgtgaagatn | 120 |
| atcctgnnna cggaanggtc accggnngat nntgctaggg tgnccnctcc cannncnttn | 180 |
| cataactcng nggccctgcc caccaccttc ggcggcccng ngnccgggcc cgggtcattn | 240 |
| gnnttaaccn cactnngcna ncggtttccn nccccnncg acccnggcga tccggggtnc | 300 |
| tctgtcttcc cctgnagncn anaaantggg ccncggnccc ctttaccct nnacaagcca | 360 |
| cngccntcta nccncngccc ccctccant nnggggact gccnanngct ccgttnctng | 420 |
| nnaccccnnn gggtncctcg gttgtcgant cnaccgnang ccanggattc cnaaggaagg | 480 |
| tgcgttnttg gccctaccc ttcgctncgg nncaccttc ccgacnanga nccgctcccg | 540 |
| cncnncgnng cctcncctcg caacaccgc nctcntcngt ncggnnnccc ccccaccccgc | 600 |
| ncccctcncnc ngncgnancn ctccnccncc gtctcannca ccaccccgcc ccgccaggcc | 660 |

| | |
|---|---:|
| ntcanccacn ggnngacnng nagcncnntc gcnccgcgcn gcgncccct cgccncngaa | 720 |
| ctncntcngg ccantnncgc tcaanccnna cnaaacgccg ctgcgcggcc cgnagcgncc | 780 |
| ncctcncga gtcctcccgn cttccnaccc angnnttccn cgaggacacn nnaccccgcc | 840 |
| nncangcgg | 849 |

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

| | |
|---|---:|
| gcgcaaacta tacttcgctc gnactcgtgc gcctcgctnc tcttttcctc cgcaaccatg | 60 |
| tctgacnanc ccgattnggc ngatatcnan aagntcganc agtccaaact gantaacaca | 120 |
| cacacncnan aganaaatcc nctgccttcc anagtanacn attgaacnng agaaccangc | 180 |
| nggcgaatcg taatnaggcg tgcgccgcca atntgtcncc gtttattntn ccagcntcnc | 240 |
| ctnccnaccc tacntcttcn nagctgtcnn accoctngtn cgaccccccc naggtcggga | 300 |
| tcgggttnn nntgaccgng cnnccoctcc cccontccat nacgancon ccgcaccacc | 360 |
| nanngccgc ncoccgnnct cttcgccncc ctgtcctntn ccoctgtgc ctggcncngn | 420 |
| accgcattga coctcgccnn ctncnngaaa ncgnanacgt ccggttgnn annancgctg | 480 |
| tgggnnngcg tctgcnccgc gttccttccn ncnncttcca ccatcttcnt tacngggtct | 540 |
| ccncgccntc tcnnncacnc cctgggacgc tntcctntgc ccoccttnac tcococcctt | 600 |
| cgncgtgncc cgnccocacc ntcatttnca nacgntcttc acaannncct ggntnnctcc | 660 |
| cnancngncn gtcanccnag ggaaggnngg ggnnccnntg nttgacgttg nggngangtc | 720 |
| cgaanantcc tcnccntcan cnctaccoct cgggcgnnct ctcngttncc aacttancaa | 780 |
| ntctcccccg ngngcncntc tcagcctcnc ccncccncnt ctctgcantg tnctctgctc | 840 |
| tnaccnntac gantnttcgn cnccctcttt cc | 872 |

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

| | |
|---|---:|
| gcatgcaagc ttgagtattc tatagngtca cctaaatanc ttggcntaat catggtcnta | 60 |
| nctgncttcc tgtgtcaaat gtatacnaan tanatatgaa tctnatntga caagannngta | 120 |
| tcntncatta gtaacaantg tnntgtccat cctgtcngan canattccca tnnattncgn | 180 |
| cgcattcncn gcncantatn taatngggaa ntcnnntnnn ncaccnncat ctatcntncc | 240 |
| gcnccctgac tggnagagat ggatnanttc tnntntgacc nacatgttca tcttggattn | 300 |
| aanaccccc cgcngnccac cggttngnng cnagccnntc ccaagacctc ctgtggaggt | 360 |
| aacctgcgtc aganncatca aacntgggaa acccgcnncc angtnnaagt ngnnncanan | 420 |
| gatcccgtcc aggnttnacc atcccttcnc agcgcccct ttngtgcctt anagngnagc | 480 |

| | |
|---|---|
| gtgtccnanc cnctcaacat ganacgcgcc agnccanccg caattnggca caatgtcgnc | 540 |
| gaaccccta ggggganta tncaaanccc caggattgtc cncncangaa atcccncanc | 600 |
| ccncccctac ccnncctttgg gacngtgacc aantcccgga gtnccagtcc ggccngnctc | 660 |
| ccccaccggt nnccntgggg gggtgaanct cngnntcanc cngncgaggn ntcgnaagga | 720 |
| accggncctn ggncgaanng ancnntcnga agngccncnt cgtataaccc ccctcncca | 780 |
| nccnacngnt agntcccccc cngggtncgg aangg | 815 |

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

| | |
|---|---|
| ccgagatgtc tcgctccgtg gccttagctg tgctcgcgct actctctctt tctggcctgg | 60 |
| aggctatcca gcgtactcca aagattcagg tttactcacg tcatccagca gagaatggaa | 120 |
| agtcaaattt cctgaattgc tatgtgtctg ggtttcatcc atccgacatt gaanttgact | 180 |
| tactgaagaa tgganagaga attgaaaaag tggagcattc agacttgtct ttcagcaagg | 240 |
| actggtcttt ctatctcntg tactacactg aattcacccc cactgaaaaa gatgagtatg | 300 |
| cctgccgtgt gaaccatgtg actttgtcac agcccaagat agttaagtgg gatcgagaca | 360 |
| tgtaagcagn cnncatggaa gtttgaagat gccgcatttg gattggatga attccaaatt | 420 |
| ctgcttgctt gcnttttaat antgatatgc ntatacaccc tacccttat gnccccaaat | 480 |
| tgtagggtt acatnantgt tcncntngga catgatcttc ctttataant ccnccnttcg | 540 |
| aattgcccgt cnccngttn ngaatgtttc cnnaaccacg gttggctccc ccaggtcncc | 600 |
| tcttacggaa gggcctgggc cnctttcaa ggttgggga accnaaaatt tcncttntgc | 660 |
| ccncccncca cnntcttgng nncncanttt ggaacccttc cnattcccct tggcctcnna | 720 |
| nccttnncta anaaaacttn aaancgtngc naaanntttn acttcccccc ttacc | 775 |

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26

| | |
|---|---|
| anattantac agtgtaatct tttcccagag gtgtgtanag ggaacggggc ctagaggcat | 60 |
| cccanagata ncttatanca acagtgcttt gaccaagagc tgctgggcac atttcctgca | 120 |
| gaaaggtgg cggtccccat cactcctcct ctcccatagc catcccagag gggtgagtag | 180 |
| ccatcangcc ttcggtggga gggagtcang gaaacaacan accacagagc anacagacca | 240 |
| ntgatgacca tgggcgggag cgagcctctt ccctgnaccg gggtggcana ngangagccta | 300 |
| nctgaggggt cacactataa acgttaacga ccnagatnan cacctgcttc aagtgcaccc | 360 |
| ttcctacctg acnaccagng accnnnnaact gcngcctggg gacagnctg ggancagcta | 420 |
| acnnagcact cacctgcccc cccatggccg tncgcntccc tggtcctgnc aagggaagct | 480 |
| ccctgttgga attncgggga naccaaggga nccccctcct ccanctgtga aggaaaaann | 540 |

-continued

```
gatggaattt tnccttccg gccnntcccc tcttccttta cacgccccct nntactcntc   600
tccctctntt ntcctgncnc acttttnacc ccnnnatttc ccttnattga tcggannctn   660
ganattccac tnncgcctnc cntcnatcng naanacnaaa nactntctna cccngggat    720 gggnncctcg ntcatcctct cttttctnct accnccnntt ctttgcctct ccttngatca   780
tccaaccntc gntggccntn ccccccnnn tccttnccc                           820
```

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27

```
tctggtgat ggcctcttcc tcctcaggga cctctgactg ctctgggcca aagaatctct    60
tgtttcttct ccgagcccca ggcagcggtg attcagccct gcccaacctg attctgatga   120
ctgcggatgc tgtgacggac ccaaggggca aatagggtcc caggtccag ggagggggcgc   180 ctgctgagca cttccgcccc tcaccctgcc cagccctgc catgagctct gggctgggtc    240
tccgcctcca gggttctgct cttccangca ngccancaag tggcgctggg ccacactggc   300
ttcttcctgc cccntccctg gctctgantc tctgtcttcc tgtcctgtgc angcnccttg   360
gatctcagtt tccctcnctc anngaactct gtttctgann tcttcantta actntgantt   420
tatnaccnan tggnctgtnc tgtcnnactt taatgggccn gaccggctaa tccctccctc   480
nctcccttcc anttcnnnna accngcttnc cntcntctcc ccntacccg ccngggaanc    540 ctccttgcc ctnaccangg gccnnnaccg cccntnnctn gggggcnng gtnnctncnc     600 ctgntnnccc cnctcncnnt tnnctcgtcc cnncnncgcn nngcanttc ncgtcccnn     660 tnnctcttcn ngtntcgnaa ngtcncntn tnnnnngncn ngtnnntncn tccctctcnc    720
cnnntgnang tnnttnnnnc ncngnncccc nnnncnnnn nggnnntnnn tctncncngc    780
cccnnccccc ngnattaagg cctccnntct ccggccnc                           818
```

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28

```
aggaagggcg gagggatatt gtangggatt gagggatagg agnataanngg gggaggtgtg   60 tcccaacatg anggtgnngt tctcttttga angagggttg ngtttttann ccngttgggt   120
gattnaaccc cattgtatgg agnnaaaggn tttnagggat ttttcggctc ttatcagtat   180
ntanattcct gtnaatcgga aaatnatntt tcnncnggaa aatnttgctc ccatccgnaa   240
attnctcccg ggtagtgcat nttnggggn cngccangtt tcccaggctg ctanaatcgt    300
actaaagntt naagtgggan tncaaatgaa aacctnncac agagnatccn tacccgactg   360
tnnnttncct tcgccctntg actctgcnng agcccaatac ccnngngnat gtcncccgn    420 nnngcgncnc tgaaannnnc tcgnggctnn gancatcang gggtttcgca tcaaaagcnn   480
```

-continued

```
cgtttcncat naaggcactt tngcctcatc caaccnctng ccctcnncca tttngccgtc      540
nggttcncct acgctnnntng cncctnnntn ganattttnc ccgcctnggg naancctcct     600
gnaatgggta gggncttntc ttttnaccnn gnggtntact aatcnnctnc acgcntnctt     660
tctcnacccc ccccctttt caatcccanc ggcnaatggg gtctcccnn cgangggggg       720 nnncccannc c                                                          731
```

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

```
actagtccag tgtggtggaa ttccattgtg ttggggncnc ttctatgant antnttagat      60
cgctcanacc tcacanccte ccnacnangc ctataangaa nannaataga nctgtncnnt     120
atntntacnc tcatanncct cnnnacccac tccctcttaa ccentactgt gcctatngcn     180 tnnctantct ntgccgcctn cnanccaccn gtgggccnac cncnngnatt ctcnatctcc     240
tcnccatntn gcctananta ngtncatacc ctatacctac nccaatgcta nnnctaancn     300
tccatnantt annntaacta ccactgacnt ngactttcnc atnanctcct aatttgaatc     360
tactctgact cccacngcct annnattagc ancntccccc nacatntct caaccaaatc       420 ntcaacaacc tatctanctg ttcnccaacc nttncctccg atccccnnac aaccccccte     480 ccaaatacce nccacctgac ncctaacccn caccatcccg gcaagccnan ggncatttan     540
ccactggaat cacnatngga naaaaaaaac ccnaactctc tancncnnat ctccctaana     600
aatnctcctn naatttactn ncantnccat caanccacn tgaaacnnaa ccctgttttt      660
tanatccctt ctttcgaaaa ccnacccttt annnccccaac ctttngggcc ccccncctnc    720
ccnaatgaag gncncccaat cnangaaacg nccntgaaaa ancnaggcna anannntccg     780
canatcctat cccttanttn ggggncectt nccnnggcec cc                         822
```

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

```
cggccgcctg ctctggcaca tgcctcctga atggcatcaa aagtgatgga ctgcccattg      60
ctagagaaga ccttctctcc tactgtcatt atggagccct gcagactgag ggctcccctt     120
gtctgcagga tttgatgtct gaagtcgtgg agtgtggctt ggagctcctc atctacatna     180
gctggaagcc ctggagggcc tctctcgcca gcctcccccct tctctccacg ctctccangg    240
acaccagggg ctccaggcag cccattattc ccagnangac atggtgtttc tccacgcgga     300
cccatggggc ctgnaaggcc aggtctcct ttgacaccat ctctcccgtc ctgcctggca      360
ggccgtggga tccactantt ctanaacggn cgccaccncg gtgggagctc cagcttttgt    420
tcccnttaat gaaggttaat tgcncgcttg gcgtaatcat nggtcanaac tntttcctgt    480
gtgaaattgt ttntcccctc ncnattccnc ncnacatacn aacccggaan cataaagtgt    540
```

-continued

```
taaagcctgg gggtngcctn nngaatnaac tnaactcaat taattgcgtt ggctcatggc      600
ccgctttccn ttcnggaaaa ctgtcntccc ctgcnttnnt gaatcggcca ccccccnggg      660
aaaagcggtt tgcnttttng ggggntcctt ccncttcccc cctcnctaan ccctncgcct      720
cggtcgttnc nggtngcggg gaangggnat nnnctcccnc naaggggng agnnngntat       780 ccccaaa                                                                787
```

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31

```
ttttttttttt ttttttttggc gatgctactg tttaattgca ggaggtgggg gtgtgtgtac    60
catgtaccag ggctattaga agcaagaagg aaggagggag ggcagagcgc cctgctgagc     120
aacaaaggac tcctgcagcc ttctctgtct gtctcttggc gcaggcacat ggggaggcct     180
cccgcagggt gggggccacc agtccagggg tgggagcact acangggtg ggagtgggtg      240 gtggctggtn cnaatggcct gncacanatc cctacgattc ttgacacctg gatttcacca     300
ggggaccttc tgttctccca nggnaacttc ntnnatctcn aaagaacaca actgtttctt     360
cngcanttct ggctgttcat ggaaagcaca ggtgtccnat ttnggctggg acttggtaca     420
tatggttccg gcccacctct cccntcnaan aagtaattca ccccccccn cntctnttg      480 cctgggccct taantaccca caccggaact canttantta ttcatcttng gntgggcttg     540
ntnatcnccn cctgaagcg ccaagttgaa aggccacgcc gtnccnctc cccatagnan       600 nttttnncnt canctaatgc ccccccnggc aacnatccaa tccccccccn tggggccc       660 agcccanggc ccccgnctcg ggnnccngn cncgnantcc ccaggntctc ccantcngnc      720
ccnnngcncc cccgcacgca gaacanaagg ntngagccnc cgcannnnnn nggtnncnac     780 ctcgccccc ccnncgnng                                                   799
```

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32

```
tttttttttt tttttttttt tttttttttt tttttttttt tttttttttt tttttttttt      60
ttttnccnag ggcaggttta ttgacaacct cncgggacac aancaggctg gggacaggac     120
ggcaacaggc tccggcggcg gcggcggcgg ccctacctgc ggtaccaaat ntgcagcctc     180
cgctcccgct tgatnttcct ctgcagctgc aggatgcnt aaaacagggc ctcggccntn      240
ggtgggcacc ctgggattn aatttccacg ggcacaatgc ggtcgcancc cctcaccacc     300
nattaggaat agtggtntta cccnccnccg ttggcncact cccntggaa accacttntc     360 gcggctccgg catctggtct taaaccttgc aaacnctggg gccctcttt tggttantnt      420 nccngccaca atcatnactc agactggcnc gggctggccc caaaaaancn ccccaaaacc    480
```

-continued

| | |
|---|---:|
| ggnccatgtc ttnncggggt tgctgcnatn tncatcacct cccgggcnca ncaggncaac | 540 |
| ccaaaagttc ttgnggcccn caaaaaanct ccggggggnc ccagtttcaa caaagtcatc | 600 |
| cccctggcc cccaaatcct cccccgntt nctgggttg ggaacccacg cctctnnctt | 660 |
| tggnnggcaa gntggntccc ccttcgggcc cccggtgggc ccnnctctaa ngaaaacncc | 720 |
| ntcctnnnca ccatcccccc nngnnacgnc tancaangna tccctttttt tanaaacggg | 780 |
| ccccccncg | 789 |

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33

| | |
|---|---:|
| gacagaacat gttggatggt ggagcacctt tctatacgac ttacaggaca gcagatgggg | 60 |
| aattcatggc tgttggagca atanaacccc agttctacga gctgctgatc aaaggacttg | 120 |
| gactaaagtc tgatgaactt cccaatcaga tgagcatgga tgattggcca gaaatgaana | 180 |
| agaagtttgc agatgtattt gcaaagaaga cgaaggcaga gtggtgtcaa atctttgacg | 240 |
| gcacagatgc ctgtgtgact ccggttctga cttttgagga ggttgttcat catgatcaca | 300 |
| acaangaacg gggctcgttt atcaccantg aggagcagga cgtgagcccc cgccctgcac | 360 |
| ctctgctgtt aaacacccca gccatcccct cttcaaaag ggatccacta cttctagagc | 420 |
| ggncgccacc gcggtggagc tccagctttt gttcccttta gtgagggtta attgcgcgct | 480 |
| tggcgtaatc atggtcatan ctgtttcctg tgtgaaattg ttatccgctc acaattccac | 540 |
| acaacatacg anccggaagc atnaaatttt aaagcctggn ggtngcctaa tgantgaact | 600 |
| nactcacatt aattggcttt gcgctcactg cccgctttcc agtccggaaa acctgtcctt | 660 |
| gccagctgcc nttaatgaat cnggccaccc ccgggggaaa aggcngtttg cttnttgggg | 720 |
| cgcncttccc gctttctcgc ttcctgaant ccttccccc ggtctttcgg cttgcggcna | 780 |
| acggtatcna cct | 793 |

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34

| | |
|---|---:|
| gccgcgaccg gcatgtacga gcaactcaag ggcgagtgga accgtaaaag ccccaatctt | 60 |
| ancaagtgcg gggaanagct gggtcgactc aagctagttc ttctggagct caacttcttg | 120 |
| ccaaccacag ggaccaagct gaccaaacag cagctaattc tggcccgtga catactggag | 180 |
| atcggggccc aatggagcat cctacgcaan gacatcccct ccttcgagcg ctacatggcc | 240 |
| cagctcaaat gctactactt tgattacaan gagcagctcc ccgagtcagc ctatatgcac | 300 |
| cagctcttgg gcctcaacct cctcttcctg ctgtcccaga accgggtggc tgantnccac | 360 |
| acgganttgg ancggctgcc tgcccaanga catacanacc aatgtctaca tcnaccacca | 420 |
| gtgtcctgga gcaatactga tgganggcag ctaccncaaa gtnttcctgg ccnagggtaa | 480 |

| | | |
|---|---|---|
| catcccccgc cgagagctac accttcttca ttgacatcct gctcgacact atcagggatg | 540 | |
| aaaatcgcng ggttgctcca gaaaggctnc aanaanatcc ttttcnctga aggcccccgg | 600 | |
| atncnctagt nctagaatcg gcccgccatc gcggtggganc ctccaacctt tcgttnccct | 660 | |
| ttactgaggg ttnattgccg cccttggcgt tatcatggtc acnccngttn cctgtgttga | 720 | |
| aattnttaac cccccacaat tccacgccna cattng | 756 | |

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

| | | |
|---|---|---|
| ggggatctct anatcnacct gnatgcatgg ttgtcggtgt ggtcgctgtc gatgaaatg | 60 | |
| aacaggatct tgcccttgaa gctctcggct gctgtnttta agttgctcag tctgccgtca | 120 | |
| tagtcagaca cnctcttggg caaaaaacan caggatntga gtcttgattt cacctccaat | 180 | |
| aatcttcngg gctgtctgct cggtgaactc gatgacnang ggcagctggt tgtgtntgat | 240 | |
| aaantccanc angttctcct tggtgacctc cccttcaaag ttgttccggc cttcatcaaa | 300 | |
| cttctnnaan angannancc canctttgtc gagctggnat ttgganaaca cgtcactgtt | 360 | |
| ggaaactgat cccaaatggt atgtcatcca tcgcctctgc tgcctgcaaa aaacttgctt | 420 | |
| ggcncaaatc cgactcccn tccttgaaag aagcccatca cacccccctc cctggactcc | 480 | |
| nncaangact ctnccgctnc cccntccnng cagggttggt ggcanncegg gcccntgcgc | 540 | |
| ttcttcagcc agttcacnat nttcatcagc ccctctgcca gctgttntat tccttggggg | 600 | |
| ggaanccgtc tctcccttcc tgaannaact ttgaccgtng gaatagccgc gntcnccnt | 660 | |
| acntnctggg ccggggttcaa antccctccn ttgncnntcn cctcgggcca ttctggattt | 720 | |
| nccnaacttt ttccttcccc cnccccncgg ngtttggntt tttcatnggg ccccaactct | 780 | |
| gctnttggcc antccctgg gggcntntan cnccccctnt ggtcccntng ggcc | 834 | |

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

| | | |
|---|---|---|
| cggncgcttt ccngccgcgc cccgtttcca tgacnaaggc tcccttcang ttaaatacnn | 60 | |
| cctagnaaac attaatgggt tgctctacta atacatcata cnaaccagta agcctgccca | 120 | |
| naacgccaac tcaggccatt cctaccaaag gaagaaaggc tggtctctcc accccctgta | 180 | |
| ggaaaggcct gccttgtaag acaccacaat ncggctgaat ctnaagtctt gtgttttact | 240 | |
| aatggaaaaa aaaataaac aanaggtttt gttctcatgg ctgcccaccg cagcctggca | 300 | |
| ctaaaacanc ccagcgctca cttctgcttg ganaaatatt cttttgctctt ttggacatca | 360 | |
| ggcttgatgg tatcactgcc acntttccac ccagctgggc nccttcccc catntttgtc | 420 | |
| antganctgg aaggcctgaa ncttagtctc caaaagtctc ngcccacaag accggccacc | 480 | |

```
aggggangtc ntttncagtg gatctgccaa anantacccn tatcatcnnt gaataaaaag      540 gccccctgaac ganatgcttc cancanccctt taagacccat aatcctngaa ccatggtgcc    600
cttccggtct gatccnaaag gaatgttcct gggtcccant ccctcctttg ttncttacgt     660
tgtnttggac ccntgctngn atnacccaan tganatcccc ngaagcaccc tnccctggc      720 atttganttt cntaaattct ctgccctacn nctgaaagca cnattccctn ggcnccnaan     780
ggngaactca agaaggtctn ngaaaaacca cncn                                 814
```

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

```
gcatgctgct cttcctcaaa gttgttcttg ttgccataac aaccaccata ggtaaagcgg      60
gcgcagtgtt cgctgaaggg gttgtagtac cagcgcggga tgctctcctt gcagagtcct     120
gtgtctggca ggtccacgca atgccctttg tcactgggga aatggatgcg ctggagctcg     180
tcnaanccac tcgtgtattt ttcacangca gcctcctccg aagcntccgg gcagttgggg     240
gtgtcgtcac actccactaa actgtcgatn cancagccca ttgctgcagc ggaactgggt    300
gggctgacag gtgccagaac acactggatn ggcctttcca tggaagggcc tggggggaaat   360 cncctnancc caaactgcct ctcaaaggcc accttgcaca ccccgacagg ctagaaatgc    420
actcttcttc ccaaaggtag ttgttcttgt tgcccaagca ncctccanca aaccaaaaanc   480 ttgcaaaatc tgctccgtgg gggtcatnnn taccanggtt ggggaaanaa acccggcngn    540
ganccncctt gtttgaatgc naaggnaata atcctcctgt cttgcttggg tggaanagca    600
caattgaact gttaacnttg ggccngttc cnctngggtg gtctgaaact aatcaccgtc     660
actggaaaaa ggtangtgcc ttccttgaat tcccaaantt ccctngntt tgggtnnttt     720 ctcctctncc ctaaaaatcg tnttccccccc ccntanggcg                         760
```

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

```
tttttttttt tttttttttt tttttttttt tttttaaaaa cccctccat tgaatgaaaa       60 cttccnaaat tgtccaaccc cctcnnccaa atnnccattt ccgggggggg gttccaaacc     120
caaattaatt ttgganttta aattaaatnt tnattnggg aanaanccaa atgtnaagaa     180
aatttaaccc attatnaact taaatnccctn gaaacccntg gnttccaaaa atttttaacc    240
cttaaatccc tccgaaattg ntaanggaaa accaaattcn cctaaggctn tttgaaggtt    300
ngatttaaac ccccttnant tnttttnacc cnngnctnaa ntatttngnt tccggtgttt    360
tcctnttaan cntnggtaac tcccgntaat gaannncccct aanccaatta aaccgaattt  420 ttttttgaatt ggaaattccn ngggaattna ccggggtttt tccntttggg ggccatncc    480 cccnctttcg ggtttgggn ntaggttgaa tttttnnang nccaaaaaaa nccccccaana   540
```

| | |
|---|---|
| aaaaaactcc caagnnttaa ttngaatntc ccccttccca ggccttttgg gaaaggnggg | 600 |
| tttntggggg ccngggantt cnttccccn ttnccncccc cccccngggt aaanggttat | 660 |
| ngnntttggt ttttgggccc cttnanggac cttccggatn gaaattaaat ccccgggncg | 720 |
| gccg | 724 |

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

| | |
|---|---|
| ttttttttt ttttctttg ctcacattta atttttattt tgattttttt taatgctgca | 60 |
| caacacaata tttatttcat ttgtttcttt tatttcattt tatttgtttg ctgctgctgt | 120 |
| tttatttatt tttactgaaa gtgagaggga acttttgtgg cctttttttcc ttttctgta | 180 |
| ggccgcctta agctttctaa atttggaaca tctaagcaag ctgaangaa aaggggttt | 240 |
| cgcaaaatca ctcggggaa nggaaaggtt gctttgttaa tcatgcccta tggtgggtga | 300 |
| ttaactgctt gtacaattac ntttcacttt taattaattg tgctnaangc tttaattana | 360 |
| cttgggggtt ccctccccan accaaccccc ctgacaaaaa gtgccngccc tcaaatnatg | 420 |
| tcccggcnnt cnttgaaaca cacngcngaa ngttctcatt ntcccncnc caggtnaaaa | 480 |
| tgaagggtta ccatntttaa cnccacctcc acntggcnnn gcctgaatcc tcnaaaancn | 540 |
| ccctcaancn aattnctnng ccccggtcnc gcntnngtcc cnccccgggct ccgggaantn | 600 |
| caccccccnga anncnntnnc naacnaaatt ccgaaaatat tcccnntcnc tcaattcccc | 660 |
| cnnagactnt cctcnncnan cncaattttc ttttnntcac gaacncgnnc cnnaaaatgn | 720 |
| nnnncnccctc cnctngtccn naatcnccan c | 751 |

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | |
|---|---|
| gtggtatttt ctgtaagatc aggtgttcct ccctcgtagg tttagaggaa acaccctcat | 60 |
| agatgaaaac ccccccgaga cagcagcact gcaactgcca agcagccggg gtaggagggg | 120 |
| cgccctatgc acagctgggc ccttgagaca gcagggcttc gatgtcaggc tcgatgtcaa | 180 |
| tggtctggaa gcggcggctg tacctgcgta ggggcacacc gtcagggccc accaggaact | 240 |
| tctcaaagtt ccaggcaacn tcgttgcgac acaccggaga ccaggtgatn agcttggggt | 300 |
| cggtcataan cgcggtggcg tcgtcgctgg gagctggcag ggcctcccgc aggaaggcna | 360 |
| ataaaaggtg cgcccccgca ccgttcanct cgcacttctc naanaccatg angttgggct | 420 |
| cnaacccacc accanncgg acttccttga nggaattccc aaatctcttc gntcttgggc | 480 |
| ttctnctgat gccctanctg gttgcccngn atgccaanca ncccaancc ccggggtcct | 540 |
| aaancaccn cctcctcntt tcatctgggt tnttntcccc ggaccntggt tcctctcaag | 600 |
| ggancccata tctcnaccan tactcaccnt ncccccccnt gnnaccanc cttctanngn | 660 |

| | |
|---|---|
| ttcccncccg ncctctggcc cntcaaanan gcttncacna cctgggtctg ccttcccccc | 720 |
| tnccctatct gnacccncn tttgtctcan tnt | 753 |

<210> SEQ ID NO 41
<211> LENGTH: 341
<212> TYPE: DNA
<213> ORGANISM: Homo sapien

<400> SEQUENCE: 41

| | |
|---|---|
| actatatcca tcacaacaga catgcttcat cccatagact tcttgacata gcttcaaatg | 60 |
| agtgaaccca tccttgattt atatacatat atgttctcag tattttggga gcctttccac | 120 |
| ttctttaaac cttgttcatt atgaacactg aaaataggaa tttgtgaaga gttaaaaagt | 180 |
| tatagcttgt ttacgtagta agttttgaa gtctacattc aatccagaca cttagttgag | 240 |
| tgttaaactg tgattttaa aaaatatcat ttgagaatat tctttcagag gtattttcat | 300 |
| ttttactttt tgattaattg tgttttatat attagggtag t | 341 |

210> SEQ ID NO 42
<211> LENGTH: 01
<212> TYPE: DA
<213> ORGANISM: Homo sapien

<400> SEQUENCE: 42

| | |
|---|---|
| acttactgaa tttagttctg tgctcttcct tatttagtgt tgtatcataa atactttgat | 60 |
| gtttcaaaca ttctaaataa ataattttca gtggcttcat a | 101 |

<210> SEQ ID NO 43
<211> LENGTH: 305
<212> TYPE: DNA
<213> ORGANISM: Homo sapien

<400> SEQUENCE: 43

| | |
|---|---|
| acatctttgt tacagtctaa gatgtgttct taaatcacca ttccttcctg gtcctcaccc | 60 |
| tccagggtgg tctcacactg taattagagc tattgaggag tctttacagc aaattaagat | 120 |
| tcagatgcct tgctaagtct agagttctag agttatgttt cagaaagtct aagaaaccca | 180 |
| cctcttgaga ggtcagtaaa gaggacttaa tatttcatat ctacaaaatg accacaggat | 240 |
| tggatacaga acgagagtta tcctggataa ctcagagctg agtacctgcc cgggggccgc | 300 |
| tcgaa | 305 |

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

| | |
|---|---|
| acataaatat cagagaaaag tagtctttga aatatttacg tccaggagtt ctttgtttct | 60 |
| gattatttgg tgtgtgtttt ggtttgtgtc caaagtattg gcagcttcag ttttcatttt | 120 |
| ctctccatcc tcgggcattc ttcccaaatt tatataccag tcttcgtcca tccacacgct | 180 |
| ccagaatttc tcttttgtag taatatctca tagctcggct gagcttttca taggtcatgc | 240 |
| tgctgttgtt cttcttttta ccccatagct gagccactgc ctctgatttc aagaacctga | 300 |

```
agacgccctc agatcggtct tcccatttta ttaatcctgg gttcttgtct gggttcaaga      360
ggatgtcgcg gatgaattcc cataagtgag tccctctcgg gttgtgcttt ttggtgtggc      420
acttggcagg ggggtcttgc tccttttttca tatcaggtga ctctgcaaca ggaaggtgac     480
tggtggttgt catggagatc tgagcccggc agaaagtttt gctgtccaac aaatctactg      540
tgctaccata gttggtgtca tataaatagt tctngtcttt ccaggtgttc atgatggaag      600
gctcagtttg ttcagtcttg acaatgacat tgtgtgtgga ctggaacagg tcactactgc      660
actggccgtt ccacttcaga tgctgcaagt tgctgtagag gagntgcccc gccgtccctg      720
ccgcccgggt gaactcctgc aaactcatgc tgcaaaggtg ctcgccgttg atgtcgaact      780
cntggaaagg gatacaattg gcatccagct ggttggtgtc caggaggtga tggagccact      840
cccacacctg gt                                                         852

<210> SEQ ID NO 45
<211> LENGTH: 234
<212> TYPE: DNA
<213> ORGANISM: Homo sapien

<400> SEQUENCE: 45
acaacagacc cttgctcgct aacgacctca tgctcatcaa gttggacgaa tccgtgtccg       60
agtctgacac catccggagc atcagcattg cttcgcagtg ccctaccgcg gggaactctt     120
gcctcgtttc tggctggggt ctgctggcga acggcagaat gcctaccgtg ctgcagtgcg     180
tgaacgtgtc ggtggtgtct gaggaggtct gcagtaagct ctatgacccg ctgt           234

210> SEQ ID NO 46
<211> LENGTH: 90
<212> TYPE: DA
<213> ORGANSM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46
actttttatt taaatgttta taaggcagat ctatgagaat gatagaaaac atggtgtgta       60
atttgatagc aatattttgg agattacaga gttttagtaa ttaccaatta cacagttaaa     120
aagaagataa tatattccaa gcanatacaa aatatctaat gaaagatcaa ggcaggaaaa     180
tgantataac taattgacaa tggaaaatca attttaatgt gaattgcaca ttatcctta      240 aaagctttca aaanaaanaa ttattgcagt ctanttaatt caaacagtgt taaatggtat     300
caggataaaa aactgaaggg canaaagaat taattttcac ttcatgtaac ncacccanat     360
ttacaatggc ttaaatgcan ggaaaaagca gtggaagtag ggaagtantc aaggtctttc     420
tggtctctaa tctgccttac tctttgggtg tggctttgat cctctggaga cagctgccag     480
ggctcctgtt atatccacaa tcccagcagc aagatgaagg gatgaaaaag gacacatgct     540
gccttccttt gaggagactt catctcactg gccaacactc agtcacatgt                 590

<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47
```

```
acaaggggc ataatgaagg agtggggana gattttaaag aaggaaaaaa aacgaggccc    60
tgaacagaat tttcctgnac aacgggctt caaaataatt ttcttgggga ggttcaagac   120
gcttcactgc ttgaaactta aatggatgtg ggacanaatt ttctgtaatg accctgaggg   180
cattacagac gggactctgg gaggaaggat aaacagaaag gggacaaagg ctaatcccaa   240
aacatcaaag aaaggaaggt ggcgtcatac ctcccagcct acacagttct ccagggctct   300
cctcatccct ggaggacgac agtggaggaa caactgacca tgtccccagg ctcctgtgtg   360
ctggctcctg gtcttcagcc cccagctctg gaagcccacc ctctgctgat cctgcgtggc   420
ccacactcct tgaacacaca tccccaggtt atattcctgg acatggctga acctcctatt   480
cctacttccg agatgccttg ctccctgcag cctgtcaaaa tcccactcac cctccaaacc   540
acggcatggg aagcctttct gacttgcctg attactccag catcttggaa caatccctga   600
ttccccactc cttagaggca agatagggtg gttaagagta gggctggacc acttggagcc   660
aggctgctgg cttcaaattn tggctcattt acgagctatg ggaccttggg caagtnatct   720
tcacttctat gggcntcatt ttgttctacc tgcaaaatgg gggataataa tagt          774

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48
canaaattga aattttataa aaaggcattt ttctcttata tccataaaat gatataattt    60
ttgcaantat anaaatgtgt cataaattat aatgttcctt aattacagct caacgcaact   120
tggt                                                                124

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt    60
tgtggctaca ggtggtgtct gactgcatna aaaantttt tacgggtgat tgcaaaaatt   120
ttagggcacc catatcccaa gcantgt                                       147

<210> SEQ ID NO 50
<211> LENGTH: 107
<212> TYPE: DNA
<213> ORGANISM: Homo sapien

<400> SEQUENCE: 50
acattaaatt aataaaagga ctgttggggt tctgctaaaa cacatggctt gatatattgc    60
atggtttgag gttaggagga gttaggcata tgttttggga gagggt                  107

<210> SEQ ID NO 51
<211> LENGTH: 204
<212> TYPE: DNA
```

<213> ORGANISM: Homo sapien

<400> SEQUENCE: 51

| gtcctaggaa gtctagggga cacacgactc tggggtcacg gggccgacac acttgcacgg | 60 |
| cgggaaggaa aggcagagaa gtgacaccgt caggggaaaa tgacagaaag gaaaatcaag | 120 |
| gccttgcaag gtcagaaagg ggactcaggg cttccaccac agccctgccc cacttggcca | 180 |
| cctcccttt gggaccagca atgt | 204 |

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52

| acaaagataa catttatctt ataacaaaaa tttgatagtt ttaaaggtta gtattgtgta | 60 |
| gggtattttc caaagacta aagagataac tcaggtaaaa agttagaaat gtataaaaca | 120 |
| ccatcagaca ggttttaaa aaacaacata ttacaaaatt agacaatcat ccttaaaaaa | 180 |
| aaaacttctt gtatcaattt cttttgttca aaatgactga cttaantatt tttaaatatt | 240 |
| tcanaaacac ttcctcaaaa attttcaana tggtagcttt canatgtncc ctcagtccca | 300 |
| atgttgctca gataaataaa tctcgtgaga acttaccacc caccacaagc tttctggggc | 360 |
| atgcaacagt gtcttttctt tncttttct tttttttt ttacaggcac agaaactcat | 420 |
| caattttatt tggataacaa agggtctcca aattatattg aaaaataaat ccaagttaat | 480 |
| atcactcttg t | 491 |

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53

| acataattta gcagggctaa ttaccataag atgctattta ttaanaggtn tatgatctga | 60 |
| gtattaacag ttgctgaagt ttggtatttt tatgcagcat tttcttttg ctttgataac | 120 |
| actacagaac ccttaaggac actgaaaatt agtaagtaaa gttcagaaac attagctgct | 180 |
| caatcaaatc tctacataac actatagtaa ttaaaacgtt aaaaaaagt gttgaaatct | 240 |
| gcactagtat anaccgctcc tgtcaggata anactgcttt ggaacagaaa gggaaaaanc | 300 |
| agctttgant ttctttgtgc tgatangagg aaaggctgaa ttaccttgtt gcctctccct | 360 |
| aatgattggc aggtcnggta aatnccaaaa catattccaa ctcaacactt cttttccncg | 420 |
| tancttgant ctgtgtattc caggancagg cggatggaat gggccagccc ncggatgttc | 480 |
| cant | 484 |

<210> SEQ ID NO 54
<211> LENGTH: 151
<212> TYPE: DNA
<213> ORGANISM: Homo sapien

<400> SEQUENCE: 54

-continued

| | |
|---|---|
| actaaacctc gtgcttgtga actccataca gaaaacggtg ccatccctga acacggctgg | 60 |
| ccactgggta tactgctgac aaccgcaaca acaaaaacac aaatccttgg cactggctag | 120 |
| tctatgtcct ctcaagtgcc tttttgtttg t | 151 |

<210> SEQ ID NO 55
<211> LENGTH: 91
<212> TYPE: DNA
<213> ORGANISM: Homo sapien

<400> SEQUENCE: 55

| | |
|---|---|
| acctggcttg tctccgggtg gttcccggcg ccccccacgg tccccagaac ggacactttc | 60 |
| gccctccagt ggatactcga gccaaagtgg t | 91 |

<210> SEQ ID NO 56
<211> LENGTH: 133
<212> TYPE: DNA
<213> ORGANISM: Homo sapien

<400> SEQUENCE: 56

| | |
|---|---|
| ggcggatgtg cgttggttat atacaaatat gtcattttat gtaagggact tgagtatact | 60 |
| tggatttttg gtatctgtgg gttgggggga cggtccagga accaataccc catggatacc | 120 |
| aagggacaac tgt | 133 |

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57

| | |
|---|---|
| actctggaga acctgagccg ctgctccgcc tctgggatga ggtgatgcan gcngtggcgc | 60 |
| gactgggagc tgagcccttc cctttgcgcc tgcctcagag gattgttgcc gacntgcana | 120 |
| tctcantggg ctggatncat gcagggt | 147 |

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58

| | |
|---|---|
| acagggatat aggtttnaag ttattgtnat tgtaaaatac attgaattt ctgtatactc | 60 |
| tgattacata catttatcct ttaaaaaaga tgtaaatctt aattttatg ccatctatta | 120 |
| atttaccaat gagttacctt gtaaatgaga agtcatgata gcactgaatt ttaactagtt | 180 |
| ttgacttcta agtttggt | 198 |

<210> SEQ ID NO 59
<211> LENGTH: 330
<212> TYPE: DNA
<213> ORGANISM: Homo sapien

<400> SEQUENCE: 59

| | |
|---|---|
| acaacaaatg ggttgtgagg aagtcttatc agcaaaactg gtgatggcta ctgaaaagat | 60 |

-continued ccattgaaaa ttatcattaa tgattttaaa tgacaagtta tcaaaaactc actcaatttt        120
cacctgtgct agcttgctaa atgggagtt aactctagag caaatatagt atcttctgaa         180
tacagtcaat aaatgacaaa gccagggcct acaggtggtt tccagacttt ccagacccag        240
cagaaggaat ctattttatc acatggatct ccgtctgtgc tcaaaatacc taatgatatt        300
tttcgtcttt attggacttc tttgaagagt                                         330

<210> SEQ ID NO 60
<211> LENGTH: 175
<212> TYPE: DNA
<213> ORGANISM: Homo sapien

<400> SEQUENCE: 60
accgtgggtg ccttctacat tcctgacggc tccttcacca acatctggtt ctacttcggc         60
gtcgtgggct cctcctctt catcctcatc cagctggtgc tgctcatcga ctttgcgcac        120
tcctggaacc agcggtggct gggcaaggcc gaggagtgcg attcccgtgc ctggt            175

<210> SEQ ID NO 61
<211> LENGTH: 154
<212> TYPE: DNA
<213> ORGANISM: Homo sapien

<400> SEQUENCE: 61
accccacttt tcctcctgtg agcagtctgg acttctcact gctacatgat gagggtgagt         60
ggttgttgct cttcaacagt atcctcccct ttccggatct gctgagccgg acagcagtgc        120
tggactgcac agccccgggg ctccacattg ctgt                                    154

<210> SEQ ID NO 62
<211> LENGTH: 30
<212> TYPE: DNA
<213> ORGANISM: Homo sapien

<400> SEQUENCE: 62
cgctcgagcc ctatagtgag tcgtattaga                                          30

<210> SEQ ID NO 63
<211> LENGTH: 89
<212> TYPE: DNA
<213> ORGANISM: Homo sapien

<400> SEQUENCE: 63
acaagtcatt tcagcaccct ttgctcttca aaactgacca tcttttatat ttaatgcttc         60
ctgtatgaat aaaaatggtt atgtcaagt                                           89

<210> SEQ ID NO 64
<211> LENGTH: 97
<212> TYPE: DNA
<213> ORGANISM: Homo sapien

<400> SEQUENCE: 64
accggagtaa ctgagtcggg acgctgaatc tgaatccacc aataaataaa ggttctgcag         60
aatcagtgca tccaggattg gtccttggat ctggggt                                  97

<210> SEQ ID NO 65
<211> LENGTH: 377
<212> TYPE: DNA
<213> ORGANISM: Homo sapien
<220> FEATURE:

<221> NAME/KEY: misc_feature
<222> LOCATION: (1)...(377)
<223> OTHER INFORMATION: n = A,T,C or G

<400> SEQUENCE: 65

| | | | | | |
|---|---|---|---|---|---|
| acaacaanaa | ntcccttctt | taggccactg | atggaaacct | ggaacccct | tttgatggca | 60 |
| gcatggcgtc | ctaggccttg | acacagcggc | tggggtttgg | gctntcccaa | accgcacacc | 120 |
| ccaaccctgg | tctacccaca | nttctggcta | tgggctgtct | ctgccactga | acatcagggt | 180 |
| tcggtcataa | natgaaatcc | caangggac | agaggtcagt | agaggaagct | caatgagaaa | 240 |
| ggtgctgttt | gctcagccag | aaaacagctg | cctggcattc | gccgctgaac | tatgaacccg | 300 |
| tggggtgaa | ctaccccan | gaggaatcat | gcctgggcga | tgcaaggtg | ccaacaggag | 360 |
| gggcgggagg | agcatgt | | | | 377 |

<210> SEQ ID NO 66
<211> LENGTH: 305
<212> TYPE: DNA
<213> ORGANISM: Homo sapien

<400> SEQUENCE: 66

| | | | | | |
|---|---|---|---|---|---|
| acgcctttcc | ctcagaattc | agggaagaga | ctgtcgcctg | ccttcctccg | ttgttgcgtg | 60 |
| agaacccgtg | tgccccttcc | caccatatcc | accctcgctc | catctttgaa | ctcaaacacg | 120 |
| aggaactaac | tgcaccctgg | tcctctcccc | agtccccagt | tcaccctcca | tccctcacct | 180 |
| tcctccactc | taagggatat | caacactgcc | cagcacaggg | gccctgaatt | tatgtggttt | 240 |
| ttatatattt | tttaataaga | tgcactttat | gtcatttttt | aataaagtct | gaagaattac | 300 |
| tgttt | | | | | 305 |

<210> SEQ ID NO 67
<211> LENGTH: 385
<212> TYPE: DNA
<213> ORGANISM: Homo sapien

<400> SEQUENCE: 67

| | | | | | |
|---|---|---|---|---|---|
| actacacaca | ctccacttgc | ccttgtgaga | cactttgtcc | cagcacttta | ggaatgctga | 60 |
| ggtcggacca | gccacatctc | atgtgcaaga | ttgcccagca | gacatcaggt | ctgagagttc | 120 |
| cccttttaaa | aaggggact | tgcttaaaaa | agaagtctag | ccacgattgt | gtagagcagc | 180 |
| tgtgctgtgc | tggagattca | cttttgagag | agttctcctc | tgagacctga | tctttagagg | 240 |
| ctgggcagtc | ttgcacatga | gatggggctg | gtctgatctc | agcactcctt | agtctgcttg | 300 |
| cctctcccag | ggccccagcc | tggccacacc | tgcttacagg | gcactctcag | atgcccatac | 360 |
| catagtttct | gtgctagtgg | accgt | | | 385 |

<210> SEQ ID NO 68
<211> LENGTH: 73
<212> TYPE: DNA
<213> ORGANISM: Homo sapien

<400> SEQUENCE: 68

| | | | | | |
|---|---|---|---|---|---|
| acttaaccag | atatattttt | accccagatg | gggatattct | ttgtaaaaaa | tgaaaataaa | 60 |
| gttttttaa | tgg | | | | 73 |

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69

| actagtccag tgtggtggaa ttccattgtg ttgggggctc tcaccctcct ctcctgcagc | 60 |
| tccagctttg tgctctgcct ctgaggagac catggcccag catctgagta ccctgctgct | 120 |
| cctgctggcc accctagctg tggccctggc ctggagcccc aaggaggagg ataggataat | 180 |
| cccgggtggc atctataacg cagacctcaa tgatgagtgg gtacagcgtg cccttcactt | 240 |
| cgccatcagc gagtataaca aggccaccaa agatgactac tacagacgtc cgctgcgggt | 300 |
| actaagagcc aggcaacaga ccgttggggg ggtgaattac ttcttcgacg tagaggtggg | 360 |
| ccgaaccata tgtaccaagt cccagcccaa cttggacacc tgtgccttcc atgaacagcc | 420 |
| agaactgcag aagaaacagt tgtgctcttt cgagatctac gaagttccct ggggagaaca | 480 |
| gaangtccct gggtgaaatc caggtgtcaa gaaatcctan ggatctgttg ccaggc | 536 |

<210> SEQ ID NO 70
<211> LENGTH: 477
<212> TYPE: DNA
<213> ORGANISM: Homo sapien

<400> SEQUENCE: 70

| atgacccta acaggggccc tctcagccct cctaatgacc tccggcctag ccatgtgatt | 60 |
| tcacttccac tccataacgc tcctcatact aggcctacta accaacacac taaccatata | 120 |
| ccaatgatgg cgcgatgtaa cacgagaaag cataccaa ggccaccaca caccacctgt | 180 |
| ccaaaaggc cttcgatacg ggataatcct atttattacc tcagaagttt ttttcttcgc | 240 |
| agggattttt ctgagccttt taccactcca gcctagcccc taccccccaa ctaggagggc | 300 |
| actggccccc aacaggcatc accccgctaa atccctaga agtcccactc ctaaacacat | 360 |
| ccgtattact cgcatcagga gtatcaatca cctgagctca ccatagtcta atagaaaaca | 420 |
| accgaaacca aattattcaa agcactgctt attacaattt tactgggtct ctatttt | 477 |

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

| agagctatag gtacagtgtg atctcagctt tgcaaacaca ttttctacat agatagtact | 60 |
| aggtattaat agatatgtaa agaaagaaat cacaccatta ataatggtaa gattggttta | 120 |
| tgtgatttta gtggtatttt tggcaccctt atatatgttt ccaaactttt cagcagtgat | 180 |
| attatttcca taacttaaaa agtgagtttg aaaagaaaa tctccagcaa gcatctcatt | 240 |
| taaataaagg tttgtcatct ttaaaaatac agcaatatgt gactttttaa aaaagctgtc | 300 |
| aaataggtgt gaccctacta ataattatta gaaatacatt taaaaacatc gagtacctca | 360 |
| agtcagtttg ccttgaaaaa tatcaaatat aactcttaga gaaatgtaca taaagaatg | 420 |
| cttcgtaatt ttggagtang aggttccctc tcaattttg tattttttaaa aagtacatgg | 480 |
| taaaaaaaaa aattcacaac agtatataag gctgtaaaat gaagaattct gcc | 533 |

<210> SEQ ID NO 72
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 72

| | | | | | |
|---|---|---|---|---|---|
| tattacggaa | aaacacacca | cataattcaa | ctancaaaga | anactgcttc | agggcgtgta | 60 |
| aaatgaaagg | cttccaggca | gttatctgat | taaagaacac | taaagagggg | acaaggctaa | 120 |
| aagccgcagg | atgtctacac | tatancaggc | gctatttggg | ttggctggag | gagctgtgga | 180 |
| aaacatggan | agattggtgc | tgganatcgc | cgtggctatt | cctcattgtt | attacanagt | 240 |
| gaggttctct | gtgtgcccac | tggtttgaaa | accgttctnc | aataatgata | gaatagtaca | 300 |
| cacatgagaa | ctgaaatggc | ccaaacccag | aaagaaagcc | caactagatc | ctcagaaanac | 360 |
| gcttctaggg | acaataaccg | atgaagaaaa | gatggcctcc | ttgtgccccc | gtctgttatg | 420 |
| atttctctcc | attgcagcna | naaacccgtt | cttctaagca | aacncaggtg | atgatggcna | 480 |
| aaatacaccc | cctcttgaag | naccnggagg | a | | | 511 |

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73

| | | | | | |
|---|---|---|---|---|---|
| cagtgccagc | actggtgcca | gtaccagtac | caataacagt | gccagtgcca | gtgccagcac | 60 |
| cagtggtggc | ttcagtgctg | gtgccagcct | gaccgccact | ctcacatttg | ggctcttcgc | 120 |
| tggccttggt | ggagctggtg | ccagcaccag | tggcagctct | ggtgcctgtg | gtttctccta | 180 |
| caagtgagat | tttagatatt | gttaatcctg | ccagtctttc | tcttcaagcc | agggtgcatc | 240 |
| ctcagaaacc | tactcaacac | agcactctag | gcagccacta | tcaatcaatt | gaagttgaca | 300 |
| ctctgcatta | aatctatttg | ccatttctga | aaaaaaaaa | aaaaaaggg | cggccgctcg | 360 |
| antctagagg | gcccgtttaa | acccgctgat | cagcctcgac | tgtgccttct | anttgccagc | 420 |
| catctgttgt | ttgcccctcc | cccgntgcct | tccttgaccc | tggaaagtgc | cactcccact | 480 |
| gtcctttcct | aantaaaat | | | | | 499 |

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74

| | | | | | |
|---|---|---|---|---|---|
| tttcatagga | gaacacactg | aggagatact | tgaagaattt | ggattcagcc | gcgaagagat | 60 |
| ttatcagctt | aactcagata | aaatcattga | aagtaataag | gtaaaagcta | gtctctaact | 120 |
| tccaggccca | cggctcaagt | gaatttgaat | actgcattta | cagtgtagag | taacacataa | 180 |
| cattgtatgc | atggaaacat | ggaggaacag | tattacagtg | tcctaccact | ctaatcaaga | 240 |

```
aaagaattac agactctgat tctacagtga tgattgaatt ctaaaaatgg taatcattag        300
ggcttttgat ttataanact ttgggtactt atactaaatt atggtagtta tactgccttc        360
cagtttgctt gatatatttg ttgatattaa gattcttgac ttatatttg aatgggttct        420 actgaaaaan gaatgatata ttcttgaaga catcgatata catttattta cactcttgat        480
tctacaatgt agaaaatgaa ggaaatgccc caaattgtat ggtgataaaa gtcccgt          537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc        60
tgcatattac acgtacctcc tcctgctcct caagtagtgt ggtctatttt gccatcatca        120
cctgctgtct gcttagaaga acggctttct gctgcaangg agagaaatca taacagacgg        180
tggcacaagg aggccatctt ttcctcatcg gttattgtcc ctagaagcgt cttctgagga        240
tctagttggg ctttctttct gggtttgggc catttcantt ctcatgtgtg tactattcta        300
tcattattgt ataacggttt tcaaaccngt gggcacncag agaacctcac tctgtaataa        360
caatgaggaa tagccacggt gatctccagc accaaatctc tccatgttnt tccagagctc        420
ctccagccaa cccaaatagc cgctgctatn gtgtagaaca tccctgn                    467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac        60
tctctctttc tggcctggag gctatccagc gtactccaaa gattcaggtt tactcacgtc        120
atccagcaga gaatggaaag tcaaatttcc tgaattgcta tgtgtctggg tttcatccat        180
ccgacattga agttgactta ctgaagaatg gagagagaat tgaaaagtg gagcattcag        240 acttgtcttt cagcaaggac tggtcttctt atctcttgta ctacactgaa ttcaccccca        300
ctgaaaaaga tgagtatgcc tgccgtgtga accatgtgac tttgtcacag cccaagatng        360
ttnagtggga tcganacatg taagcagcan catgggaggt                            400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct        60
ccagctgccc cggcggggga tgcgaggctc ggagcaccct tgcccggctg tgattgctgc        120
caggcactgt tcatctcagc ttttctgtcc ctttgctccc ggcaagcgct tctgctgaaa        180
```

-continued gttcatatct ggagcctgat gtcttaacga ataaaggtcc catgctccac ccgaaaaaaa      240
aaaaaaaa                                                              248

<210> SEQ ID NO 78
<211> LENGTH: 201
<212> TYPE: DNA
<213> ORGANISM: Homo sapien

<400> SEQUENCE: 78
actagtccag tgtggtggaa ttccattgtg ttgggcccaa cacaatggct acctttaaca      60
tcacccagac cccgccctgc ccgtgcccca cgctgctgct aacgacagta tgatgcttac     120
tctgctactc ggaaactatt tttatgtaat taatgtatgc tttcttgttt ataaatgcct     180
gatttaaaaa aaaaaaaaaa a                                               201

210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79 tcctttttgtt aggttttga gacaacccta gacctaaact gtgtcacaga cttctgaatg      60
tttaggcagt gctagtaatt tcctcgtaat gattctgtta ttactttcct attctttatt     120
cctctttctt ctgaagatta atgaagttga aaattgaggt ggataaatac aaaaaggtag     180
tgtgatagta taagtatcta agtgcagatg aaagtgtgtt atatatatcc attcaaaatt     240
atgcaagtta gtaattactc agggttaact aaattacttt aatatgctgt tgaacctact     300
ctgttccttg gctagaaaaa attataaaca ggactttgtt agtttgggaa gccaaattga     360
taatattcta tgttctaaaa gttgggctat acataaanta tnaagaaata tggaatttta     420
ttcccaggaa tatggggttc atttatgaat antacccggg anagaagttt tgantnaaac     480
cngttttggt taatacgtta atatgtcctn aatnaacaag gcntgactta tttccaaaaa     540
aaaaaaaaaa aa                                                         552

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80
acagggattt gagatgctaa ggccccagag atcgtttgat ccaaccctct tattttcaga      60
ggggaaaatg gggcctagaa gttacagagc atctagctgg tgcgctggca ccctggcct    120 cacacagact cccgagtagc tgggactaca ggcacacagt cactgaagca ggccctgttt    180
gcaattcacg ttgccacctc aacttaaac attcttcata tgtgatgtcc ttagtcacta    240
aggtaaaact ttcccaccca gaaaggcaa cttagataaa atcttagagt actttctatac    300 tcttctaagt cctcttccag cctcactttg agtcctcctt gggggttgat aggaantntc    360
tcttggcttt ctcaataaaa tctctatcca tctcatgttt aatttggtac gcntaaaaat    420
gctgaaaaaa ttaaaatgtt ctggtttcnc tttaaaaaaa aaaaaaaaaa aaaaa         476

<210> SEQ ID NO 81
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 81

| | | | | |
|---|---|---|---|---|
| ttttttttttg | tatgccntcn | ctgtggngtt | attgttgctg | ccaccctgga ggagcccagt | 60 |
| ttcttctgta | tctttctttt | ctgggggatc | ttcctggctc | tgcccctcca ttcccagcct | 120 |
| ctcatcccca | tcttgcactt | tgctagggt | tggaggcgct | ttcctggtag cccctcagag | 180 |
| actcagtcag | cggaataag | tcctaggggt | gggggtgtg | gcaagccggc ct | 232 |

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82

| | | | | |
|---|---|---|---|---|
| aggcgggagc | agaagctaaa | gccaaagccc | aagaagagtg | gcagtgccag cactggtgcc | 60 |
| agtaccagta | ccataacat | gccagtgcca | gtgccagcac | cagtggtggc ttcagtgctg | 120 |
| gtgccagcct | gaccgccact | ctcacatttg | gctcttcgc | tggccttggt ggagctggtg | 180 |
| ccagcaccag | tggcagctct | ggtgcctgtg | gtttctccta | caagtgagat tttagatatt | 240 |
| gttaatcctg | ccagtctttc | tcttcaagcc | agggtgcatc | ctcagaaacc tactcaacac | 300 |
| agcactctng | gcagccacta | tcaatcaatt | gaagttgaca | ctctgcatta aatctatttg | 360 |
| ccatttcaaa | aaaaaaaaaa | aaa | | | 383 |

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83

| | | | | |
|---|---|---|---|---|
| accgaattgg | gaccgctggc | ttataagcga | tcatgtcctc | cagtattacc tcaacgagca | 60 |
| gggagatcga | gtctatacgc | tgaagaaatt | tgacccgatg | gacaacaga cctgctcagc | 120 |
| ccatcctgct | cggttctccc | cagatgacaa | atactctcga | caccgaatca ccatcaagaa | 180 |
| acgcttcaag | gtgctcatga | cccagcaacc | gcgcccctgtc | ctctgagggt ccttaaactg | 240 |
| atgtcttttc | tgccacctgt | tacccctcgg | agactccgta | accaaactct tcggactgtg | 300 |
| agccctgatg | ccttttttgcc | agccatactc | tttggcntcc | agtctctcgt ggcgattgat | 360 |
| tatgcttgtg | tgaggcaatc | atggtggcat | cacccatnaa | gggaacacat ttganttttt | 420 |
| tttcncatat | tttaaattac | naccagaata | nttcagaata | aatgaattga aaaactctta | 480 |
| aaaaaaaaaa | aaaa | | | | 494 |

<210> SEQ ID NO 84
<211> LENGTH: 380
<212> TYPE: DNA

<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 84

| | | | | | |
|---|---|---|---|---|---|
| gctggtagcc | tatggcgtgg | ccacggangg | gctcctgagg | cacgggacag | tgacttccca | 60 |
| agtatcctgc | gccgcgtctt | ctaccgtccc | tacctgcaga | tcttcgggca | gattccccag | 120 |
| gaggacatgg | acgtggccct | catggagcac | agcaactgct | cgtcggagcc | cggcttctgg | 180 |
| gcacaccctc | ctggggccca | ggcgggcacc | tgcgtctccc | agtatgccaa | ctggctggtg | 240 |
| gtgctgctcc | tcgtcatctt | cctgctcgtg | gccaacatcc | tgctggtcac | ttgctcattg | 300 |
| ccatgttcag | ttacacattc | ggcaaagtac | agggcaacag | cnatctctac | tgggaaggcc | 360 |
| agcgttnccg | cctcatccgg | | | | | 380 |

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85

| | | | | | |
|---|---|---|---|---|---|
| gagttagctc | ctccacaacc | ttgatgaggt | cgtctgcagt | ggcctctcgc | ttcataccgc | 60 |
| tnccatcgtc | atactgtagg | tttgccacca | cctcctgcat | cttggggcgg | ctaatatcca | 120 |
| ggaaactctc | aatcaagtca | ccgtcnatna | aacctgtggc | tggttctgtc | ttccgctcgg | 180 |
| tgtgaaagga | tctccagaag | gagtgctcga | tcttccccac | acttttgatg | actttattga | 240 |
| gtcgattctg | catgtccagc | aggaggttgt | accagctctc | tgacagtgag | gtcaccagcc | 300 |
| ctatcatgcc | nttgaacgtg | ccgaagaaca | ccgagccttg | tgtgggggt | gnagtctcac | 360 |
| ccagattctg | cattaccaga | nagccgtggc | aaaaganatt | gacaactcgc | caggnngaa | 420 |
| aaagaacacc | tcctggaagt | gctngccgct | cctcgtccnt | tggtggnngc | gcntnccttt | 480 |
| t | | | | | | 481 |

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86

| | | | | | |
|---|---|---|---|---|---|
| aacatcttcc | tgtataatgc | tgtgtaatat | cgatccgatn | ttgtctgctg | agaattcatt | 60 |
| acttggaaaa | gcaacttnaa | gcctggacac | tggtattaaa | attcacaata | tgcaacactt | 120 |
| taaacagtgt | gtcaatctgc | tcccttactt | tgtcatcacc | agtctgggaa | taagggtatg | 180 |
| ccctattcac | acctgttaaa | agggcgctaa | gcatttttga | ttcaacatct | ttttttttga | 240 |
| cacaagtccg | aaaaaagcaa | aagtaaacag | ttnttaattt | gttagccaat | tcactttctt | 300 |
| catgggacag | agccatttga | tttaaaaagc | aaattgcata | atattgagct | ttgggagctg | 360 |
| atatntgagc | ggaagantag | cctttctact | tcaccagaca | caactccttt | catattggga | 420 |
| tgttnacnaa | agttatgtct | cttacagatg | ggatgctttt | gtggcaattc | tg | 472 |

<210> SEQ ID NO 87
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87

| | | | | | | |
|---|---|---|---|---|---|---|
| agaaaccagt | atctctnaaa | acaacctctc | ataccttgtg | gacctaattt | tgtgtgcgtg | 60 |
| tgtgtgtgcg | cgcatattat | atagacaggc | acatctttt | tactttgta | aaagcttatg | 120 |
| cctctttggt | atctatatct | gtgaaagttt | taatgatctg | ccataatgtc | ttggggacct | 180 |
| ttgtcttctg | tgtaaatggt | actagagaaa | acacctatnt | tatgagtcaa | tctagttngt | 240 |
| tttattcgac | atgaaggaaa | tttccagatn | acaacactna | caaactctcc | cttgactagg | 300 |
| ggggacaaag | aaaagcanaa | ctgaacatna | gaaacaattn | cctggtgaga | aattncataa | 360 |
| acagaaattg | ggtngtatat | tgaaananng | catcattnaa | acgttttttt | ttt | 413 |

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88

| | | | | | | |
|---|---|---|---|---|---|---|
| cgcagcgggt | cctctctatc | tagctccagc | ctctcgcctg | ccccactccc | cgcgtcccgc | 60 |
| gtcctagccn | accatggccg | ggcccctgcg | cgccccgctg | ctcctgctgg | ccatcctggc | 120 |
| cgtggccctg | gccgtgagcc | ccgcggccgg | ctccagtccc | ggcaagccgc | cgcgcctggt | 180 |
| gggaggccca | tggaccccgc | gtggaagaag | aaggtgtgcg | gcgtgcactg | gactttgccg | 240 |
| tcggcnanta | caacaaaccc | gcaacnactt | ttaccnagcn | cgcgctgcag | gttgtgccgc | 300 |
| cccaancaaa | ttgttactng | gggtaantaa | ttcttggaag | ttgaacctgg | gccaaacnng | 360 |
| tttaccagaa | ccnagccaat | tngaacaatt | ncccctccat | aacagcccct | tttaaaaagg | 420 |
| gaancantcc | tgntcttttc | caaattt | | | | 448 |

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89

| | | | | | | |
|---|---|---|---|---|---|---|
| gaattttgtg | cactggccac | tgtgatggaa | ccattgggcc | aggatgcttt | gagtttatca | 60 |
| gtagtgattc | tgccaaagtt | ggtgttgtaa | catgagtatg | taaaatgtca | aaaaattagc | 120 |
| agaggtctag | gtctgcatat | cagcagacag | tttgtccgtg | tattttgtag | ccttgaagtt | 180 |
| ctcagtgaca | agttnnttct | gatgcgaagt | tctnattcca | gtgttttagt | cctttgcatc | 240 |
| tttnatgttn | agacttgcct | ctntnaaatt | gcttttgtnt | tctgcaggta | ctatctgtgg | 300 |
| tttaacaaaa | tagaannact | tctctgcttn | gaanatttga | atatcttaca | tctnaaaatn | 360 |

```
aattctctcc ccatannaaa acccangccc ttgggganaat ttgaaaaang gntccttcnn      420
aattcnnana anttcagntn tcatacaaca naacnggnac ccc                        463
```

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

```
agggattgaa ggtctnttnt actgtcggac tgttcancca ccaactctac aagttgctgt       60
cttccactca ctgtctgtaa gcntnttaac ccagactgta tcttcataaa tagaacaaat      120
tcttcaccag tcacatcttc taggaccttt ttggattcag ttagtataag ctcttccact      180
tcctttgtta agacttcatc tggtaaagtc ttaagttttg tagaaaggaa tttaattgct      240
cgttctctaa caatgtcctc tccttgaagt atttggctga acaacccacc tnaagtccct      300
ttgtgcatcc attttaaata tacttaatag ggcattggtn cactaggtta aattctgcaa      360
gagtcatctg tctgcaaaag ttgcgttagt atatctgcca                            400
```

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

```
gagctcggat ccaataatct ttgtctgagg gcagcacaca tatncagtgc catggnaact       60
ggtctacccc acatgggagc agcatgccgt agntatataa ggtcattccc tgagtcagac      120
atgcctcttt gactaccgtg tgccagtgct ggtgattctc acacacctcc nnccgctctt      180
tgtggaaaaa ctggcacttg nctggaacta gcaagacatc acttacaaat tcacccacga      240
gacacttgaa aggtgtaaca aagcgactct tgcattgctt tttgtccctc cggcaccagt      300
tgtcaatact aacccgctgg tttgcctcca tcacatttgt gatctgtagc tctggataca      360
tctcctgaca gtactgaaga acttcttctt ttgtttcaaa agcaactctt ggtgcctgtt      420
ngatcaggtt cccatttccc agtccgaatg ttcacatggc atatnttact tcccacaaaa      480
```

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

```
atacagccca natcccacca cgaagatgcg cttgttgact gagaacctga tgcggtcact       60
ggtcccgctg tagccccagc gactctccac ctgctggaag cggttgatgc tgcactcctt      120
cccacgcagg cagcagcggg gccggtcaat gaactccact cgtggcttgg ggttgacggt      180
taantgcagg aagaggctga ccacctcgcg gtccaccagg atgcccgact gtgcgggacc      240
tgcagcgaaa ctcctcgatg gtcatgagcg ggaagcgaat gangcccagg gccttgccca      300
```

```
gaaccttccg cctgttctct ggcgtcacct gcagctgctg ccgctnacac tcggcctcgg    360
accagcggac aaacggcgtt gaacagccgc acctcacgga tgcccantgt gtcgcgctcc    420
aggaacggcn ccagcgtgtc caggtcaatg tcggtgaanc ctccgcgggt aatggcg       477
```

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93

```
gaacggctgg accttgcctc gcattgtgct gctggcagga ataccttggc aagcagctcc     60
agtccgagca gccccagacc gctgccgccc gaagctaagc ctgcctctgg ccttcccctc    120
cgcctcaatg cagaaccant agtgggagca ctgtgtttag agttaagagt gaacactgtn    180
tgattttact tgggaattte ctctgttata tagcttttcc caatgctaat ttccaaacaa    240
caacaacaaa ataacatgtt tgcctgttna gttgtataaa agtangtgat tctgtatnta    300
aagaaaatat tactgttaca tatactgctt gcaanttctg tatttattgg tnctctggaa    360
ataaatatat tattaaa                                                   377
```

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94

```
ccctttgagg ggttagggtc cagttcccag tggaagaaac aggccaggag aantgcgtgc     60
cgagctgang cagatttccc acagtgaccc cagagccctg ggctatagtc tctgacccct    120
ccaaggaaag accaccttct ggggacatgg gctggagggc aggacctaga ggcaccaagg    180
gaaggcccca ttccggggct gttccccgag gaggaaggga aggggctctg tgtgccccc     240 acgaggaana ggccctgant cctgggatca nacacccctt cacgtgtatc cccacacaaa    300
tgcaagctca ccaaggtccc ctctcagtcc cttccctaca ccctgaacgg ncactggccc    360
acacccaccc agancancca cccgccatgg ggaatgtnct caaggaatcg cngggcaacg    420
tggactctng tcccnnaagg gggcagaatc tccaatagan ggannggaacc cttgctnana   480 aaaaaaaana aaaaa                                                     495
```

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95

```
ggttacttgg tttcattgcc accacttagt ggatgtcatt tagaaccatt ttgtctgctc     60
cctctggaag ccttgcgcag agcggacttt gtaattgttg gagaataact gctgaatttt    120
```

```
tagctgtttt gagttgattc gcaccactgc accacaactc aatatgaaaa ctatttnact      180
tatttattat cttgtgaaaa gtatacaatg aaaattttgt tcatactgta tttatcaagt      240
atgatgaaaa gcaatagata tatattcttt tattatgttn aattatgatt gccattatta      300
atcggcaaaa tgtggagtgt atgttctttt cacagtaata tatgcctttt gtaacttcac      360
ttggttattt tattgtaaat gaattacaaa attcttaatt taagaaaatg gtangttata      420
tttanttcan taatttcttt ccttgtttac gttaattttg aaaagaatgc at              472

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96
ctgaagcatt tcttcaaact tntctacttt tgtcattgat acctgtagta agttgacaat       60
gtggtgaaat ttcaaaatta tatgtaactt ctactagttt tactttctcc cccaagtctt      120
ttttaactca tgatttttac acacacaatc cagaacttat tatatagcct ctaagtcttt      180
attcttcaca gtagatgatg aaagagtcct ccagtgtctt gngcanaatg ttctagntat      240
agctggatac atacngtggg agttctataa actcatacct cagtgggact naaccaaaat      300
tgtgttagtc tcaattccta ccacactgag ggagcctccc aaatcactat attcttatct      360
gcaggtactc ctccagaaaa acngacaggg caggcttgca tgaaaaagtn acatctgcgt      420
tacaaagtct atcttcctca nangtctgtn aaggaacaat ttaatcttct agcttt         476

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97
actctttcta atgctgatat gatcttgagt ataagaatgc atatgtcact agaatggata       60
aaataatgct gcaaacttaa tgttcttatg caaaatggaa cgctaatgaa acacagctta      120
caatcgcaaa tcaaaactca caagtgctca tctgttgtag atttagtgta ataagactta      180
gattgtgctc cttcggatat gattgttcct canatcttgg gcaatnttcc ttagtcaaat      240
caggctacta gaattctgtt attggatatn tgagagcatg aaatttttaa naatacactt      300
gtgattatna aattaatcac aaatttcact tatacctgct atcagcagct agaaaaacat      360 ntnntttta natcaaagta ttttgtgttt ggaantgtnn aaatgaaatc tgaatgtggg      420
ttcnatctta ttttttcccn gacnactant tncttttta gggnctattc tganccatc       479

<210> SEQ ID NO 98
<211> LENGTH: 461
<212> TYPE: DNA
<213> ORGANISM: Homo sapien

<400> SEQUENCE: 98
agtgacttgt cctccaacaa aaccccttga tcaagtttgt ggcactgaca atcagaccta       60
tgctagttcc tgtcatctat tcgctactaa atgcagactg gaggggacca aaaagggggca     120
```

```
tcaactccag ctggattatt ttggagcctg caaatctatt cctacttgta cggactttga      180
agtgattcag tttcctctac ggatgagaga ctggctcaag aatatcctca tgcagcttta      240
tgaagccact ctgaacacgc tggttatcta gatgagaaca gagaaataaa gtcagaaaat      300
ttacctggag aaaagaggct ttggctgggg accatcccat gaaccttct cttaaggact       360 ttaagaaaaa ctaccacatg ttgtgtatcc tggtgccggc cgtttatgaa ctgaccaccc      420
tttggaataa tcttgacgct cctgaacttg ctcctctgcg a                         461
```

<210> SEQ ID NO 99
<211> LENGTH: 171
<212> TYPE: DNA
<213> ORGANISM: Homo sapien

<400> SEQUENCE: 99

```
gtggccgcgc gcaggtgttt cctcgtaccg cagggccccc tcccttcccc aggcgtccct      60
cggcgcctct gcgggcccga ggaggagcgg ctggcgggtg gggggagtgt gacccaccct     120
cggtgagaaa agccttctct agcgatctga gaggcgtgcc ttgggggtac c              171
```

<210> SEQ ID NO 100
<211> LENGTH: 269
<212> TYPE: DNA
<213> ORGANISM: Homo sapien

<400> SEQUENCE: 100

```
cggccgcaag tgcaactcca gctggggccg tgcggacgaa gattctgcca gcagttggtc      60
cgactgcgac gacggcggcg cgacagtcg caggtgcagc gcgggcgcct ggggtcttgc      120
aaggctgagc tgacgccgca gaggtcgtgt cacgtccac gaccttgacg ccgtcgggga      180
cagccggaac agagcccggt gaagcgggag gcctcgggga gccctcggg aagggcggcc      240 cgagagatac gcaggtgcag gtggccgcc                                        269
```

<210> SEQ ID NO 101
<211> LENGTH: 405
<212> TYPE: DNA
<213> ORGANISM: Homo sapien

<400> SEQUENCE: 101

```
tttttttttt ttttggaatc tactgcgagc acagcaggtc agcaacaagt ttattttgca      60
gctagcaagg taacagggta gggcatggtt acatgttcag gtcaacttcc tttgtcgtgg     120
ttgattggtt tgtctttatg ggggcggggt gggtagggg aaacgaagca ataacatgg       180 agtgggtgca ccctccctgt agaacctggt tacaaagctt ggggcagttc acctggtctg     240
tgaccgtcat tttcttgaca tcaatgttat tagaagtcag gatatctttt agagagtcca    300
ctgttctgga gggagattag ggtttcttgc caaatccaac aaaatccact gaaaagttg     360 gatgatcagt acgaataccg aggcatattc tcatatcggt ggcca                     405
```

<210> SEQ ID NO 102
<211> LENGTH: 470
<212> TYPE: DNA
<213> ORGANISM: Homo sapien

<400> SEQUENCE: 102

```
tttttttttt tttttttttt tttttttttt tttttttttt tttttttttt tttttttttt      60
ggcacttaat ccatttttat ttcaaaatgt ctacaaattt aatcccatta tacggtattt     120
```

| | |
|---|---|
| tcaaaatcta aattattcaa attagccaaa tccttaccaa ataatacccca aaaatcaaaa | 180 |
| atatacttct ttcagcaaac ttgttacata aattaaaaaa atatatacgg ctggtgtttt | 240 |
| caaagtacaa ttatcttaac actgcaaaca ttttaaggaa ctaaaataaa aaaaaacact | 300 |
| ccgcaaaggt taaagggaac aacaaattct tttacaacac cattataaaa atcatatctc | 360 |
| aaatcttagg ggaatatata cttcacacgg gatcttaact tttactcact ttgtttattt | 420 |
| ttttaaacca ttgtttgggc ccaacacaat ggaatccccc ctggactagt | 470 |

<210> SEQ ID NO 103
<211> LENGTH: 581
<212> TYPE: DNA
<213> ORGANISM: Homo sapien

<400> SEQUENCE: 103

| | |
|---|---|
| tttttttttt ttttttttga cccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa attttttgact cttgtaaaac atccaaattc | 240 |
| attttttcttg tctttaaaat tatctaatct ttccattttt tccctattcc aagtcaattt | 300 |
| gcttctctag cctcatttcc tagctcttat ctactattag taagtggctt ttttcctaaa | 360 |
| agggaaaaca ggaagagaaa tggcacacaa aacaaacatt ttatattcat atttctacct | 420 |
| acgttaataa aatagcattt tgtgaagcca gctcaaaaga aggcttagat cctttttatgt | 480 |
| ccattttagt cactaaacga tatcaaagtg ccagaatgca aaggtttgt gaacatttat | 540 |
| tcaaaagcta atataagata tttcacatac tcatctttct g | 581 |

<210> SEQ ID NO 104
<211> LENGTH: 578
<212> TYPE: DNA
<213> ORGANISM: Homo sapien

<400> SEQUENCE: 104

| | |
|---|---|
| tttttttttt tttttttttt tttttctctt cttttttttt gaaatgagga tcgagttttt | 60 |
| cactctctag atagggcatg aagaaaactc atctttccag ctttaaaata acaatcaaat | 120 |
| ctcttatgct atatcatatt ttaagttaaa ctaatgagtc actggcttat cttctcctga | 180 |
| aggaaatctg ttcattcttc tcattcatat agttatatca agtactacct tgcatattga | 240 |
| gaggttttttc ttctctattt acacatatat ttccatgtga atttgtatca aacctttatt | 300 |
| ttcatgcaaa ctagaaaata atgtttcttt tgcataagag aagagaacaa tatagcatta | 360 |
| caaaactgct caaattgttt gttaagttat ccattataat tagttggcag gagctaatac | 420 |
| aaatcacatt tacgacagca ataataaaac tgaagtacca gttaaatatc caaataatt | 480 |
| aaggaacat ttttagcctg ggtataatta gctaattcac tttacaagca tttattagaa | 540 |
| tgaattcaca tgttattatt cctagcccaa cacaatgg | 578 |

<210> SEQ ID NO 105
<211> LENGTH: 538
<212> TYPE: DNA
<213> ORGANISM: Homo sapien

<400> SEQUENCE: 105

| | |
|---|---|
| tttttttttt tttttcagta ataatcagaa caatatttat ttttatattt aaaattcata | 60 |
| gaaaagtgcc ttacatttaa taaaagtttg tttctcaaag tgatcagagg aattagatat | 120 |

```
gtcttgaaca ccaatattaa tttgaggaaa atacaccaaa atacattaag taaattattt    180
aagatcatag agcttgtaag tgaaaagata aaatttgacc tcagaaactc tgagcattaa    240
aaatccacta ttagcaaata aattactatg gacttcttgc tttaattttg tgatgaatat    300
ggggtgtcac tggtaaacca acacattctg aaggatacat tacttagtga tagattctta    360
tgtactttgc taatacgtgg atatgagttg acaagtttct ctttcttcaa tcttttaagg    420
ggcgagaaat gaggaagaaa agaaaaggat tacgcatact gttctttcta tggaaggatt    480
agatatgttt cctttgccaa tattaaaaaa ataataatgt ttactactag tgaaaccc     538

<210> SEQ ID NO 106
<211> LENGTH: 473
<212> TYPE: DNA
<213> ORGANISM: Homo sapien

<400> SEQUENCE: 106
tttttttttt tttttttagtc aagtttctat ttttattata attaaagtct tggtcatttc    60
atttattagc tctgcaactt acatatttaa attaaagaaa cgttttagac aactgtacaa   120
tttataaatg taaggtgcca ttattgagta atatattcct ccaagagtgg atgtgtccct   180
tctcccacca actaatgaac agcaacatta gtttaattttt attagtagat atacactgct   240
gcaaacgcta attctcttct ccatccccat gtgatattgt gtatatgtgt gagttggtag   300
aatgcatcac aatctacaat caacagcaag atgaagctag gctgggcttt cggtgaaaat   360
agactgtgtc tgtctgaatc aaatgatctg acctatcctc ggtggcaaga actcttcgaa   420
ccgcttcctc aaaggcgctg ccacatttgt ggctctttgc acttgtttca aaa           473

<210> SEQ ID NO 107
<211> LENGTH: 1621
<212> TYPE: DNA
<213> ORGANISM: Homo sapien

<400> SEQUENCE: 107
cgccatggca ctgcagggca tctcggtcat ggagctgtcc ggcctggccc cgggcccgtt    60
ctgtgctatg gtcctggctg acttcggggc gcgtgtggta cgcgtggacc ggcccggctc   120
ccgctacgac gtgagccgct tgggccgggg caagcgctcg ctagtgctgg acctgaagca   180
gccgcgggga gccgccgtgc tgcggcgtct gtgcaagcgg tcggatgtgc tgctggagcc   240
cttccgccgc ggtgtcatgg agaaactcca gctgggccca gagattctgc agcgggaaaa   300
tccaaggctt atttatgcca ggctgagtgg atttggccag tcaggaagct tctgccggtt   360
agctggccac gatatcaact atttggcttt gtcaggtgtt ctctcaaaaa ttggcagaag   420
tggtgagaat ccgtatgccc cgctgaatct cctggctgac tttgctggtg gtggccttat   480
gtgtgcactg gcattataa tggctctttt tgaccgcaca cgcactgaca agggtcaggt   540
cattgatgca aatatggtgg aaggaacagc atatttaagt tcttttctgt ggaaaactca   600
gaaatcgagt ctgtgggaag cacctcgagg acagaacatg ttggatggtg agcacccttt   660
ctatacgact tacaggacag cagatgggga attcatggct gttggagcaa tagaaccca   720 gttctacagag ctgctgatca aaggacttgg actaaagtct gatgaacttc ccaatcagat   780
gagcatggat gattggccag aaatgaagaa gaagtttgca gatgtatttg caaagaagac   840
gaaggcagag tggtgtcaaa tctttgacgg cacagatgcc tgtgtgactc cggttctgac   900
ttttgaggag gttgttcatc atgatcacaa caaggaacgg ggctcgttta tcaccagtga   960
```

-continued

```
ggagcaggac gtgagccccc gccctgcacc tctgctgtta acacccccag ccatcccttc   1020
tttcaaaagg gatcctttca taggagaaca cactgaggag atacttgaag aatttggatt   1080
cagccgcgaa gagatttatc agcttaactc agataaaatc attgaaagta ataaggtaaa   1140
agctagtctc taacttccag gcccacggct caagtgaatt tgaatactgc atttacagtg   1200
tagagtaaca cataacattg tatgcatgga aacatggagg aacagtatta cagtgtccta   1260
ccactctaat caagaaaaga attacagact ctgattctac agtgatgatt gaattctaaa   1320
aatggttatc attagggctt ttgatttata aactttggg tacttatact aaattatggt    1380
agttattctg ccttccagtt tgcttgatat atttgttgat attaagattc ttgacttata   1440
ttttgaatgg gttctagtga aaaggaatg atatattctt gaagacatcg atatacattt    1500
atttacactc ttgattctac aatgtagaaa atgaggaaat gccacaaatt gtatggtgat   1560
aaaagtcacg tgaaacaaaa aaaaaaaaaa aaaaaaaaaa aaaaaaaaaa aaaaaaaaaa   1620
a                                                                  1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
                20                  25                  30

Arg Val Asp Arg Pro Gly Ser Arg Tyr Asp Val Ser Arg Leu Gly Arg
            35                  40                  45

Gly Lys Arg Ser Leu Val Leu Asp Leu Lys Gln Pro Arg Gly Ala Ala
        50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255
```

-continued

```
Asn Gln Met Ser Met Asp Asp Trp Pro Glu Met Lys Lys Phe Ala
            260                 265                 270
Asp Val Phe Ala Lys Lys Thr Lys Ala Glu Trp Cys Gln Ile Phe Asp
        275                 280                 285
Gly Thr Asp Ala Cys Val Thr Pro Val Leu Thr Phe Glu Glu Val Val
        290                 295                 300
His His Asp His Asn Lys Glu Arg Gly Ser Phe Ile Thr Ser Glu Glu
305                 310                 315                 320
Gln Asp Val Ser Pro Arg Pro Ala Pro Leu Leu Leu Asn Thr Pro Ala
                325                 330                 335
Ile Pro Ser Phe Lys Arg Asp Pro Phe Ile Gly Glu His Thr Glu Glu
                340                 345                 350
Ile Leu Glu Glu Phe Gly Phe Ser Arg Glu Glu Ile Tyr Gln Leu Asn
                355                 360                 365
Ser Asp Lys Ile Ile Glu Ser Asn Lys Val Lys Ala Ser Leu
            370                 375                 380
```

<210> SEQ ID NO 109
<211> LENGTH: 1524
<212> TYPE: DNA
<213> ORGANISM: Homo sapien

<400> SEQUENCE: 109

```
ggcacgaggc tgcgccaggg cctgagcgga ggcggggggca gcctcgccag cgggggcccc    60
gggcctggcc atgcctcact gagccagcgc ctgcgcctct acctcgccga cagctggaac   120
cagtgcgacc tagtggctct cacctgcttc ctcctgggcg tgggctgccg gctgaccccg   180
ggtttgtacc acctgggccg cactgtcctc tgcatcgact tcatggtttt cacggtgcgg   240
ctgcttcaca tcttcacggt caacaaacag ctggggccca agatcgtcat cgtgagcaag   300
atgatgaagg acgtgttctt cttcctcttc ttcctcggcg tgtggctggt agcctatggc   360
gtggccacgg aggggctcct gaggccacgg gacagtgact cccaagtat cctgcgccgc   420
gtcttctacc gtccctacct gcagatcttc gggcagattc cccaggagga catggacgtg   480
gccctcatgg agcacagcaa ctgctcgtcg gagcccggct ctgggcaca ccctcctggg   540
gcccaggcgg gcacctgcgt ctcccagtat gccaactggc tggtggtgct gctcctcgtc   600
atcttcctgc tcgtggccaa catcctgctg tcaacttgc tcattgccat gttcagttac   660
acattcggca agtacagggg caacagcgat ctctactgga aggcgcagcg ttaccgcctc   720
atccgggaat ccactctcg gcccgcgctg gccccgccct ttatcgtcat ctcccacttg   780
cgcctcctgc tcaggcaatt gtgcaggcga ccccggagcc cccagccgtc ctccccggcc   840
ctcgagcatt ccgggtttta cctttctaag gaagccgagc ggaagctgct aacgtgggaa   900
tcggtgcata aggagaactt tctgctggca cgcgctaggg acaagcggga gagcgactcc   960
gagcgtctga gcgcacgtc ccagaaggtg gacttggcac tgaaacagct gggacacatc  1020
cgcgagtacg aacagcgcct gaaagtgctg agcgggagg tccagcagtg tagccgcgtc  1080
ctggggtggg tggccgaggc cctgagccgc tctgccttgc tgccccagg tgggccgcca  1140
cccccctgacc tgcctgggtc caaagactga gccctgctgg cggacttcaa ggagaagccc  1200
ccacagggga ttttgctcct agagtaaggc tcatctgggc ctcggccccc gcacctggtg  1260
gccttgtcct tgaggtgagc cccatgtcca tctgggccac tgtcaggacc acctttggga  1320
gtgtcatcct tacaaaccac agcatgcccg gctcctccca gaaccagtcc cagcctggga  1380
```

-continued

| | |
|---|---|
| ggatcaaggc ctggatcccg ggccgttatc catctggagg ctgcaggtc cttggggtaa | 1440 |
| cagggaccac agacccctca ccactcacag attcctcaca ctggggaaat aaagccattt | 1500 |
| cagaggaaaa aaaaaaaaaa aaaa | 1524 |

<210> SEQ ID NO 110
<211> LENGTH: 3410
<212> TYPE: DNA
<213> ORGANISM: Homo sapien

<400> SEQUENCE: 110

| | |
|---|---|
| gggaaccagc ctgcacgcgc tggctccggg tgacagccgc gcgcctcggc caggatctga | 60 |
| gtgatgagac gtgtccccac tgaggtgccc cacagcagca ggtgttgagc atgggctgag | 120 |
| aagctggacc ggcaccaaag ggctggcaga atgggcgcc tggctgattc ctaggcagtt | 180 |
| ggcggcagca aggaggagag gccgcagctt ctggagcaga gccgagacga agcagttctg | 240 |
| gagtgcctga acggccccct gagccctacc cgcctggccc actatggtcc agaggctgtg | 300 |
| ggtgagccgc ctgctgcggc accggaaagc ccagctcttg ctggtcaacc tgctaacctt | 360 |
| tggcctggag gtgtgtttgg ccgcaggcat cacctatgtg ccgcctctgc tgctggaagt | 420 |
| gggggtagag gagaagttca tgaccatggt gctgggcatt ggtccagtgc tgggcctggt | 480 |
| ctgtgtcccg ctcctaggct cagccagtga ccactggcgt ggacgctatg gccgccgccg | 540 |
| gcccttcatc tggcactgt ccttgggcat cctgctgagc ctctttctca tcccaagggc | 600 |
| cggctggcta gcagggctgc tgtgcccgga tcccaggccc ctggagctgg cactgctcat | 660 |
| cctgggcgtg gggctgctgg acttctgtgg ccaggtgtgc ttcactccac tggaggccct | 720 |
| gctctctgac ctcttccggg accggaccac ctgtcgccag gcctactctg tctatgcctt | 780 |
| catgatcagt cttgggggct gcctgggcta cctcctgcct gccattgact gggacaccag | 840 |
| tgccctggcc ccctacctgg gcacccagga ggagtgcctc tttggcctgc tcaccctcat | 900 |
| cttcctcacc tgcgtagcag ccacactgct ggtggctgag gaggcagcgc tgggccccac | 960 |
| cgagccagca gaagggctgt cggcccctc cttgtcgccc cactgctgtc catgccgggc | 1020 |
| ccgcttggct ttccggaacc tgggcgccct gcttccccgg ctgcaccagc tgtgctgccg | 1080 |
| catgccccgc accctgcgcc ggctcttcgt ggctgagctg tgcagctgga tggcactcat | 1140 |
| gaccttcacg ctgtttttaca cggatttcgt gggcgagggg ctgtaccagg gcgtgcccag | 1200 |
| agctgagccg ggcaccgagg cccggagaca ctatgatgaa ggcgttcgga tgggcagcct | 1260 |
| ggggctgttc ctgcagtgcg ccatctccct ggtcttctct ctggtcatgg accggctggt | 1320 |
| gcagcgattc ggcactcgag cagtctattt ggccagtgtg cagcttttcc ctgtggctgc | 1380 |
| cggtgccaca tgcctgtccc acagtgtggc cgtggtgaca gcttcagccg ccctcaccgg | 1440 |
| gttcaccttc tcagccctgc agatcctgcc ctacacactg gcctccctct accaccggga | 1500 |
| gaagcaggtg ttcctgccca ataccgaggg gacactggag gtgctagca gtgaggacag | 1560 |
| cctgatgacc agcttcctgc caggcccctaa gcctggagct cccttcccta atggacacgt | 1620 |
| gggtgctgga ggcagtggcc tgctcccacc tccacccgcg ctctgcgggg cctctgcctg | 1680 |
| tgatgtctcc gtacgtgtgg tggtgggtga gccaccgag gccagggtgg ttccgggccg | 1740 |
| gggcatctgc ctggacctcg ccatcctgga tagtgccttc ctgctgtccc aggtggcccc | 1800 |
| atccctgttt atgggctcca ttgtccagct cagccagtct gtcactgcct atatggtgtc | 1860 |
| tgccgcaggc ctggtctgg tcgccatttta ctttgctaca caggtagtat ttgacaagag | 1920 |
| cgacttggcc aaatactcag cgtagaaaac ttccagcaca ttggggtgga gggcctgcct | 1980 |

-continued

```
cactgggtcc cagctcccg ctcctgttag ccccatgggg ctgccgggct ggccgccagt    2040
ttctgttgct gccaaagtaa tgtggctctc tgctgccacc ctgtgctgct gaggtgcgta    2100
gctgcacagc tgggggctgg ggcgtccctc tcctctctcc ccagtctcta gggctgcctg    2160
actggaggcc ttccaagggg gtttcagtct ggacttatac agggaggcca gaagggctcc    2220
atgcactgga atgcgggac tctgcaggtg gattacccag gctcagggtt aacagctagc     2280
ctcctagttg agacacacct agagaagggt ttttgggagc tgaataaact cagtcacctg    2340
gtttcccatc tctaagcccc ttaacctgca gcttcgttta atgtagctct tgcatgggag    2400
tttctaggat gaaacactcc tccatgggat ttgaacatat gacttatttg taggggaaga    2460
gtcctgaggg gcaacacaca agaaccaggt cccctcagcc cacagcactg tcttttttgct   2520 gatccacccc cctcttacct tttatcagga tgtggcctgt tggtccttct gttgccatca    2580
cagagacaca ggcatttaaa tatttaactt atttatttaa caagtagaa gggaatccat     2640 tgctagcttt tctgtgttgg tgtctaatat ttgggtaggg tggggatcc ccaacaatca     2700 ggtcccctga gatagctggt cattgggctg atcattgcca gaatcttctt ctcctggggt    2760
ctggcccccc aaaatgccta acccaggacc ttggaaattc tactcatccc aaatgataat    2820
tccaaatgct gttacccaag gttagggtgt tgaaggaagg tagagggtgg ggcttcaggt    2880
ctcaacggct tccctaacca cccctcttct cttggcccag cctggttccc cccacttcca    2940 ctccctcta ctctctctag gactgggctg atgaaggcac tgcccaaaat ttcccctacc     3000
cccaactttc ccctaccccc aactttcccc accagctcca caaccctgtt tggagctact    3060
gcaggaccag aagcacaaag tgcggtttcc caagcctttg tccatctcag cccccagagt    3120
atatctgtgc ttggggaatc tcacacagaa actcaggagc accccctgcc tgagctaagg    3180
gaggtcttat ctctcagggg gggtttaagt gccgtttgca ataatgtcgt cttatttatt    3240
tagcggggtg aatattttat actgtaagtg agcaatcaga gtataatgtt tatggtgaca    3300
aaattaaagg ctttcttata tgtttaaaaa aaaaaaaaa aaaaaaaaa aaaaaaaaa       3360 aaaaaaaara aaaaaaaaaa aaaaaaaaaa aaaaaataa aaaaaaaaa                 3410
```

<210> SEQ ID NO 111
<211> LENGTH: 1289
<212> TYPE: DNA
<213> ORGANISM: Homo sapien

<400> SEQUENCE: 111

```
agccaggcgt ccctctgcct gcccactcag tggcaacacc cgggagctgt tttgtccttt     60
gtggagcctc agcagttccc tctttcagaa ctcactgcca agagccctga acaggagcca    120
ccatgcagtg cttcagcttc attaagacca tgatgatcct cttcaatttg ctcatctttc    180
tgtgtggtgc agccctgttg gcagtgggca tctgggtgtc aatcgatggg gcatcctttc    240
tgaagatctt cgggccactg tcgtccagtg ccatgcagtt tgtcaacgtg gctacttcc     300 tcatcgcagc cggcgttgtg gtctttgctc ttggttttcct gggctgctat ggtgctaaga    360
ctgagagcaa gtgtgccctc gtgacgttct tcttcatcct cctcctcatc ttcattgctg    420
aggttgcagc tgctgtggtc gccttggtgt acaccacaat ggctgagcac ttcctgacgt    480
tgctggtagt gcctgccatc aagaaagatt atggttccca ggaagacttc actcaagtgt    540
ggaacaccac catgaaaggg ctcaagtgct gtggcttcac caactatcg gattttgagg     600 actcacccta cttcaaagag aacagtgcct ttccccccatt ctgttgcaat gacaacgtca   660
```

-continued

```
ccaacacagc caatgaaacc tgcaccaagc aaaaggctca cgaccaaaaa gtagagggtt    720
gcttcaatca gcttttgtat gacatccgaa ctaatgcagt caccgtgggt ggtgtggcag    780
ctggaattgg gggcctcgag ctggctgcca tgattgtgtc catgtatctg tactgcaatc    840
tacaataagt ccacttctgc ctctgccact actgctgcca catgggaact gtgaagaggc    900
accctggcaa gcagcagtga ttgggggagg ggacaggatc taacaatgtc acttgggcca    960
gaatggacct gcccttctg ctccagactt ggggctagat agggaccact ccttttagcg   1020
atgcctgact ttccttccat tggtgggtgg atgggtgggg ggcattccag agcctctaag   1080
gtagccagtt ctgttgccca ttcccccagt ctattaaacc cttgatatgc ccctaggcc    1140 tagtggtgat cccagtgctc tactggggga tgagagaaag gcatttata gcctgggcat    1200 aagtgaaatc agcagagcct ctgggtggat gtgtagaagg cacttcaaaa tgcataaacc   1260
tgttacaatg ttaaaaaaaa aaaaaaaa                                       1289
```

210> SEQ ID NO 112
<211> LENGTH:315
<212> TYPE:PRT
<213> ORGNISM: Homo sapien

<400> SEQUENCE: 112

```
Met Val Phe Thr Val Arg Leu Leu His Ile Phe Thr Val Asn Lys Gln
 1               5                   10                  15

Leu Gly Pro Lys Ile Val Ile Val Ser Lys Met Met Lys Asp Val Phe
            20                  25                  30

Phe Phe Leu Phe Phe Leu Gly Val Trp Leu Val Ala Tyr Gly Val Ala
        35                  40                  45

Thr Glu Gly Leu Leu Arg Pro Arg Asp Ser Asp Phe Pro Ser Ile Leu
    50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
```

-continued

```
                260                 265                 270
Leu Lys Val Leu Glu Arg Glu Val Gln Gln Cys Ser Arg Val Leu Gly
            275                 280                 285

Trp Val Ala Glu Ala Leu Ser Arg Ser Ala Leu Leu Pro Pro Gly Gly
        290                 295                 300

Pro Pro Pro Pro Asp Leu Pro Gly Ser Lys Asp
305                 310                 315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Arg His Arg Lys Ala
1               5                   10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Leu Glu Val Gly Val
            35                  40                  45

Glu Glu Lys Phe Met Thr Met Val Leu Gly Ile Gly Pro Val Leu Gly
50                  55                  60

Leu Val Cys Val Pro Leu Leu Gly Ser Ala Ser Asp His Trp Arg Gly
65                  70                  75                  80

Arg Tyr Gly Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
            100                 105                 110

Leu Cys Pro Asp Pro Arg Pro Leu Glu Leu Ala Leu Ile Leu Gly
            115                 120                 125

Val Gly Leu Leu Asp Phe Cys Gly Gln Val Cys Phe Thr Pro Leu Glu
130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
        195                 200                 205

Thr Cys Val Ala Ala Thr Leu Leu Val Ala Glu Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Leu Ala Phe Arg Asn Leu Gly Ala Leu
                245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
            275                 280                 285

Thr Leu Phe Tyr Thr Asp Phe Val Gly Glu Gly Leu Tyr Gln Gly Val
        290                 295                 300

Pro Arg Ala Glu Pro Gly Thr Glu Ala Arg His Tyr Asp Glu Gly
305                 310                 315                 320
```

```
Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
            340                 345                 350

Ala Val Tyr Leu Ala Ser Val Ala Ala Phe Pro Val Ala Ala Gly Ala
        355                 360                 365

Thr Cys Leu Ser His Ser Val Ala Val Thr Ala Ser Ala Ala Leu
    370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
        435                 440                 445

Gly Gly Ser Gly Leu Leu Pro Pro Pro Ala Leu Cys Gly Ala Ser
    450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
        515                 520                 525

Gly Leu Gly Leu Val Ala Ile Tyr Phe Ala Thr Gln Val Val Phe Asp
    530                 535                 540

Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
1               5                   10                  15

Leu Ile Phe Leu Cys Gly Ala Ala Leu Leu Ala Val Gly Ile Trp Val
            20                  25                  30

Ser Ile Asp Gly Ala Ser Phe Leu Lys Ile Phe Gly Pro Leu Ser Ser
        35                  40                  45

Ser Ala Met Gln Phe Val Asn Val Gly Tyr Phe Leu Ile Ala Ala Gly
    50                  55                  60

Val Val Phe Ala Leu Gly Phe Leu Gly Cys Tyr Gly Ala Lys Thr
65                  70                  75                  80

Glu Ser Lys Cys Ala Leu Val Thr Phe Phe Phe Ile Leu Leu Leu Ile
                85                  90                  95

Phe Ile Ala Glu Val Ala Ala Ala Val Val Ala Leu Val Tyr Thr Thr
            100                 105                 110

Met Ala Glu His Phe Leu Thr Leu Leu Val Val Pro Ala Ile Lys Lys
        115                 120                 125

Asp Tyr Gly Ser Gln Glu Asp Phe Thr Gln Val Trp Asn Thr Thr Met
    130                 135                 140
```

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
            165                 170                 175

Asp Asn Val Thr Asn Thr Ala Asn Glu Thr Cys Thr Lys Gln Lys Ala
        180                 185                 190

His Asp Gln Lys Val Glu Gly Cys Phe Asn Gln Leu Leu Tyr Asp Ile
        195                 200                 205

Arg Thr Asn Ala Val Thr Val Gly Gly Val Ala Gly Ile Gly Gly
    210                 215                 220

Leu Glu Leu Ala Ala Met Ile Val Ser Met Tyr Leu Tyr Cys Asn Leu
225                 230                 235                 240

Gln

<210> SEQ ID NO 115
<211> LENGTH: 366
<212> TYPE: DNA
<213> ORGANISM: Homo sapien

<400> SEQUENCE: 115

| | | | | | |
|---|---|---|---|---|---|
| gctctttctc | tccctcctc | tgaatttaat | tctttcaact | tgcaatttgc | aaggattaca | 60 |
| catttcactg | tgatgtatat | tgtgttgcaa | aaaaaaaaaa | gtgtctttgt | ttaaaattac | 120 |
| ttggtttgtg | aatccatctt | gcttttttccc | cattggaact | agtcattaac | ccatctctga | 180 |
| actggtagaa | aaacatctga | agagctagtc | tatcagcatc | tgacaggtga | attggatggt | 240 |
| tctcagaacc | atttcaccca | gacagcctgt | ttctatcctg | tttaataaat | tagtttgggt | 300 |
| tctctacatg | cataacaaac | cctgctccaa | tctgtcacat | aaaagtctgt | gacttgaagt | 360 |
| ttagtc | | | | | | 366 |

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116

| | | | | | |
|---|---|---|---|---|---|
| acaaagatga | accatttcct | atattatagc | aaaattaaaa | tctacccgta | ttctaatatt | 60 |
| gagaaatgag | atnaaacaca | atnttataaa | gtctacttag | agaagatcaa | gtgacctcaa | 120 |
| agactttact | attttcatat | tttaagacac | atgatttatc | ctattttagt | aacctggttc | 180 |
| atacgttaaa | caaaggataa | tgtgaacagc | agagaggatt | tgttggcaga | aaatctatgt | 240 |
| tcaatctnga | actatctana | tcacagacat | ttctattcct | tt | | 282 |

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117

| | | | | | |
|---|---|---|---|---|---|
| acacatgtcg | cttcactgcc | ttcttagatg | cttctggtca | acatanagga | acagggacca | 60 |

```
tatttatcct ccctcctgaa acaattgcaa aataanacaa aatatatgaa acaattgcaa      120
aataaggcaa aatatatgaa acaacaggtc tcgagatatt ggaaatcagt caatgaagga      180
tactgatccc tgatcactgt cctaatgcag gatgtgggaa acagatgagg tcacctctgt      240
gactgcccca gcttactgcc tgtagagagt ttctangctg cagttcagac agggagaaat      300
tgggt                                                                 305
```

```
<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118
```

```
accaaggtgt ntgaatctct gacgtgggga tctctgattc ccgcacaatc tgagtggaaa      60
aantcctggg t                                                          71
```

```
<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119
```

```
actccggttg gtgtcagcag cacgtggcat tgaacatngc aatgtggagc ccaaaccaca      60
gaaaatgggg tgaaattggc caactttcta tnaacttatg ttggcaantt tgccaccaac     120
agtaagctgg cccttctaat aaaagaaaat tgaaaggttt ctcactaanc ggaattaant     180
aatggantca aganactccc aggcctcagc gt                                   212
```

```
<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120
```

```
actcgttgca natcaggggc cccccagagt caccgttgca ggagtccttc tggtcttgcc      60
ctccgccggc gcagaacatg ctggggtggt                                      90
```

```
<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121
```

```
tgtancgtga anacgacaga nagggttgtc aaaaatggag aanccttgaa gtcattttga      60
gaataagatt tgctaaaaga tttggggcta aaacatggtt attgggagac atttctgaag     120
atatncangt aaaattangga atgaattcat ggttctttg ggaattcctt tacgatngcc     180
```

```
agcatanact tcatgtgggg atancagcta cccttgta                              218
```

<210> SEQ ID NO 122
<211> LENGTH: 171
<212> TYPE: DNA
<213> ORGANISM: Homo sapien

<400> SEQUENCE: 122

```
tagggtgta tgcaactgta aggacaaaaa ttgagactca actggcttaa ccaataaagg        60
catttgttag ctcatggaac aggaagtcgg atggtgggc atcttcagtg ctgcatgagt       120
caccaccccg gcgggtcat ctgtgccaca ggtccctgtt gacagtgcgg t                171
```

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123

```
tgtagcgtga agacnacaga atggtgtgtg ctgtgctatc caggaacaca tttattatca       60
ttatcaanta ttgtgt                                                       76
```

<210> SEQ ID NO 124
<211> LENGTH: 131
<212> TYPE: DNA
<213> ORGANISM: Homo sapien

<400> SEQUENCE: 124

```
acctttcccc aaggccaatg tcctgtgtgc taactggccg gctgcaggac agctgcaatt       60
caatgtgctg ggtcatatgg agggaggag actctaaaat agccaatttt attctcttgg      120
ttaagatttg t                                                           131
```

<210> SEQ ID NO 125
<211> LENGTH: 432
<212> TYPE: DNA
<213> ORGANISM: Homo sapien

<400> SEQUENCE: 125

```
actttatcta ctggctatga aatagatggt ggaaaattgc gttaccaact ataccactgg       60
cttgaaaaag aggtgatagc tcttcagagg acttgtgact tttgctcaga tgctgaagaa      120
ctacagtctg catttggcag aaatgaagat gaatttggat taaatgagga tgctgaagat      180
ttgcctcacc aaacaaaagt gaaacaactg agagaaaatt ttcaggaaaa agacagtgg       240 ctcttgaagt atcagtcact tttgagaatg tttcttagtt actgcatact tcatggatcc      300
catggtgggg gtcttgcatc tgtaagaatg gaattgattt tgcttttgca agaatctcag      360
caggaaacat cagaaccact attttctagc cctctgtcag agcaaacctc agtgcctctc      420
ctctttgctt gt                                                         432
```

<210> SEQ ID NO 126
<211> LENGTH: 112
<212> TYPE: DNA
<213> ORGANISM: Homo sapien

<400> SEQUENCE: 126

```
acacaacttg aatagtaaaa tagaaactga gctgaaattt ctaattcact ttctaaccat    60
agtaagaatg atatttcccc ccagggatca ccaaatattt ataaaaattt gt          112
```

<210> SEQ ID NO 127
<211> LENGTH: 54
<212> TYPE: DNA
<213> ORGANISM: Homo sapien

<400> SEQUENCE: 127

```
accacgaaac cacaaacaag atggaagcat caatccactt gccaagcaca gcag          54
```

<210> SEQ ID NO 128
<211> LENGTH: 323
<212> TYPE: DNA
<213> ORGANISM: Homo sapien

<400> SEQUENCE: 128

```
acctcattag taattgtttt gttgtttcat ttttttctaa tgtctcccct ctaccagctc    60
acctgagata acagaatgaa aatggaagga cagccagatt tctcctttgc tctctgctca   120
ttctctctga agtctaggtt acccattttg gggacccatt ataggcaata aacacagttc   180
ccaaagcatt tggacagttt cttgttgtgt tttagaatgg ttttcctttt tcttagcctt   240
ttcctgcaaa aggctcactc agtcccttgc ttgctcagtg gactgggctc cccagggcct   300
aggctgcctt cttttccatg tcc                                          323
```

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

```
acatacatgt gtgtatattt ttaaatatca cttttgtatc actctgactt tttagcatac    60
tgaaaacaca ctaacataat ttntgtgaac catgatcaga tacaacccaa atcattcatc   120
tagcacattc atctgtgata naaagatagg tgagtttcat ttccttcacg ttggccaatg   180
gataaacaaa gt                                                      192
```

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

```
ccctttttta tggaatgagt agactgtatg tttgaanatt tanccacaac ctctttgaca    60
tataatgacg caacaaaaag gtgctgttta gtcctatggt tcagtttatg cccctgacaa   120
gtttccattg tgttttgccg atcttctggc taatcgtggt atcctccatg ttattagtaa   180
ttctgtattc cattttgtta acgcctggta gatgtaacct gctangaggc taactttata   240
cttatttaaa agctcttatt ttgtggtcat taaaatggca atttatgtgc agcactttat   300
tgcagcagga agcacgtgtg ggttggttgt aaagctcttt gctaatctta aaaagtaatg   360
gg                                                                 362
```

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

```
cttttgaaa gatcgtgtcc actcctgtgg acatcttgtt ttaatggagt ttcccatgca      60
gtangactgg tatggttgca gctgtccaga taaaaacatt tgaagagctc caaaatgaga     120
gttctcccag gttcgccctg ctgctccaag tctcagcagc agcctctttt aggaggcatc    180
ttctgaacta gattaaggca gcttgtaaat ctgatgtgat ttggtttatt atccaactaa    240
cttccatctg ttatcactgg agaaagccca gactccccan gacnggtacg gattgtgggc    300
atanaaggat tgggtgaagc tggcgttgtg gt                                  332
```

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

```
acttttgcca ttttgtatat ataaacaatc ttgggacatt ctcctgaaaa ctaggtgtcc     60
agtggctaag agaactcgat ttcaagcaat tctgaaagga aaccagcat gacacagaat     120
ctcaaattcc caaacagggg ctctgtggga aaatgaggg aggacctttg tatctcgggt    180
tttagcaagt taaatgaan atgacaggaa aggcttattt atcaacaaag agaagagttg    240
ggatgcttct aaaaaaaact ttggtagaga aaataggaat gctnaatcct agggaagcct    300
gtaacaatct acaattggtc ca                                            322
```

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

```
acaagccttc acaagtttaa ctaaattggg attaatcttt ctgtanttat ctgcataatt     60
cttgtttttc tttccatctg gctcctgggt tgacaatttg tggaaacaac tctattgcta    120
ctatttaaaa aaaatcacaa atctttccct ttaagctatg ttnaattcaa actattcctg    180
ctattcctgt tttgtcaaag aaattatatt tttcaaaata tgtntatttg tttgatgggt    240
cccacgaaac actaataaaa accacagaga ccagcctg                            278
```

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)

<223> OTHER INFORMATION: n = A,T,C or G

<400> SEQUENCE: 134

```
gtttanaaaa cttgtttagc tccatagagg aaagaatgtt aaactttgta ttttaaaaca      60
tgattctctg aggttaaact tggttttcaa atgttatttt tacttgtatt ttgcttttgg     120
t                                                                    121
```

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135

```
acttanaacc atgcctagca catcagaatc cctcaaagaa catcagtata atcctatacc      60
atancaagtg gtgactggtt aagcgtgcga caaaggtcag ctggcacatt acttgtgtgc     120
aaacttgata cttttgttct aagtaggaac tagtatacag tncctaggan tggtactcca    180
gggtgccccc caactcctgc agccgctcct ctgtgccagn ccctgnaagg aactttcgct    240
ccacctcaat caagccctgg gccatgctac ctgcaattgg ctgaacaaac gtttgctgag    300
ttcccaagga tgcaaagcct ggtgctcaac tcctggggcg tcaactcagt               350
```

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136

```
tgtaccgtga agacgacaga agttgcatgg cagggacagg gcaggccga ggccagggtt      60
gctgtgattg tatccgaata ntcctcgtga gaaagataa tgagatgacg tgagcagcct     120
gcagacttgt gtctgccttc aanaagccag acaggaaggc cctgcctgcc ttggctctga    180
cctggcggcc agccagccag ccacaggtgg gcttcttcct tttgtggtga caacnccaag    240
aaaactgcag aggcccaggg tcaggtgtna gtgggtangt gaccataaaa caccaggtgc    300
tcccaggaac ccgggcaaag gccatcccca cctacagcca gcatgccac tggcgtgatg    360
ggtgcagang gatgaagcag ccagntgttc tgctgtggt                           399
```

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137

```
actggtgtgg tngggggtga tgctggtggt anaagttgan gtgacttcan gatggtgtgt      60
ggaggaagtg tgtgaacgta gggatgtaga ngttttggcc gtgctaaatg agcttcggga    120
ttggctggtc ccactggtgg tcactgtcat tggtggggtt cctgt                    165
```

<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138

| | | | | | |
|---|---|---|---|---|---|
| actcactgga | atgccacatt | cacaacagaa | tcagaggtct | gtgaaaacat | taatggctcc | 60 |
| ttaacttctc | cagtaagaat | cagggacttg | aaatggaaac | gttaacagcc | acatgcccaa | 120 |
| tgctgggcag | tctcccatgc | cttccacagt | gaaagggctt | gagaaaaatc | acatccaatg | 180 |
| tcatgtgttt | ccagccacac | caaaaggtgc | ttggggtgga | gggctggggg | catananggt | 240 |
| cangcctcag | gaagcctcaa | gttccattca | gctttgccac | tgtacattcc | ccatntttaa | 300 |
| aaaaactgat | gccttttttt | tttttttttg | taaaattc | | | 338 |

<210> SEQ ID NO 139
<211> LENGTH: 382
<212> TYPE: DNA
<213> ORGANISM: Homo sapien

<400> SEQUENCE: 139

| | | | | | |
|---|---|---|---|---|---|
| gggaatcttg | gttttggca | tctggtttgc | ctatagccga | ggccactttg | acagaacaaa | 60 |
| gaaagggact | tcgagtaaga | aggtgattta | cagccagcct | agtgcccgaa | gtgaaggaga | 120 |
| attcaaacag | acctcgtcat | tcctggtgtg | agcctggtcg | gctcaccgcc | tatcatctgc | 180 |
| atttgcctta | ctcaggtgct | accggactct | ggccctgat | gtctgtagtt | tcacaggatg | 240 |
| ccttatttgt | cttctacacc | ccacagggcc | ccctacttct | tcggatgtgt | ttttaataat | 300 |
| gtcagctatg | tgccccatcc | tccttcatgc | cctccctccc | tttcctacca | ctgctgagtg | 360 |
| gcctggaact | tgtttaaagt | gt | | | | 382 |

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140

| | | | | | |
|---|---|---|---|---|---|
| accaaanctt | ctttctgttg | tgttngattt | tactataggg | gtttngcttn | ttctaaanat | 60 |
| acttttcatt | taacancttt | tgttaagtgt | caggctgcac | tttgctccat | anaattattg | 120 |
| ttttcacatt | tcaacttgta | tgtgtttgtc | tcttanagca | ttggtgaaat | cacatatttt | 180 |
| atattcagca | taaaggagaa | | | | | 200 |

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141

| | | | | | |
|---|---|---|---|---|---|
| actttatttt | caaaacactc | atatgttgca | aaaaacacat | agaaaaataa | agtttggtgg | 60 |

| gggtgctgac taaacttcaa gtcacagact tttatgtgac agattggagc agggtttgtt | 120 |
| atgcatgtag agaacccaaa ctaatttatt aaacaggata gaaacaggct gtctgggtga | 180 |
| aatggttctg agaaccatcc aattcacctg tcagatgctg atanactagc tcttcagatg | 240 |
| tttttctacc agttcagaga tnggttaatg actanttcca atggggaaaa agcaagatgg | 300 |
| attcacaaac caagtaattt taaacaaaga cactt | 335 |

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

| accaggttaa tattgccaca tatatccttt ccaattgcgg gctaaacaga cgtgtattta | 60 |
| gggttgttta aagacaaccc agcttaatat caagagaaat tgtgaccttt catggagtat | 120 |
| ctgatggaga aaacactgag ttttgacaaa tcttatttta ttcagatagc agtctgatca | 180 |
| cacatggtcc aacaacactc aaataataaa tcaaatatna tcagatgtta aagattggtc | 240 |
| ttcaaacatc atagccaatg atgccccgct tgcctataat ctctccgaca taaaaccaca | 300 |
| tcaacacctc agtggccacc aaaccattca gcacagcttc cttaactgtg agctgtttga | 360 |
| agctaccagt ctgagcacta ttgactatnt ttttcangct ctgaatagct ctaggatct | 420 |
| cagcangggt gggaggaacc agctcaacct tggcgtant | 459 |

<210> SEQ ID NO 143
<211> LENGTH: 140
<212> TYPE: DNA
<213> ORGANISM: Homo sapien

<400> SEQUENCE: 143

| acatttcctt ccaccaagtc aggactcctg gcttctgtgg gagttcttat cacctgaggg | 60 |
| aaatccaaac agtctctcct agaaaggaat agtgtcacca accccaccca tctccctgag | 120 |
| accatccgac ttccctgtgt | 140 |

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

| acttcagtaa caacatacaa taacaacatt aagtgtatat tgccatcttt gtcattttct | 60 |
| atctatacca ctctcccttc tgaaaacaan aatcactanc caatcactta tacaaatttg | 120 |
| aggcaattaa tccatatttg ttttcaataa ggaaaaaaag atgt | 164 |

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145

| acgtagacca | tccaactttg | tatttgtaat | ggcaaacatc | cagnagcaat | tcctaaacaa | 60 |
| actggagggt | atttataccc | aattatccca | ttcattaaca | tgccctcctc | ctcaggctat | 120 |
| gcaggacagc | tatcataagt | cggcccaggc | atccagatac | taccatttgt | ataaacttca | 180 |
| gtagggagt | ccatccaagt | gacaggtcta | atcaaaggag | gaaatggaac | ataagcccag | 240 |
| tagtaaaatn | ttgcttagct | gaaacagcca | caaaagactt | accgccgtgg | tgattaccat | 300 |
| caa | | | | | | 303 |

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

| actgcagctc | aattagaagt | ggtctctgac | tttcatcanc | ttctccctgg | gctccatgac | 60 |
| actggcctgg | agtgactcat | tgctctggtt | ggttgagaga | gctccttttgc | caacaggcct | 120 |
| ccaagtcagg | gctgggattt | gtttcctttc | cacattctag | caacaatatg | ctggccactt | 180 |
| cctgaacagg | gagggtggga | ggagccagca | tggaacaagc | tgccactttc | taaagtagcc | 240 |
| agacttgccc | ctgggcctgt | cacacctact | gatgaccttc | tgtgcctgca | ggatggaatg | 300 |
| tagggggtgag | ctgtgtgact | ctatggt | | | | 327 |

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

| acattgtttt | tttgagataa | agcattgana | gagctctcct | taacgtgaca | caatggaagg | 60 |
| actggaacac | atacccacat | ctttgttctg | agggataatt | ttctgataaa | gtcttgctgt | 120 |
| atattcaagc | acatatgtta | tatattattc | agttccatgt | ttatagccta | gtt | 173 |

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

| acaaccactt | tatctcatcg | aattttaac | ccaaactcac | tcactgtgcc | tttctatcct | 60 |
| atgggatata | ttatttgatg | ctccatttca | tcacacatat | atgaataata | cactcatact | 120 |
| gccctactac | ctgctgcaat | aatcacattc | ccttcctgtc | ctgaccctga | agccattggg | 180 |
| gtggtcctag | tggccatcag | tccangcctg | caccttgagc | ccttgagctc | cattgctcac | 240 |
| nccanccac | ctcaccgacc | ccatcctctt | acacagctac | ctccttgctc | tctaaccccca | 300 |

-continued

```
tagattatnt ccaaattcag tcaattaagt tactattaac actctacccg acatgtccag      360
caccactggt aagccttctc cagccaacac acacacacac acacncacac acacacatat      420
ccaggcacag gctacctcat cttcacaatc acccctttaa ttaccatgct atggtgg         477
```

<210> SEQ ID NO 149
<211> LENGTH: 207
<212> TYPE: DNA
<213> ORGANISM: Homo sapien

<400> SEQUENCE: 149

```
acagttgtat tataatatca agaaataaac ttgcaatgag agcatttaag agggaagaac       60
taacgtattt tagagagcca aggaaggttt ctgtggggag tgggatgtaa ggtgggcct      120 gatgataaat aagagtcagc caggtaagtg ggtggtgtgg tatgggcaca gtgaagaaca    180
tttcaggcag agggaacagc agtgaaa                                         207
```

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150

```
accttgattt cattgctgct ctgatggaaa cccaactatc taatttagct aaaacatggg       60
cacttaaatg tggtcagtgt ttggacttgt taactantgg catctttggg t              111
```

<210> SEQ ID NO 151
<211> LENGTH: 196
<212> TYPE: DNA
<213> ORGANISM: Homo sapien

<400> SEQUENCE: 151

```
agcgcggcag gtcatattga acattccaga tacctatcat tactcgatgc tgttgataac       60
agcaagatgg ctttgaactc agggtcacca ccagctattg gaccttacta tgaaaaccat    120
ggataccaac cggaaaaccc ctatcccgca cagcccactg tggtccccac tgtctacgag    180
gtgcatccgg ctcagt                                                     196
```

<210> SEQ ID NO 152
<211> LENGTH: 132
<212> TYPE: DNA
<213> ORGANISM: Homo sapien

<400> SEQUENCE: 152

```
acagcacttt cacatgtaag aagggagaaa ttcctaaatg taggagaaag ataacagaac       60 cttcccttt tcatctagtg gtggaaacct gatgctttat gttgacagga atagaaccag    120
gagggagttt gt                                                         132
```

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153 acaanacccca nganaggcca ctggccgtgg tgtcatggcc tccaaacatg aaagtgtcag       60
cttctgctct tatgtcctca tctgacaact ctttaccatt tttatcctcg ctcagcagga      120
gcacatcaat aaagtccaaa gtcttggact tggccttggc ttggaggaag tcatcaacac      180
cctggctagt gagggtgcgg cgccgctcct ggatgacggc atctgtgaag tcgtgcacca      240
gtctgcaggc cctgtggaag cgccgtccac acggagtnag gaatt                     285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg acccttctg tgaaaagcca tattatcacc       60
accccaaatt tttccttaaa tatctttaac tgaaggggtc agcctcttga ctgcaaagac     120
cctaagccgg ttacacagct aactcccact ggccctgatt tgtgaaattg ctgctgcctg     180
attggcacag gagtcgaagg tgttcagctc ccctcctccg tggaacgaga ctctgatttg     240
agtttcacaa attctcgggc cacctcgtca ttgctcctct gaaataaaat ccggagaatg     300
gtcaggcctg tctcatccat atggatcttc cgg                                  333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actggaaata ataaaaccca catcacagtg ttgtgtcaaa gatcatcagg gcatggatgg       60
gaaagtgctt tgggaactgt aaagtgccta acacatgatc gatgattttt gttataatat     120
ttgaatcacg gtgcatacaa actctcctgc ctgctcctcc tgggcccccag ccccagcccc    180 atcacagctc actgctctgt tcatccaggc ccagcatgta gtggctgatt cttcttggct    240
gcttttagcc tccanaagtt tctctgaagc caaccaaacc tctangtgta aggcatgctg    300
gccctggt                                                              308

<210> SEQ ID NO 156
<211> LENGTH: 295
<212> TYPE: DNA
<213> ORGANISM: Homo sapien

<400> SEQUENCE: 156
accttgctcg gtgcttggaa catattagga actcaaaata tgagatgata acagtgccta      60
ttattgatta ctgagagaac tgttagacat ttagttgaag attttctaca caggaactga    120
gaataggaga ttatgtttgg ccctcatatt ctctcctatc ctccttgcct cattctatgt    180
ctaatatatt ctcaatcaaa taaggttagc ataatcagga aatcgaccaa ataccaatat    240
aaaaccagat gtctatcctt aagattttca aatagaaaac aaattaacag actat         295

<210> SEQ ID NO 157
<211> LENGTH: 126
<212> TYPE: DNA
<213> ORGANISM: Homo sapien

<400> SEQUENCE: 157
acaagtttaa atagtgctgt cactgtgcat gtgctgaaat gtgaaatcca ccacatttct      60
gaagagcaaa acaaattctg tcatgtaatc tctatcttgg gtcgtgggta tatctgtccc    120
cttagt                                                                126

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158
acccactggt cttggaaaca cccatcctta atacgatgat ttttctgtcg tgtgaaaatg     60
aanccagcag gctgcccta gtcagtcctt ccttccagag aaaaagagat ttgagaaagt    120
gcctgggtaa ttcaccatta atttcctccc ccaaactctc tgagtcttcc cttaatattt    180
ctggtggttc tgaccaaagc aggtcatggt ttgttgagca tttgggatcc cagtgaagta    240
natgtttgta gccttgcata cttagcccct cccacgcaca aacggagtgg cagagtggtg    300
ccaaccctgt tttcccagtc cacgtagaca gattcacagt gcggaattct ggaagctgga    360
nacagacggg ctctttgcag agccgggact ctgagangga catgagggcc tctgcctctg    420
tgttcattct ctgatgtcct gt                                              442

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159
acttccaggt aacgttgttg tttccgttga gcctgaactg atgggtgacg ttgtaggttc     60
tccaacaaga actgaggttg cagagcgggt agggaagagt gctgttccag ttgcacctgg    120
gctgctgtgg actgttgttg attcctcact acggcccaag gttgtggaac tggcanaaag    180
gtgtgttgtt gganttgagc tcgggcggct gtggtaggtt gtgggctctt caacagggc    240 tgctgtggtg ccgggangtg aangtgttgt gtcacttgag cttggccagc tctggaaagt    300
antanattct tcctgaaggc cagcgcttgt ggagctggca ngggtcantg ttgtgtgtaa    360
cgaaccagtg ctgctgtggg tgggtgtana tcctccacaa agcctgaagt tatggtgtcn    420
tcaggtaana atgtggtttc agtgtccctg ggcngctgtg gaaggttgta nattgtcacc    480
aagggaataa gctgtggt                                                   498

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160
acctgcatcc agcttccctg ccaaactcac aaggagacat caacctctag acagggaaac     60

```
agcttcagga tacttccagg agacagagcc accagcagca aaacaaatat tcccatgcct      120
ggagcatggc atagaggaag ctganaaatg tggggtctga ggaagccatt tgagtctggc      180
cactagacat ctcatcagcc acttgtgtga agagatgccc catgacccca gatgcctctc      240
ccacccttac ctccatctca cacacttgag cttttccactc tgtataattc taacatcctg     300
gagaaaaatg gcagtttgac cgaacctgtt cacaacggta gaggctgatt tctaacgaaa      360
cttgtagaat gaagcctgga                                                  380

<210> SEQ ID NO 161
<211> LENGTH: 114
<212> TYPE: DNA
<213> ORGANISM: Homo sapien

<400> SEQUENCE: 161
actccacatc ccctctgagc aggcggttgt cgttcaaggt gtatttggcc ttgcctgtca       60
cactgtccac tggcccctta tccacttggt gcttaatccc tcgaaagagc atgt           114

<210> SEQ ID NO 162
<211> LENGTH: 177
<212> TYPE: DNA
<213> ORGANISM: Homo sapien

<400> SEQUENCE: 162
actttctgaa tcgaatcaaa tgatacttag tgtagtttta atatcctcat atatatcaaa       60
gttttactac tctgataatt ttgtaaacca ggtaaccaga acatccagtc atacagcttt      120
tggtgatata taacttggca ataacccagt ctggtgatac ataaaactac tcactgt        177

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163
catttataca gacaggcgtg aagacattca cgacaaaaac gcgaaattct atcccgtgac       60
canagaaggc agctacggct actcctacat cctggcgtgg gtggccttcg cctgcacctt      120
catcagcggc atgatgt                                                    137

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164
cttatcacaa tgaatgttct cctgggcagc gttgtgatct ttgccaccct cgtgacttta       60
tgcaatgcat catgctattt catacctaat gagggagttc caggagattc aaccaggaaa      120
tgcatggatc tcaaaggaaa caaacaccca ataaactcgg agtggcagac tgacaactgt      180
gagacatgca cttgctacga aacagaaatt tcatgttgca cccttgtttc tacacctgtg      240
ggttatgaca aagacaactg ccaaagaatc ttcaagaagg aggactgcaa gtatatcgtg      300
```

```
gtggagaaga aggacccaaa aaagacctgt tctgtcagtg aatggataat ctaatgtgct      360
tctagtaggc acagggctcc caggccaggc ctcattctcc tctggcctct aatagtcaat      420
gattgtgtag ccatgcctat cagtaaaaag atntttgagc aaacacttt                 469

<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165
acagtttttt atanatatcg acattgccgg cacttgtgtt cagtttcata aagctggtgg      60
atccgctgtc atccactatt ccttggctag agtaaaaatt attcttatag cccatgtccc     120
tgcaggccgc ccgcccgtag ttctcgttcc agtcgtcttg gcacacaggg tgccaggact     180
tcctctgaga tgagt                                                      195

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166
acatcttagt agtgtggcac atcaggggc catcagggtc acagtcactc atagcctcgc       60
cgaggtcgga gtccacacca ccggtgtagg tgtgctcaat cttgggcttg gcgcccacct    120
ttggagaagg gatatgctgc acacacatgt ccacaaagcc tgtgaactcg ccaaagaatt    180
tttgcagacc agcctgagca agggcggat gttcagcttc agctcctcct tcgtcaggtg    240
gatgccaacc tcgtctangg tccgtgggaa gctggtgtcc acntcaccta caacctgggc    300
gangatctta taaagaggct ccnagataaa ctccacgaaa cttctctggg agctgctagt    360
nggggccttt ttggtgaact ttc                                            383

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167
acagagccag accttggcca taaatgaanc agagattaag actaaacccc aagtcganat      60
tggagcagaa actggagcaa gaagtgggcc tggggctgaa gtagagacca aggccactgc    120
tatanccata cacagagcca actctcaggc caaggcnatg gttggggcag anccagagac    180
tcaatctgan tccaaagtgg tggctggaac actggtcatg acanaggcag tgactctgac    240 tgangtc                                                              247

<210> SEQ ID NO 168
<211> LENGTH: 273
<212> TYPE: DNA
<213> ORGANISM: Homo sapien
```

<220> FEATURE:
<221> NAME/KEY: misc_feature
<222> LOCATION: (1)...(273)
<223> OTHER INFORMATION: n = A,T,C or G

<400> SEQUENCE: 168

```
acttctaagt tttctagaag tggaaggatt gtantcatcc tgaaaatggg tttacttcaa      60
aatccctcan ccttgttctt cacnactgtc tatactgana gtgtcatgtt tccacaaagg     120
gctgacacct gagcctgnat tttcactcat ccctgagaag ccctttccag tagggtgggc     180
aattcccaac ttccttgcca caagcttccc aggctttctc ccctggaaaa ctccagcttg     240
agtcccagat acactcatgg gctgccctgg gca                                  273
```

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

```
acagccttgg cttccccaaa ctccacagtc tcagtgcaga aagatcatct tccagcagtc      60
agctcagacc agggtcaaag gatgtgacat caacagtttc tggtttcaga acaggttcta     120
ctactgtcaa atgaccccccc atacttcctc aaaggctgtg gtaagttttg cacaggtgag     180
ggcagcagaa aggggtant tactgatgga caccatcttc tctgtatact ccacactgac     240
cttgccatgg gcaaaggccc ctaccacaaa acaatagga tcactgctgg gcaccagctc     300
acgcacatca ctgacaaccg ggatggaaaa agaantgcca actttcatac atccaactgg     360
aaagtgatct gatactggat tcttaattac cttcaaaagc ttctggggggc catcagctgc     420
tcgaacactg a                                                          431
```

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

```
acctgtgggc tgggctgtta tgcctgtgcc ggctgctgaa agggagttca gaggtggagc      60
tcaaggagct ctgcaggcat tttgccaanc ctctccanag canagggagc aacctacact     120
ccccgctaga aagacaccag attggagtcc tgggagggg agttggggtg ggcatttgat     180
gtatacttgt cacctgaatg aangagccag agaggaanga gacgaanatg anattggcct     240
tcaaagctag gggtctggca ggtgga                                          266
```

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

-continued

```
ggcagccaaa tcataaacgg cgaggactgc agcccgcact cgcagccctg gcaggcggca      60
ctggtcatgg aaaacgaatt gttctgctcg ggcgtcctgg tgcatccgca gtgggtgctg     120
tcagccgcac actgtttcca gaagtgagtg cagagctcct acaccatcgg gctgggcctg     180
cacagtcttg aggccgacca agagccaggg agccagatgg tggaggccag cctctccgta     240
cggcacccag agtacaacag acccttgctc gctaacgacc tcatgctcat caagttggac     300
gaatccgtgt ccgagtctga caccatccgg agcatcagca ttgcttcgca gtgccctacc     360
gcggggaact cttgcctcgt ttctggctgg gtctgctgg cgaacggcag aatgcctacc      420
gtgctgcagt gcgtgaacgt gtcggtggtg tctgaggagg tctgcagtaa gctctatgac     480
ccgctgtacc accccagcat gttctgcgcc ggcggagggc aagaccagaa ggactcctgc     540
aacggtgact ctggggggcc cctgatctgc aacgggtact gcagggcct tgtgtctttc      600
ggaaaagccc cgtgtggcca agttggcgtg ccaggtgtct acaccaacct ctgcaaattc     660
actgagtgga tagagaaaac cgtccaggcc agttaactct ggggactggg aacccatgaa     720
attgaccccc aaatacatcc tgcggaagga attcaggaat atctgttccc agcccctcct     780
ccctcaggcc caggagtcca ggcccccagc ccctcctccc tcaaaccaag ggtacagatc     840
cccagcccct cctccctcag acccaggagt ccagaccccc cagccctcc tcccctcagac    900
ccaggagtcc agccctcct ccctcagacc caggagtcca gaccccag cccctcctcc       960
ctcagaccca gggtccagg ccccaaccc ctcctccctc agactcagag gtccaagccc      1020
ccaacccntc attccccaga cccagaggtc caggtcccag ccctcntcc ctcagaccca     1080
gcggtccaat gccacctaga ctntccctgt acacagtgcc cccttgtggc acgttgaccc    1140
aaccttacca gttggttttt catttttngt cccttttcccc tagatccaga aataaagttt   1200
aagagaagng caaaaaaaaa aaaaaaaaaa aaaaaaaaaa aaaaaaaa               1248
```

10> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

```
Met Val Glu Ala Ser Leu Ser Val Arg His Pro Glu Tyr Asn Arg Pro
 1               5                  10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
                100                 105                 110

Gly Gly Pro Leu Ile Cys Asn Gly Tyr Leu Gln Gly Leu Val Ser Phe
            115                 120                 125

Gly Lys Ala Pro Cys Gly Gln Val Gly Val Pro Gly Val Tyr Thr Asn
```

```
                130             135             140
Leu Cys Lys Phe Thr Glu Trp Ile Glu Lys Thr Val Gln Ala Ser
145             150             155
```

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173

| | | | | |
|---|---|---|---|---|
| ggcagcccgc | actcgcagcc | ctggcaggcg | gcactggtca | tggaaaacga | attgttctgc | 60 |
| tcgggcgtcc | tggtgcatcc | gcagtgggtg | ctgtcagccg | cacactgttt | ccagaactcc | 120 |
| tacaccatcg | ggctgggcct | gcacagtctt | gaggccgacc | aagagccagg | gagccagatg | 180 |
| gtggaggcca | gcctctccgt | acggcaccca | gagtacaaca | gacccttgct | cgctaacgac | 240 |
| ctcatgctca | tcaagttgga | cgaatccgtg | tccgagtctg | caccatccg | gagcatcagc | 300 |
| attgcttcgc | agtgccctac | cgcggggaac | tcttgcctcg | tttctggctg | ggtctgctg | 360 |
| gcgaacggtg | agctcacggg | tgtgtgtctg | ccctcttcaa | ggaggtcctc | tgcccagtcg | 420 |
| cgggggctga | cccagagctc | tgcgtcccag | gcagaatgcc | taccgtgctg | cagtgcgtga | 480 |
| acgtgtcggt | ggtgtctgag | gaggtctgca | gtaagctcta | tgaccgctg | taccaccca | 540 |
| gcatgttctg | cgccggcgga | gggcaagacc | agaaggactc | ctgcaacggt | gactctgggg | 600 |
| ggccctgat | ctgcaacggg | tacttgcagg | gccttgtgtc | tttcggaaaa | gccccgtgtg | 660 |
| gccaagttgg | cgtgccaggt | gtctacacca | acctctgcaa | attcactgag | tggatagaga | 720 |
| aaaccgtcca | ggccagttaa | ctctggggac | tgggaaccca | tgaaattgac | ccccaaatac | 780 |
| atcctgcgga | aggaattcag | gaatatctgt | tcccagcccc | tcctccctca | ggcccaggag | 840 |
| tccaggcccc | cagcccctcc | tccctcaaac | caagggtaca | gatccccagc | ccctcctccc | 900 |
| tcagacccag | gagtccagac | ccccagccc | ctcctccctc | agacccagga | gtccagcccc | 960 |
| tcctccntca | gacccaggag | tccagacccc | cagcccctc | ctccctcaga | cccaggggtt | 1020 |
| gaggccccca | acccctcctc | cttcagagtc | agaggtccaa | gcccccaacc | cctcgttccc | 1080 |
| cagacccaga | ggtnnaggtc | ccagccctc | ttccntcaga | cccagnggtc | caatgccacc | 1140 |
| tagattttcc | ctgnacacag | tgcccccttg | tggnangttg | acccaacctt | accagttggt | 1200 |
| ttttcatttt | tngtcccttt | ccctagatc | cagaaataaa | gtttaagaga | ngngcaaaaa | 1260 |
| aaaaa | | | | | | 1265 |

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

| | | | | |
|---|---|---|---|---|
| ggtcagccgc | acactgtttc | cagaagtgag | tgcagagctc | ctacaccatc | gggctgggcc | 60 |
| tgcacagtct | tgaggccgac | caagagccag | ggagccagat | ggtggaggcc | agcctctccg | 120 |
| tacggcaccc | agagtacaac | agacccttgc | tcgctaacga | cctcatgctc | atcaagttgg | 180 |

| | |
|---|---|
| acgaatccgt gtccgagtct gacaccatcc ggagcatcag cattgcttcg cagtgcccta | 240 |
| ccgcggggaa ctcttgcctc gtttctggct ggggtctgct ggcgaacggt gagctcacgg | 300 |
| gtgtgtgtct gccctcttca aggaggtcct ctgcccagtc gcggggctg acccagagct | 360 |
| ctgcgtccca ggcagaatgc ctaccgtgct gcagtgcgtg aacgtgtcgg tggtgtctga | 420 |
| ngaggtctgc antaagctct atgacccgct gtaccacccc ancatgttct gcgccggcgg | 480 |
| agggcaagac cagaaggact cctgcaacgt gagagagggg aaggggagg gcaggcgact | 540 |
| cagggaaggg tggagaaggg ggagacagag acacacaggg ccgcatggcg agatgcagag | 600 |
| atggagagac acagggag acagtgacaa ctagagagag aaactgagag aaacagagaa | 660 |
| ataaacacag gaataaagag aagcaaagga agagagaaac agaaacagac atggggaggc | 720 |
| agaaacacac acacatagaa atgcagttga ccttccaaca gcatggggcc tgagggcggt | 780 |
| gacctccacc caatagaaaa tcctcttata acttttgact ccccaaaaac ctgactagaa | 840 |
| atagcctact gttgacgggg agccttacca ataacataaa tagtcgattt atgcatacgt | 900 |
| tttatgcatt catgatatac ctttgttgga attttttgat atttctaagc tacacagttc | 960 |
| gtctgtgaat ttttttaaat tgttgcaact ctcctaaaat ttttctgatg tgtttattga | 1020 |
| aaaaatccaa gtataagtgg acttgtgcat tcaaaccagg gttgttcaag ggtcaactgt | 1080 |
| gtacccagag ggaaacagtg acacagattc atagaggtga aacacgaaga gaaacaggaa | 1140 |
| aaatcaagac tctacaaaga ggctgggcag ggtggctcat gcctgtaatc ccagcactt | 1200 |
| gggaggcgag gcaggcagat cacttgaggt aaggagttca agaccagcct ggccaaaatg | 1260 |
| gtgaaatcct gtctgtacta aaaatacaaa agttagctgg atatggtggc aggcgcctgt | 1320 |
| aatcccagct acttgggagg ctgaggcagg agaattgctt gaatatggga ggcagaggtt | 1380 |
| gaagtgagtt gagatcacac cactatactc cagctggggc aacagagtaa gactctgtct | 1440 |
| caaaaaaaa aaaaaaaa | 1459 |

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175

| | |
|---|---|
| gcgcagccct ggcaggcggc actggtcatg gaaaacgaat tgttctgctc gggcgtcctg | 60 |
| gtgcatccgc agtgggtgct gtcagccgca cactgtttcc agaactccta caccatcggg | 120 |
| ctgggcctgc acagtcttga ggccgaccaa gagccaggga gccagatggt ggaggccagc | 180 |
| ctctccgtac ggcacccaga gtacaacaga ctcttgctcg ctaacgacct catgctcatc | 240 |
| aagttggacg aatccgtgtc cgagtctgac accatccgga gcatcagcat tgcttcgcag | 300 |
| tgccctaccg cggggaactc ttgcctcgtn tctggctggg gtctgctggc gaacggcaga | 360 |
| atgcctaccg tgctgcactg cgtgaacgtg tcggtggtgt ctgaggangt ctgcagtaag | 420 |
| ctctatgacc cgctgtacca ccccagcatg ttctgcgccg gcgagggca agaccagaag | 480 |
| gactcctgca acggtgactc tgggggccc ctgatctgca acgggtactt gcagggcctt | 540 |
| gtgtctttcg gaaaagcccc gtgtggcaa cttggcgtgc caggtgtcta caccaacctc | 600 |
| tgcaaattca ctgagtggat agagaaaacc gtccagncca gttaactctg ggactgggaa | 660 |
| acccatgaaa ttgaccccca aatacatcct gcggaangaa ttcaggaata tctgttccca | 720 |

```
gcccctcctc cctcaggccc aggagtccag gcccccagcc cctcctccct caaaccaagg    780
gtacagatcc ccagcccctc ctccctcaga cccaggagtc cagaccccc  agccctctcnt   840 ccntcagacc caggagtcca gcccctcctc cntcagacgc aggagtccag accccccagc    900
ccntcntccg tcagacccag gggtgcaggc ccccaacccc tcntcctca  gagtcagagg    960 tccaagcccc caaccctcg ttccccagac ccagaggtnc aggtcccagc cctcctccc    1020 tcagacccag cggtccaatg ccacctagan tntccctgta cacagtgccc ccttgtggca   1080
ngttgaccca accttaccag ttggttttc attttttgtc cctttcccct agatccagaa   1140
ataaagtnta agagaagcgc aaaaaaa                                      1167
```

```
210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

Met Glu Asn Glu Leu Phe Cys Ser Gly Val Leu Val His Pro Gln Trp
  1               5                  10                  15

Val Leu Ser Ala Ala His Cys Phe Gln Asn Ser Tyr Thr Ile Gly Leu
             20                  25                  30

Gly Leu His Ser Leu Glu Ala Asp Gln Glu Pro Gly Ser Gln Met Val
         35                  40                  45

Glu Ala Ser Leu Ser Val Arg His Pro Glu Tyr Asn Arg Leu Leu Leu
     50                  55                  60

Ala Asn Asp Leu Met Leu Ile Lys Leu Asp Glu Ser Val Ser Glu Ser
 65                  70                  75                  80

Asp Thr Ile Arg Ser Ile Ser Ile Ala Ser Gln Cys Pro Thr Ala Gly
                 85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
    130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205
```

```
<210> SEQ ID NO 177
<211> LENGTH: 1119
<212> TYPE: DNA
<213> ORGANISM: Homo sapien

<400> SEQUENCE: 177
gcgcactcgc agccctggca ggcggcactg gtcatggaaa acgaattgtt ctgctcgggc    60
gtcctggtgc atccgcagtg ggtgctgtca gccgcacact gtttccagaa ctcctacacc   120
```

-continued

```
atcgggctgg gcctgcacag tcttgaggcc gaccaagagc cagggagcca gatggtggag        180
gccagcctct ccgtacggca cccagagtac aacagaccct tgctcgctaa cgacctcatg        240
ctcatcaagt tggacgaatc cgtgtccgag tctgacacca tccggagcat cagcattgct        300
tcgcagtgcc ctaccgcggg gaactcttgc ctcgtttctg gctgggtct gctggcgaac         360 gatgctgtga ttgccatcca gtcccagact gtgggaggct gggagtgtga aagctttcc         420 caaccctggc agggttgtac catttcggca acttccagtg caaggacgtc ctgctgcatc        480
ctcactgggt gctcactact gctcactgca tcacccggaa cactgtgatc aactagccag        540
caccatagtt ctccgaagtc agactatcat gattactgtg ttgactgtgc tgtctattgt        600
actaaccatg ccgatgttta ggtgaaatta gcgtcacttg gcctcaacca tcttggtatc        660
cagttatcct cactgaattg agatttcctg cttcagtgtc agccattccc acataatttc        720
tgacctacag aggtgaggga tcatatagct cttcaaggat gctggtactc ccctcacaaa        780
ttcatttctc ctgttgtagt gaaaggtgcg ccctctggag cctcccaggg tgggtgtgca        840
ggtcacaatg atgaatgtat gatcgtgttc ccattaccca aagccttta atccctcatg         900 ctcagtacac caggcaggt ctagcatttc ttcatttagt gtatgctgtc cattcatgca         960
accacctcag gactcctgga ttctctgcct agttgagctc ctgcatgctg cctccttggg       1020
gaggtgaggg agagggccca tggttcaatg ggatctgtgc agttgtaaca cattaggtgc       1080
ttaataaaca gaagctgtga tgttaaaaaa aaaaaaaa                               1119
```

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Thr Ala Ser
145                 150                 155                 160

Pro Gly Thr Leu
```

<210> SEQ ID NO 179
<211> LENGTH: 250
<212> TYPE: DNA
<213> ORGANISM: Homo sapien

<400> SEQUENCE: 179

| | | | | | |
|---|---|---|---|---|---|
| ctggagtgcc | ttggtgtttc | aagcccctgc | aggaagcaga | atgcaccttc | tgaggcacct | 60 |
| ccagctgccc | ccggccgggg | gatgcgaggc | tcggagcacc | cttgcccggc | tgtgattgct | 120 |
| gccaggcact | gttcatctca | gcttttctgt | ccctttgctc | ccggcaagcg | cttctgctga | 180 |
| aagttcatat | ctggagcctg | atgtcttaac | gaataaaggt | cccatgctcc | acccgaaaaa | 240 |
| aaaaaaaaaa | | | | | | 250 |

<210> SEQ ID NO 180
<211> LENGTH: 202
<212> TYPE: DNA
<213> ORGANISM: Homo sapien

<400> SEQUENCE: 180

| | | | | | |
|---|---|---|---|---|---|
| actagtccag | tgtggtggaa | ttccattgtg | ttgggcccaa | cacaatggct | acctttaaca | 60 |
| tcacccagac | cccgcccctg | cccgtgcccc | acgctgctgc | taacgacagt | atgatgctta | 120 |
| ctctgctact | cggaaactat | ttttatgtaa | ttaatgtatg | ctttcttgtt | tataaatgcc | 180 |
| tgatttaaaa | aaaaaaaaaa | aa | | | | 202 |

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181

| | | | | | |
|---|---|---|---|---|---|
| tccytttgkt | naggttttkkg | agacamccck | agacctwaan | ctgtgtcaca | gacttcyngg | 60 |
| aatgtttagg | cagtgctagt | aatttcytcg | taatgattct | gttattactt | tcctnattct | 120 |
| ttattcctct | ttcttctgaa | gattaatgaa | gttgaaaatt | gaggtggata | aatacaaaaa | 180 |
| ggtagtgtga | tagtataagt | atctaagtgc | agatgaaagt | gtgttatata | tatccattca | 240 |
| aaattatgca | agttagtaat | tactcagggt | taactaaatt | actttaatat | gctgttgaac | 300 |
| ctactctgtt | ccttggctag | aaaaaattat | aaacaggact | ttgttagttt | gggaagccaa | 360 |
| attgataata | ttctatgttc | taaaagttgg | gctatacata | aattattaag | aaatatggaw | 420 |
| ttttattccc | aggaatatgg | kgttcatttt | atgaatatta | cscrggatag | awgtwtgagt | 480 |
| aaaaycagtt | ttggtwaata | ygtwaatatg | tcmtaaataa | acaakgcttt | gacttatttc | 540 |
| caaaaaaaaa | aaaaaaaa | | | | | 558 |

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182

| | | | | | |
|---|---|---|---|---|---|
| acagggwttk | grggatgcta | agsccccrga | rwtygtttga | tccaaccctg | gcttwttttc | 60 |

| | |
|---|---|
| agaggggaaa atggggccta gaagttacag mscatytagy tggtgcgmtg gcacccctgg | 120 |
| cstcacacag astcccgagt agctgggact acaggcacac agtcactgaa gcaggccctg | 180 |
| ttwgcaattc acgttgccac ctccaactta aacattcttc atatgtgatg tccttagtca | 240 |
| ctaaggttaa actttcccac ccagaaaagg caacttagat aaaatcttag agtactttca | 300 |
| tactmttcta agtcctcttc cagcctcact kkgagtcctm cytgggggtt gataggaant | 360 |
| ntctcttggc tttctcaata aartctctat ycatctcatg tttaatttgg tacgcatara | 420 |
| awtgstgara aaattaaaat gttctggtty mactttaaaa araaaaaaaa aaaaaaaa | 479 |

<210> SEQ ID NO 183
<211> LENGTH: 384
<212> TYPE: DNA
<213> ORGANISM: Homo sapien

<400> SEQUENCE: 183

| | |
|---|---|
| aggcgggagc agaagctaaa gccaaagccc aagaagagtg gcagtgccag cactggtgcc | 60 |
| agtaccagta ccaataacag tgccagtgcc agtgccagca ccagtggtgg cttcagtgct | 120 |
| ggtgccagcc tgaccgccac tctcacattt gggctcttcg ctggccttgg tggagctggt | 180 |
| gccagcacca gtggcagctc tggtgcctgt ggtttctcct acaagtgaga ttttagatat | 240 |
| tgttaatcct gccagtcttt ctcttcaagc cagggtgcat cctcagaaac ctactcaaca | 300 |
| cagcactcta ggcagccact atcaatcaat tgaagttgac actctgcatt aratctattt | 360 |
| gccatttcaa aaaaaaaaaa aaaa | 384 |

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

| | |
|---|---|
| accgaattgg gaccgctggc ttataagcga tcatgtyynt ccrgtatkac ctcaacgagc | 60 |
| agggagatcg agtctatacg ctgaagaaat ttgacccgat gggacaacag acctgctcag | 120 |
| cccatcctgc tcggttctcc ccagatgaca aatactctsg acaccgaatc accatcaaga | 180 |
| aacgcttcaa ggtgctcatg acccagcaac cgcgccctgt cctctgaggg tcccttaaac | 240 |
| tgatgtcttt tctgccacct gttacccctc ggagactccg taaccaaact cttcggactg | 300 |
| tgagccctga tgccttttg ccagccatac tctttggcat ccagtctctc gtggcgattg | 360 |
| attatgcttg tgtgaggcaa tcatggtggc atcacccata aagggaacac atttgacttt | 420 |
| tttttctcat atttaaatt actacmagaw tattwmagaw waaatgawtt gaaaaactst | 480 |
| taaaaaaaaa aaaaaa | 496 |

<210> SEQ ID NO 185
<211> LENGTH: 384
<212> TYPE: DNA
<213> ORGANISM: Homo sapien

<400> SEQUENCE: 185

| | |
|---|---|
| gctggtagcc tatggcgkgg cccacggagg ggctcctgag gccacggrac agtgacttcc | 60 |
| caagtatcyt gcgcsgcgtc ttctaccgtc cctacctgca gatcttcggg cagattcccc | 120 |
| aggaggacat ggacgtggcc ctcatggagc acagcaactg ytcgtcggag cccggcttct | 180 |

```
gggcacaccc tcctggggcc caggcgggca cctgcgtctc ccagtatgcc aactggctgg      240
tggtgctgct cctcgtcatc ttcctgctcg tggccaacat cctgctggtc aacttgctca      300
ttgccatgtt cagttacaca ttcggcaaag tacagggcaa cagcgatctc tactgggaag      360
gcgcagcgtt accgcctcat ccgg                                              384
```

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

```
gagttagctc ctccacaacc ttgatgaggt cgtctgcagt ggcctctcgc ttcataccgc       60
tnccatcgtc atactgtagg tttgccacca cytcctggca tcttggggcg gcntaatatt      120
ccaggaaact ctcaatcaag tcaccgtcga tgaaacctgt gggctggttc tgtcttccgc      180
tcggtgtgaa aggatctccc agaaggagtg ctcgatcttc cccacacttt tgatgacttt      240
attgagtcga ttctgcatgt ccagcaggag gttgtaccag ctctctgaca gtgaggtcac      300
cagccctatc atgccgttga mcgtgccgaa garcaccgag ccttgtgtgg gggkkgaagt      360
ctcacccaga ttctgcatta ccagagagcc gtggcaaaag acattgacaa actcgcccag      420
gtggaaaaag amcamctcct ggargtgctn gccgctcctc gtcmgttggt ggcagcgctw      480
tccttttgac acacaaacaa gttaaaggca ttttcagccc ccagaaantt gtcatcatcc      540
aagatntcgc acagcactna tccagttggg attaaat                               577
```

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

```
aacatcttcc tgtataatgc tgtgtaatat cgatccgatn ttgtctgstg agaatycatw       60
actkggaaaa gmaacattaa agcctggaca ctggtattaa aattcacaat atgcaacact      120
ttaaacagtg tgtcaatctg ctcccyynac tttgtcatca ccagtctggg aakaagggta      180
tgccctattc acacctgtta aaagggcgct aagcattttt gattcaacat cttttttttt      240
gacacaagtc cgaaaaaagc aaaagtaaac agttatyaat ttgttagcca attcactttc      300
ttcatgggac agagccatyt gatttaaaaa gcaaattgca taatattgag cttygggagc      360
tgatatttga gcggaagagt agcctttcta cttcaccaga cacaactccc tttcatattg      420
ggatgttnac naaagtwatg tctctwacag atgggatgct tttgtggcaa ttctgttctg      480
aggatctccc agtttattta ccacttgcac aagaaggcgt tttcttcctc aggc            534
```

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)

<223> OTHER INFORMATION: n = A,T,C or G

<400> SEQUENCE: 188

| | | | | | |
|---|---|---|---|---|---|
| agaaaccagt | atctctnaaa | acaacctctc | ataccttgtg | gacctaattt | tgtgtgcgtg | 60 |
| tgtgtgtgcg | cgcatattat | atagacaggc | acatctttt | tactttgta | aaagcttatg | 120 |
| cctctttggt | atctatatct | gtgaaagttt | taatgatctg | ccataatgtc | ttggggacct | 180 |
| ttgtcttctg | tgtaaatggt | actagagaaa | acacctatnt | tatgagtcaa | tctagttngt | 240 |
| tttattcgac | atgaaggaaa | tttccagatn | acaacactna | caaactctcc | ctkgackarg | 300 |
| ggggacaaag | aaaagcaaaa | ctgamcataa | raaacaatwa | cctggtgaga | arttgcataa | 360 |
| acagaaatwr | ggtagtatat | tgaarnacag | catcattaaa | rmgttwtktt | wttctccctt | 420 |
| gcaaaaaaca | tgtacngact | tcccgttgag | taatgccaag | ttgtttttt | tatnataaaa | 480 |
| cttgcccttc | attacatgtt | tnaaagtggt | gtggtgggcc | aaaatattga | aatgatggaa | 540 |
| ctgactgata | aagctgtaca | ataagcagt | gtgcctaaca | agcaacacag | taatgttgac | 600 |
| atgcttaatt | cacaaatgct | aatttcatta | taaatgtttg | ctaaaataca | cttttgaacta | 660 |
| tttttctgtn | ttcccagagc | tgagatntta | gatttatgt | agtataagt | gaaaantac | 720 |
| gaaaataata | acattgaaga | aaananaaa | aaanaaaaaa | a | | 761 |

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

| | | | | | |
|---|---|---|---|---|---|
| tttttttt | tttgccgatn | ctactatttt | attgcaggan | gtgggggtgt | atgcaccgca | 60 |
| caccggggct | atnagaagca | agaaggaagg | agggagggca | cagcccttg | ctgagcaaca | 120 |
| aagccgcctg | ctgccttctc | tgtctgtctc | ctggtgcagg | cacatgggga | gaccttcccc | 180 |
| aaggcagggg | ccaccagtcc | aggggtggga | atacaggggg | tgggangtgt | gcataagaag | 240 |
| tgataggcac | aggccacccg | gtacagaccc | ctcggctcct | gacaggtnga | tttcgaccag | 300 |
| gtcattgtgc | cctgcccagg | cacagcgtan | atctggaaaa | gacagaatgc | tttcctttc | 360 |
| aaatttggct | ngtcatngaa | ngggcanttt | tccaanttng | gctnggtctt | ggtacncttg | 420 |
| gttcggccca | gctccncgtc | caaaaantat | tcaccnnct | ccnaattgct | tgcnggnccc | 480 |
| cc | | | | | | 482 |

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190

| | | | | | |
|---|---|---|---|---|---|
| tttttttt | ttttaaaaca | gttttcaca | acaaaattta | ttagaagaat | agtggttttg | 60 |
| aaaactctcg | catccagtga | gaactaccat | acaccacatt | acagctngga | atgtnctcca | 120 |
| aatgtctggt | caaatgatac | aatggaacca | ttcaatctta | cacatgcacg | aaagaacaag | 180 |
| cgcttttgac | atacaatgca | caaaaaaaaa | agggggggg | gaccacatgg | attaaaattt | 240 |

```
taagtactca tcacatacat taagacacag ttctagtcca gtcnaaaatc agaactgcnt    300
tgaaaaattt catgtatgca atccaaccaa agaacttnat tggtgatcat gantnctcta    360
ctacatcnac cttgatcatt gccaggaacn aaaagttnaa ancacncngt acaaaaanaa    420
tctgtaattn anttcaacct ccgtacngaa aaatnttnnt tatacactcc c             471
```

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

```
gagggattga aggtctgttc tastgtcggm ctgttcagcc accaactcta acaagttgct     60
gtcttccact cactgtctgt aagctttttta acccagacwg tatcttcata aatagaacaa    120
attcttcacc agtcacatct tctaggacct ttttggattc agttagtata agctcttcca    180
cttcctttgt taagacttca tctggtaaag tcttaagttt tgtagaaagg aattyaattg    240
ctcgttctct aacaatgtcc tctccttgaa gtatttggct gaacaaccca cctaaagtcc    300 cttttgtgcat ccattttaaa tatacttaat agggcattgk tncactaggt taaattctgc   360
aagagtcatc tgtctgcaaa agttgcgtta gtatatctgc ca                       402
```

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

```
gagctcggat ccaataatct tgtctgagg gcagcacaca tatncagtgc catggnaact      60
ggtctacccc acatgggagc agcatgccgt agntatataa ggtcattccc tgagtcagac    120
atgcytyttt gaytaccgtg tgccaagtgc tggtgattct yaacacacyt ccatcccgyt    180
cttttgtgga aaaactggca cttktctgga actagcarga catcacttac aaattcaccc    240
acgagacact tgaaaggtgt aacaaagcga ytcttgcatt gcttttttgtc cctccggcac   300 cagttgtcaa tactaacccg ctggtttgcc tccatcacat ttgtgatctg tagctctgga   360
tacatctcct gacagtactg aagaacttct tcttttgttt caaaagcarc tcttggtgcc    420
tgttggatca ggttcccatt tcccagtcyg aatgttcaca tggcatattt wacttcccac    480
aaaacattgc gatttgaggc tcagcaacag caaatcctgt tccggcattg gctgcaagag    540
cctcgatgta gccggccagc gccaaggcag gcgccgtgag ccccaccagc agcagaagca    600
g                                                                    601
```

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

| | | | | | |
|---|---|---|---|---|---|
| atacagccca | natcccacca | cgaagatgcg | cttgttgact | gagaacctga | tgcggtcact | 60 |
| ggtcccgctg | tagccccagc | gactctccac | ctgctggaag | cggttgatgc | tgcactcytt | 120 |
| cccaacgcag | gcagmagcgg | gsccggtcaa | tgaactccay | tcgtggcttg | gggtkgacgg | 180 |
| tkaagtgcag | gaagaggctg | accacctcgc | ggtccaccag | gatgcccgac | tgtgcgggac | 240 |
| ctgcagcgaa | actcctcgat | ggtcatgagc | gggaagcgaa | tgaggcccag | ggccttgccc | 300 |
| agaaccttcc | gcctgttctc | tggcgtcacc | tgcagctgct | gccgctgaca | ctcggcctcg | 360 |
| gaccagcgga | caaacggcrt | tgaacagccg | cacctcacgg | atgcccagtg | tgtcgcgctc | 420 |
| caggammgsc | accagcgtgt | ccaggtcaat | gtcggtgaag | ccctccgcgg | gtratggcgt | 480 |
| ctgcagtgtt | tttgtcgatg | ttctccaggc | acaggctggc | cagctgcggt | tcatcgaaga | 540 |
| gtcgcgcctg | cgtgagcagc | atgaaggcgt | tgtcggctcg | cagttcttct | tcaggaactc | 600 |
| cacgcaat | | | | | | 608 |

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194

| | | | | | |
|---|---|---|---|---|---|
| gaacggctgg | accttgcctc | gcattgtgct | tgctggcagg | gaataccttg | gcaagcagyt | 60 |
| ccagtccgag | cagccccaga | ccgctgccgc | ccgaagctaa | gcctgcctct | ggccttcccc | 120 |
| tccgcctcaa | tgcagaacca | gtagtgggag | cactgtgttt | agagttaaga | gtgaacactg | 180 |
| tttgatttta | cttgggaatt | tcctctgtta | tatagctttt | cccaatgcta | atttccaaac | 240 |
| aacaacaaca | aaataacatg | tttgcctgtt | aagttgtata | aaagtaggtg | attctgtatt | 300 |
| taaagaaaat | attactgtta | catatactgc | ttgcaatttc | tgtatttatt | gktnctstgg | 360 |
| aaataaatat | agttattaaa | ggttgtcant | cc | | | 392 |

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195

| | | | | | |
|---|---|---|---|---|---|
| ccsttkgagg | ggtkaggkyc | cagttyccga | gtggaagaaa | caggccagga | gaagtgcgtg | 60 |
| ccgagctgag | gcagatgttc | ccacagtgac | ccccagagcc | stgggstata | gtytctgacc | 120 |
| cctcncaagg | aaagaccacs | ttctggggac | atgggctgga | gggcaggacc | tagaggcacc | 180 |
| aagggaaggc | cccattccgg | ggstgttccc | cgaggaggaa | gggaagggggc | tctgtgtgcc | 240 |
| ccccasgagg | aagaggccct | gagtcctggg | atcagacacc | ccttcacgtg | tatccccaca | 300 |
| caaatgcaag | ctcaccaagg | tccctctca | gtccccttcc | stacaccctg | amcggccact | 360 |
| gscscacacc | cacccagagc | acgccacccg | ccatggggar | tgtgctcaag | gartcgcngg | 420 |
| gcarcgtgga | catctngtcc | cagaaggggg | cagaatctcc | aatagangga | ctgarcmstt | 480 |
| gctnanaaaa | aaaaanaaaa | aa | | | | 502 |

<210> SEQ ID NO 196
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196

```
ggttacttgg tttcattgcc accacttagt ggatgtcatt tagaaccatt ttgtctgctc     60
cctctggaag ccttgcgcag agcggacttt gtaattgttg gagaataact gctgaatttt    120
wagctgtttk gagttgatts gcaccactgc acccacaact tcaatatgaa aacyawttga    180
actwatttat tatcttgtga aaagtataac aatgaaaatt ttgttcatac tgtattkatc    240
aagtatgatg aaaagcaawa gatatatatt cttttattat gttaaattat gattgccatt    300
attaatcggc aaaatgtgga gtgtatgttc ttttcacagt aatatatgcc ttttgtaact    360
tcacttggtt attttattgt aaatgartta caaaattctt aatttaagar aatggtatgt    420
watatttatt tcattaattt ctttcctkgt ttacgtwaat tttgaaaaga wtgcatgatt    480
tcttgacaga aatcgatctt gatgctgtgg aagtagtttg acccacatcc ctatgagttt    540
ttcttagaat gtataaaggt tgtagcccat cnaacttcaa agaaaaaaat gaccacatac    600
tttgcaatca ggctgaaatg tggcatgctn ttctaattcc aactttataa actagcaaan    660
aagtg                                                                665
```

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197

```
ttttntttt ttttttttgc aggaaggatt ccatttattg tggatgcatt ttcacaatat     60
atgtttattg gagcgatcca ttatcagtga aaagtatcaa gtgtttataa nattttagg    120
aaggcagatt cacagaacat gctngtcngc ttgcagtttt acctcgtana gatnacagag    180
aattatagtc naaccagtaa acnaggaatt tacttttcaa aagattaaat ccaaactgaa    240
caaaattcta ccctgaaact tactccatcc aaatattgga ataanagtca gcagtgatac    300
attctcttct gaactttaga ttttctagaa aaatatgtaa tagtgatcag gaagagctct    360
tgttcaaaag tacaacnaag caatgttccc ttaccatagg ccttaattca aactttgatc    420
catttcactc ccatcacggg agtcaatgct acctgggaca cttgtatttt gttcatnctg    480
ancntggctt aa                                                        492
```

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198

| | |
|---|---|
| tttnttttgn atttcantct gtannaanta ttttcattat gtttattana aaaatatnaa | 60 |
| tgtntccacn acaaatcatn ttacntnagt aagaggccan ctacattgta caacatacac | 120 |
| tgagtatatt ttgaaaagga caagtttaaa gtanacncat attgccganc atancacatt | 180 |
| tatacatggc ttgattgata tttagcacag canaaactga gtgagttacc agaaanaaat | 240 |
| natatatgtc aatcngattt aagatacaaa acagatccta tggtacatan catcntgtag | 300 |
| gagttgtggc tttatgttta ctgaaagtca atgcagttcc tgtacaaaga gatggccgta | 360 |
| agcattctag tacctctact ccatggttaa gaatcgtaca cttatgttta catatgtnca | 420 |
| gggtaagaat tgtgttaagt naanttatgg agaggtccan gagaaaaatt tgatncaa | 478 |

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

| | |
|---|---|
| agtgacttgt cctccaacaa aaccccttga tcaagtttgt ggcactgaca atcagaccta | 60 |
| tgctagttcc tgtcatctat tcgctactaa atgcagactg gaggggacca aaaaggggca | 120 |
| tcaactccag ctggattatt ttggagcctg caaatctatt cctacttgta cggactttga | 180 |
| agtgattcag tttcctctac ggatgagaga ctggctcaag aatatcctca tgcagcttta | 240 |
| tgaagccnac tctgaacacg ctggttatct nagatgagaa ncagaaaat aaagtcnaga | 300 |
| aaatttacct ggangaaaag aggctttngg ctggggacca tcccattgaa ccttctctta | 360 |
| anggactta agaanaaact accacatgtn tgtngtatcc tggtgccngg ccgttttantg | 420 |
| aacntngacn ncacccttnt ggaatanant cttgacngcn tcctgaactt gctcctctgc | 480 |
| ga | 482 |

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

| | |
|---|---|
| cggccgcaag tgcaactcca gctgggggccg tgcggacgaa gattctgcca gcagttggtc | 60 |
| cgactgcgac gacggcggcg cgacagtcg caggtgcagc gcgggcgcct ggggtcttgc | 120 |
| aaggctgagc tgacgccgca gaggtcgtgt cacgtcccac gaccttgacg ccgtcgggga | 180 |
| cagccggaac agagcccggt gaangcggga ggcctcgggg agccctcgg gaagggcggc | 240 |
| ccgagagata cgcaggtgca ggtggccgcc | 270 |

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

| | |
|---|---:|
| tttttttttt ttttggaatc tactgcgagc acagcaggtc agcaacaagt ttattttgca | 60 |
| gctagcaagg taacagggta gggcatggtt acatgttcag gtcaacttcc tttgtcgtgg | 120 |
| ttgattggtt tgtctttatg ggggcggggt ggggtagggg aaancgaagc anaantaaca | 180 |
| tggagtgggt gcaccctccc tgtagaacct ggttacnaaa gcttggggca gttcacctgg | 240 |
| tctgtgaccg tcattttctt gacatcaatg ttattagaag tcaggatatc ttttagagag | 300 |
| tccactgtnt ctggagggag attagggttt cttgccaana tccaancaaa atccacntga | 360 |
| aaaagttgga tgatncangt acngaatacc ganggcatan ttctcatant cggtggcca | 419 |

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

| | |
|---|---:|
| tttnttttt ttttttttt ttttttttt ttttttttt ttttttttt ttttttttt | 60 |
| tggcacttaa tccattttta tttcaaaatg tctacaaant ttnaatncnc cattatacng | 120 |
| gtnattttnc aaaatctaaa nnttattcaa atntnagcca aantccttac ncaaatnnaa | 180 |
| tacncncaaa aatcaaaaat atacntntct ttcagcaaac ttngttacat aaattaaaaa | 240 |
| aatatatacg gctggtgttt tcaaagtaca attatcttaa cactgcaaac atntttnnaa | 300 |
| ggaactaaaa taaaaaaaaa cactnccgca aaggttaaag ggaacaacaa attcnttta | 360 |
| caacancnnc nattataaaa atcatatctc aaatcttagg ggaatatata cttcacacng | 420 |
| ggatcttaac ttttactnca ctttgtttat ttttttanaa ccattgtntt gggcccaaca | 480 |
| caatggnaat nccnccncnc tggactagt | 509 |

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

| | |
|---|---:|
| ttttttttt ttttttttga cccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa attttgact cttgtaaaac atccaaattc | 240 |
| attttcttg tctttaaaat tatctaatct ttccattttt tccctattcc aagtcaattt | 300 |
| gcttctctag cctcatttcc tagctcttat ctactattag taagtggctt ttttcctaaa | 360 |
| agggaaaaca ggaagagana atggcacaca aaacaaacat tttatattca tatttctacc | 420 |
| tacgttaata aaatagcatt ttgtgaagcc agctcaaaaa aaggcttaga tcctttatg | 480 |
| tccatttag tcactaaacg atatcnaaag tgccagaatg caaaaggttt gtgaacattt | 540 |
| attcaaaagc taatataaga tatttcacat actcatcttt ctg | 583 |

<210> SEQ ID NO 204

<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204

```
tttttttttnt tttttttttt tttttttnctc ttctttttttt ttganaatga ggatcgagtt    60
tttcactctc tagatagggc atgaagaaaa ctcatctttc cagctttaaa ataacaatca     120
aatctcttat gctatatcat attttaagtt aaactaatga gtcactggct tatcttctcc     180
tgaaggaaat ctgttcattc ttctcattca tatagttata tcaagtacta ccttgcatat     240
tgagaggttt ttcttctcta tttacacata tatttccatg tgaatttgta tcaaacettt     300
attttcatgc aaactagaaa ataatgtntt cttttgcata agagaagaga acaatatnag     360
cattacaaaa ctgctcaaat tgtttgttaa gnttatccat tataattagt tnggcaggag     420
ctaatacaaa tcacatttac ngacnagcaa taataaaact gaagtaccag ttaaatatcc     480
aaataatta aaggaacatt tttagcctgg gtataattag ctaattcact ttacaagcat     540
ttattnagaa tgaattcaca tgttattatt ccntagccca acacaatgg                 589
```

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205

```
tttttntttt tttttttcagt aataatcaga acaatattta ttttatatt taaaattcat     60
agaaaagtgc cttacatttta ataaagtttt gtttctcaaa gtgatcagag gaattagata   120
tngtcttgaa caccaatatt aatttgagga aaatacacca aaatacatta agtaaattat   180
ttaagatcat agagcttgta agtgaaaaga taaaatttga cctcagaaac tctgagcatt   240
aaaaatccac tattagcaaa taaattacta tggacttctt gctttaattt tgtgatgaat   300
atggggtgtc actggtaaac caacacattc tgaaggatac attacttagt gatagattct   360
tatgtacttt gctanatnac gtggatatga gttgacaagt ttctctttct tcaatctttt   420
aaggggcnga ngaaatgagg aagaaaagaa aaggattacg catactgttc tttctatngg   480
aaggattaga tatgttttcct ttgccaatat taaaaaaata ataatgttta ctactagtga   540
aaccc                                                                545
```

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206

```
tttttttttt ttttttagtc aagtttctna tttttattat aattaaagtc ttggtcattt     60
catttattag ctctgcaact tacatatta aattaaagaa acgttnttag acaactgtna   120
caatttataa atgtaaggtg ccattattga gtanatatat tcctccaaga gtggatgtgt   180
```

```
cccttctccc accaactaat gaancagcaa cattagttta attttattag tagatnatac      240
actgctgcaa acgctaattc tcttctccat ccccatgtng atattgtgta tatgtgtgag      300
ttggtnagaa tgcatcanca atctnacaat caacagcaag atgaagctag gcntgggctt      360
tcggtgaaaa tagactgtgt ctgtctgaat caaatgatct gacctatcct cggtggcaag      420
aactcttcga accgcttcct caaaggcngc tgccacattt gtggcntctn ttgcacttgt      480
ttcaaaa                                                                487

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207
tgaattggct aaaagactgc attttttanaa ctagcaactc ttatttcttt cctttaaaaa     60
acatagcat taaatcccaa atcctattta aagacctgac agcttgagaa ggtcactact      120
catttatag gaccttctgg tggttctgct gttacnttgg aantctgaca atccttgana      180
atctttgcat gcagaggagg taaaaggtat tggattttca cagaggaana acacagcgca     240
gaaatgaagg ggccaggctt actgagcttg tccactggag ggctcatggg tgggacatgg     300
aaaagaaggc agcctaggcc ctggggagcc ca                                   332

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208
agggcgtggt gcggagggcg ttactgtttt gtctcagtaa caataaatac aaaaagactg      60
gttgtgttcc ggccccatcc aaccacgaag ttgatttctc ttgtgtgcag agtgactgat     120
tttaaaggac atggagcttg tcacaatgtc acaatgtcac agtgtgaagg gcacactcac     180
tcccgcgtga ttcacattta gcaaccaaca atagctcatg agtccatact tgtaaatact     240
tttggcagaa tacttnttga aacttgcaga tgataactaa gatccaagat atttcccaaa     300
gtaaatagaa gtgggtcata atattaatta cctgttcaca tcagcttcca tttacaagtc     360
atgagcccag acactgacat caaactaagc ccacttagac tcctcaccac cagtctgtcc     420
tgtcatcaga caggaggctg tcaccttgac caaattctca ccagtcaatc atctatccaa     480
aaaccattac ctgatccact tccggtaatg caccaccttg gtga                      524

<210> SEQ ID NO 209
<211> LENGTH: 159
<212> TYPE: DNA
<213> ORGANISM: Homo sapien

<400> SEQUENCE: 209
gggtgaggaa atccagagtt gccatggaga aaattccagt gtcagcattc ttgctccttg      60
tggccctctc ctacactctg gccagagata ccacagtcaa acctggagcc aaaaaggaca     120
caaaggactc tcgacccaaa ctgccccaga ccctctcca                            159

<210> SEQ ID NO 210
<211> LENGTH: 256
```

<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210

| | | | | | |
|---|---|---|---|---|---|
| actccctggc | agacaaaggc | agaggagaga | gctctgttag | ttctgtgttg | ttgaactgcc | 60 |
| actgaatttc | tttccacttg | gactattaca | tgccanttga | gggactaatg | gaaaaacgta | 120 |
| tggggagatt | ttanccaatt | tangtntgta | aatgggagaa | ctggggcagg | cgggagagat | 180 |
| ttgcagggtg | naaatgggan | ggctggtttg | ttanatgaac | agggacatag | gaggtaggca | 240 |
| ccaggatgct | aaatca | | | | | 256 |

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

| | | | | | |
|---|---|---|---|---|---|
| acattgtttt | tttgagataa | agcattgaga | gagctctcct | taacgtgaca | caatggaagg | 60 |
| actggaacac | atacccacat | ctttgttctg | agggataatt | ttctgataaa | gtcttgctgt | 120 |
| atattcaagc | acatatgtta | tatattattc | agttccatgt | ttatagccta | gttaaggaga | 180 |
| ggggagatac | attcngaaag | aggactgaaa | gaaatactca | agtnggaaaa | cagaaaaaga | 240 |
| aaaaaggag | caaatgagaa | gcct | | | | 264 |

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

| | | | | | |
|---|---|---|---|---|---|
| acccaaaaat | ccaatgctga | atatttggct | tcattattcc | canattcttt | gattgtcaaa | 60 |
| ggatttaatg | ttgtctcagc | ttgggcactt | cagttaggac | ctaaggatgc | cagccggcag | 120 |
| gtttatatat | gcagcaacaa | tattcaagcg | cgacaacagg | ttattgaact | tgcccgccag | 180 |
| ttnaatttca | ttcccattga | cttgggatcc | ttatcatcag | ccagagagat | tgaaaattta | 240 |
| cccctacnac | tctttactct | ctgganaggg | ccagtggtgg | tagctataag | cttggccaca | 300 |
| ttttttttc | ctttattcct | ttgtcaga | | | | 328 |

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

| | | | | | |
|---|---|---|---|---|---|
| acttatgagc | agagcgacat | atccnagtgt | agactgaata | aaactgaatt | ctctccagtt | 60 |

-continued

| | |
|---|---|
| taaagcattg ctcactgaag ggatagaagt gactgccagg agggaaagta agccaaggct | 120 |
| cattatgcca aagganatat acatttcaat tctccaaact tcttcctcat tccaagagtt | 180 |
| ttcaatattt gcatgaacct gctgataanc catgttaana aacaaatatc tctctnacct | 240 |
| tctcatcggt | 250 |

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

| | |
|---|---|
| acccagaatc caatgctgaa tatttggctt cattattccc agattctttg attgtcaaag | 60 |
| gatttaatgt tgtctcagct tgggcacttc agttaggacc taaggatgcc agccggcagg | 120 |
| tttatatatg cagcaacaat attcaagcgc gacaacaggt tattgaactt gcccgccagt | 180 |
| tgaatttcat tcccattgac ttgggatcct tatcatcagc canagagatt gaaaatttac | 240 |
| ccctacgact ctttactctc tggagagggc cagtggtggt agctataagc ttggccacat | 300 |
| ttttttttcc tttattcctt tgtcagagat gcgattcatc catatgctan aaaccaacag | 360 |
| agtgactttt acaaaattcc tataganatt gtgaataaaa ccttacctat agttgccatt | 420 |
| actttgctct ccctaatata cctc | 444 |

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

| | |
|---|---|
| acttatgagc agagcgacat atccaagtgt anactgaata aaactgaatt ctctccagtt | 60 |
| taaagcattg ctcactgaag ggatagaagt gactgccagg agggaaagta agccaaggct | 120 |
| cattatgcca aagganatat acatttcaat tctccaaact tcttcctcat tccaagagtt | 180 |
| ttcaatattt gcatgaacct gctgataagc catgttgaga aacaaatatc tctctgacct | 240 |
| tctcatcggt aagcagaggc tgtaggcaac atggaccata gcgaanaaaa aacttagtaa | 300 |
| tccaagctgt tttctacact gtaaccaggt ttccaaccaa ggtggaaatc tcctatactt | 360 |
| ggtgcc | 366 |

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216

| | |
|---|---|
| ctgtataaac agaactccac tgcangaggg agggccgggc caggagaatc tccgcttgtc | 60 |
| caagacaggg gcctaaggag ggtctccaca ctgctnntaa gggctnttnc atttttttat | 120 |
| taataaaaag tnnaaaggc ctcttctcaa cttttttccc ttnggctgga aaatttaaaa | 180 |

```
atcaaaaatt tcctnaagtt ntcaagctat catatatact ntatcctgaa aaagcaacat      240
aattcttcct tccctccttt                                                  260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217
acctacgtgg gtaagtttan aaatgttata atttcaggaa naggaacgca tataattgta      60
tcttgcctat aattttctat tttaataagg aaatagcaaa ttggggtggg gggaatgtag     120
ggcattctac agtttgagca aaatgcaatt aaatgtggaa ggacagcact gaaaaatttt     180
atgaataatc tgtatgatta tatgtctcta gagtagattt ataattagcc acttacccta     240
atatccttca tgcttgtaaa gt                                              262

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218
accaaggtgg tgcattaccg gaantggatc aangacacca tcgtggccaa cccctgagca      60
cccctatcaa ctccttttg tagtaaactt ggaaccttgg aaatgaccag gccaagactc     120
aggcctcccc agttctactg accttttgtcc ttangtntna ngtccagggt tgctaggaaa   180
anaaatcagc agacacaggt gtaaa                                           205

<210> SEQ ID NO 219
<211> LENGTH: 114
<212> TYPE: DNA
<213> ORGANISM: Homo sapien

<400> SEQUENCE: 219
tactgttttg tctcagtaac aataaataca aaaagactgg ttgtgttccg gccccatcca      60
accacgaagt tgatttctct tgtgtgcaga gtgactgatt ttaaaggaca tgga           114

<210> SEQ ID NO 220
<211> LENGTH: 93
<212> TYPE: DNA
<213> ORGANISM: Homo sapien

<400> SEQUENCE: 220
actagccagc acaaaaggca gggtagcctg aattgctttc tgctctttac atttctttta      60
aaataagcat ttagtgctca gtccctactg agt                                   93

<210> SEQ ID NO 221
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G
```

<400> SEQUENCE: 221

| actangtgca ggtgcgcaca aatatttgtc gatattccct tcatcttgga ttccatgagg | 60 |
| tcttttgccc agcctgtggc tctactgtag taagtttctg ctgatgagga gccagnatgc | 120 |
| cccccactac cttccctgac gctcoccana aatcacccaa cctctgt | 167 |

<210> SEQ ID NO 222
<211> LENGTH: 351
<212> TYPE: DNA
<213> ORGANISM: Homo sapien

<400> SEQUENCE: 222

| agggcgtggt gcggagggcg gtactgacct cattagtagg aggatgcatt ctggcacccc | 60 |
| gttcttcacc tgtcccccaa tccttaaaag gccatactgc ataaagtcaa caacagataa | 120 |
| atgtttgctg aattaaagga tggatgaaaa aaattaataa tgaattttg cataatccaa | 180 |
| ttttctcttt tatatttcta gaagaagttt ctttgagcct attagatccc gggaatcttt | 240 |
| taggtgagca tgattagaga gcttgtaggt tgcttttaca tatatctggc atatttgagt | 300 |
| ctcgtatcaa acaatagat tggtaaaggt ggtattattg tattgataag t | 351 |

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223

| aaaacaaaca aacaaaaaaa acaattcttc attcagaaaa attatcttag ggactgatat | 60 |
| tggtaattat ggtcaatta atwrtrttkt ggggcatttc cttacattgt cttgacaaga | 120 |
| ttaaaatgtc tgtgccaaaa ttttgtattt tatttggaga cttcttatca aaagtaatgc | 180 |
| tgccaaagga agtctaagga attagtagtg ttcccmtcac ttgtttggag tgtgctattc | 240 |
| taaaagattt tgatttcctg gaatgacaat tatattttaa ctttggtggg ggaaanagtt | 300 |
| ataggaccac agtcttcact tctgatactt gtaaattaat cttttattgc acttgttttg | 360 |
| accattaagc tatatgttta aaa | 383 |

<210> SEQ ID NO 224
<211> LENGTH: 320
<212> TYPE: DNA
<213> ORGANISM: Homo sapien

<400> SEQUENCE: 224

| cccctgaagg cttcttgtta gaaaatagta cagttacaac caataggaac aacaaaaga | 60 |
| aaaagtttgt gacattgtag tagggagtgt gtaccccta ctccccatca aaaaaaaaat | 120 |
| ggatacatgg ttaaaggata raagggcaat attttatcat atgttctaaa agagaaggaa | 180 |
| gagaaaatac tactttctcr aaatggaagc ccttaaaggt gctttgatac tgaaggacac | 240 |
| aaatgtggcc gtccatcctc ctttaragtt gcatgacttg gacacggtaa ctgttgcagt | 300 |
| tttaractcm gcattgtgac | 320 |

<210> SEQ ID NO 225
<211> LENGTH: 1214
<212> TYPE: DNA

<213> ORGANISM: Homo sapien

<400> SEQUENCE: 225

```
gaggactgca gcccgcactc gcagccctgg caggcggcac tggtcatgga aaacgaattg      60
ttctgctcgg gcgtcctggt gcatccgcag tgggtgctgt cagccgcaca ctgtttccag     120
aactcctaca ccatcgggct gggcctgcac agtcttgagg ccgaccaaga gccagggagc     180
cagatggtgg aggccagcct ctccgtacgg cacccagagt acaacagacc cttgctcgct     240
aacgacctca tgctcatcaa gttggacgaa tccgtgtccg agtctgacac catccggagc     300
atcagcattg cttcgcagtg ccctaccgcg gggaactctt gcctcgtttc tggctggggt     360
ctgctggcga acggcagaat gcctaccgtg ctgcagtgcg tgaacgtgtc ggtggtgtct     420
gaggaggtct gcagtaagct ctatgacccg ctgtaccacc ccagcatgtt ctgcgccggc     480
ggagggcaag accagaagga ctcctgcaac ggtgactctg ggggccccct gatctgcaac     540
gggtacttgc agggccttgt gtctttcgga aaagcccgt gtggccaagt tggcgtgcca      600
ggtgtctaca ccaacctctg caaattcact gagtggatag agaaaaccgt ccaggccagt     660
taactctggg gactgggaac ccatgaaatt gaccccaaa tacatcctgc ggaaggaatt      720
caggaatatc tgttcccagc ccctcctccc tcaggcccag gagtccaggc ccccagcccc     780
tcctccctca aaccaagggt acagatcccc agccctcct ccctcagacc caggagtcca      840
gaccccccag cccctcctcc ctcagaccca ggagtccagc ccctcctccc tcagacccag     900
gagtccagac cccccagccc ctcctccctc agacccaggg gtccaggccc caacccctc     960
ctccctcaga ctcagaggtc caagccccca cccctcctt cccagaccc agaggtccag      1020
gtcccagccc ctcctccctc agaccagcg gtccaatgcc acctagactc tccctgtaca     1080
cagtgccccc ttgtggcacg ttgacccaac cttaccagtt ggttttcat ttttgtccc      1140
tttcccctag atccagaaat aaagtctaag agaagcgcaa aaaaaaaaaa aaaaaaaaa     1200
aaaaaaaaaa aaaa                                                       1214
```

<210> SEQ ID NO 226
<211> LENGTH: 119
<212> TYPE: DNA
<213> ORGANISM: Homo sapien

<400> SEQUENCE: 226

```
acccagtatg tgcagggaga cggaacccca tgtgacagcc cactccacca gggttcccaa      60
agaacctggc ccagtcataa tcattcatcc tgacagtggc aataatcacg ataaccagt      119
```

<210> SEQ ID NO 227
<211> LENGTH: 818
<212> TYPE: DNA
<213> ORGANISM: Homo sapien

<400> SEQUENCE: 227

```
acaattcata gggacgacca atgaggacag ggaatgaacc cggctctccc ccagccctga      60
tttttgctac atatggggtc ccttttcatt ctttgcaaaa acactgggtt ttctgagaac     120
acggacggtt cttagcacaa tttgtgaaat ctgtgtaraa ccgggctttg caggggagat     180
aattttcctc ctctggagga aaggtggtga ttgacaggca gggagacagt gacaaggcta     240
gagaaagcca cgctcggcct tctctgaacc aggatggaac ggcagacccc tgaaaacgaa     300
gcttgtcccg ttccaatcag ccacttctga gaacccccat ctaacttcct actggaaaag     360
agggcctcct caggagcagt ccaagagttt tcaaagataa cgtgacaact accatctaga     420
```

```
ggaaagggtg caccctcagc agagaagccg agagcttaac tctggtcgtt tccagagaca    480
acctgctggc tgtcttggga tgcgcccagc ctttgagagg ccactacccc atgaacttct    540
gccatccact ggacatgaag ctgaggacac tgggcttcaa cactgagttg tcatgagagg    600
gacaggctct gccctcaagc cggctgaggg cagcaaccac tctcctcccc tttctcacgc    660
aaagccattc ccacaaatcc agaccatacc atgaagcaac gagacccaaa cagtttggct    720
caagaggata tgaggactgt ctcagcctgg ctttgggctg acaccatgca cacacacaag    780
gtccacttct aggttttcag cctagatggg agtcgtgt                            818

<210> SEQ ID NO 228
<211> LENGTH: 744
<212> TYPE: DNA
<213> ORGANISM: Homo sapien

<400> SEQUENCE: 228
actggagaca ctgttgaact tgatcaagac ccagaccacc ccaggtctcc ttcgtgggat     60
gtcatgacgt ttgacatacc tttggaacga gcctcctcct tggaagatgg aagaccgtgt    120
tcgtggccga cctggcctct cctggcctgt ttcttaagat gcggagtcac atttcaatgg    180
taggaaaagt ggcttcgtaa aatagaagag cagtcactgt ggaactacca aatggcgaga    240
tgctcggtgc acattggggt gctttgggat aaaagattta tgagccaact attctctggc    300
accagattct aggccagttt gttccactga agcttttccc acagcagtcc acctctgcag    360
gctggcagct gaatggcttg ccggtggctc tgtggcaaga tcacactgag atcgatgggt    420
gagaaggcta ggatgcttgt ctagtgttct tagctgtcac gttggctcct tccaggttgg    480
ccagacggtg ttggccactc ccttctaaaa cacaggcgcc ctcctggtga cagtgacccg    540
ccgtggtatg ccttggccca ttccagcagt cccagttatg catttcaagt ttggggtttg    600
ttcttttcgt taatgttcct ctgtgttgtc agctgtcttc atttcctggg ctaagcagca    660
ttgggagatg tggaccagag atccactcct taagaaccag tggcgaaaga cactttcttt    720
cttcactctg aagtagctgg tggt                                           744
```